US010501726B2

(12) United States Patent
Stice et al.

(10) Patent No.: US 10,501,726 B2
(45) Date of Patent: Dec. 10, 2019

(54) POPULATION OF ISOLATED CHICKEN CELLS REPROGRAMMED FROM SOMATIC CELLS

(71) Applicant: UNIVERSITY OF GEORGIA RESEARCH FOUNDATION, INC., Athens, GA (US)

(72) Inventors: Steven L Stice, Athens, GA (US); Franklin West, Bogart, GA (US); Yangqing Lu, Nanning (CN)

(73) Assignee: UNIVERSITY OF GEORGIA RESEARCH FOUNDATION, INC., Atlanta, GA (US)

( * ) Notice: Subject to any disclaimer, the term of this patent is extended or adjusted under 35 U.S.C. 154(b) by 0 days.

(21) Appl. No.: 15/164,618

(22) Filed: May 25, 2016

(65) Prior Publication Data

US 2016/0333319 A1 Nov. 17, 2016

Related U.S. Application Data

(63) Continuation of application No. 14/100,809, filed on Dec. 9, 2013, now abandoned, which is a continuation-in-part of application No. PCT/US2012/041873, filed on Jun. 11, 2012.

(60) Provisional application No. 61/495,499, filed on Jun. 10, 2011.

(51) Int. Cl.
*C12N 5/00* (2006.01)
*C12N 5/074* (2010.01)
*A01K 67/027* (2006.01)

(52) U.S. Cl.
CPC ........ *C12N 5/0696* (2013.01); *A01K 67/0271* (2013.01); *A01K 67/0275* (2013.01); *A01K 2207/12* (2013.01); *A01K 2227/30* (2013.01); *A01K 2267/02* (2013.01); *C12N 2501/60* (2013.01); *C12N 2501/602* (2013.01); *C12N 2501/603* (2013.01); *C12N 2501/605* (2013.01); *C12N 2501/608* (2013.01); *C12N 2502/99* (2013.01); *C12N 2506/02* (2013.01); *C12N 2506/1307* (2013.01); *C12N 2760/16111* (2013.01); *C12N 2760/18111* (2013.01); *C12N 2999/007* (2013.01)

(58) Field of Classification Search
USPC ................................................. 435/325, 455
See application file for complete search history.

(56) References Cited

U.S. PATENT DOCUMENTS

| | | | | |
|---|---|---|---|---|
| 6,156,569 A | * | 12/2000 | Ponce de Leon .. | A01K 67/0271 435/325 |
| 2011/0179510 A1 | * | 7/2011 | van de Lavoir ..... | C12N 5/0611 800/21 |
| 2014/0237633 A1 | * | 8/2014 | Van de Lavoir ... | A01K 67/0271 800/19 |
| 2014/0298504 A1 | * | 10/2014 | Van de Lavoir ... | A01K 67/0275 800/19 |

OTHER PUBLICATIONS

Pain (1996, Development, vol. 122, p. 2339-2348).*
Ivarie (Trends in Biotechnology, Jan. 2003, vol. 21, p. 14-19).*
Harvey (Nature Biotech., 2002, vol. 19, p. 396-399).*
Sang (Mech. Dev., 2004, vol. 121, p. 1179-1186).*
Wade (Poultry Sci., 2014, vol. 93, p. 799-809).*
Stadtfeld (Genes & Development, 2010, vol. 24, p. 2239-2243).*
Feng (Cell Stem Cell Review, 2009, vol. 4, p. 301-312).*
Takahashi (Cell, 2006, vol. 126, p. 663-676).*
Okita (Nature, 2007, vol. 448, p. 313-317).*
Takahashi K, Yamanaka S. Induction of pluripotent stem cells from mouse embryonic and adult fibroblast cultures by defined factors. Cell, 2006;126(4):663-676.
Yu J, et al. Induced pluripotent stem cell lines derived from human somatic cells. Science, 2007;318(5858):1917-1920.
Zhao XY, et al. iPS cells produce viable mice through tetraploid complementation. Nature, 2009;461(7260):86-90.
Thomson JA, et al. Embryonic stem cell lines derived from human blastocysts. Science, 1998;282(5391):1145-1147.
Takahashi K, et al. Induction of pluripotent stem cells from adult human fibroblasts by defined factors. Cell, 2007;131 (5):861-872.
West FD, et al. Porcine induced pluripotent stem cells produce chimeric offspring. Stem Cells Dev, 2010;19 (8):1211-1220.
Wu Y, Zhang Y, Mishra A, Tardif SD, Hornsby PJ. Generation of induced pluripotent stem cells from newborn marmoset skin fibroblasts. Stem Cell Res, 2010;4(3):180-188.
Hanna J, et al. Direct reprogramming of terminally differentiated mature B lymphocytes to pluripotency. Cell, 2008;133(2):250-264.
Haase A, et al. Generation of induced pluripotent stem cells from human cord blood. Cell Stem Cell, 2009;5 (4):434-441.
Aasen T, et al. Efficient and rapid generation of induced pluripotent stem cells from human keratinocytes. Nat Biotechnol. 2008;26(11):1276-1284.
Pain B, et al. Long-term in vitro culture and characterization of avian embryonic stem cells with multiple morphogenetic potentialities. Development, 1996;122(8):2339-2348.
Wu Y, Ge C, Zeng W, Zhang C. Induced multilineage differentiation of chicken embryonic germ cells via embryoid body formation. Stem Cells Dev, 2010;19(2):195-202.
Le Douarin NM. Embryonic neural chimaeras in the study of brain development. Trends Neurosci, 1993;16(2):64-72.
Alvarado-Mallart RM. The chick/quail transplantation model to study central nervous system development. Prog Brain Res, 2000;127:67-98.
Kikuchi T, et al. Clinical and metabolic correction of pompe disease by enzyme therapy in acid maltase-deficient quail. J Clin Invest, 1998;101(4):827-833.

(Continued)

*Primary Examiner* — Michael C Wilson
(74) *Attorney, Agent, or Firm* — Henry D. Coleman; R. Neil Sudol

(57) ABSTRACT

The present invention relates to the production of avian induced pluripotent stem cells from non-pluripotent somatic cells, including embryonic fibroblasts and adult somatic cells. In this method, avian (including quail or chicken) somatic cells are reprogrammed into a state closely resembling embryonic stem cells including the expression of key stem cell markers alkaline phosphatase, etc. by transfecting/transducing the non-stem cells with genes (preferably using a non-integrating vector as otherwise described herein or alternatively an integrating vector, such a lentiviral vector, retroviral vector or inducible lentiviral vector, among others) which express at least nanog, Lin28 and cMyc. In preferred aspects of the invention, the transfected/transduced vectors express nanog, Lig28, cMyc, Oct 4 (POU5F1 or PouV), SOX2 and KLF4. The induced stem cells which are produced contribute to all 3 germ layers, the trophectoderm and in certain aspects, the gonad in chimeric offspring.

10 Claims, 30 Drawing Sheets

Specification includes a Sequence Listing.

(56) References Cited

OTHER PUBLICATIONS

Chen L, Yang P, Kijlstra A. Distribution, markers, and functions of retinal microglia. Ocul Immunol Inflamm, 2002;10(1):27-39.
Zak PP, et al. The experimental model for studying of human age retinal degeneration (Japanese quail C. japonica). Dokl Biol Sci, 2010;434:297-299.
Sheykholeslami K, Kaga K, Mizutani M. Auditory nerve fiber differences in the normal and neurofilament deficient Japanese quail. Hear Res, 2001;159(1-2):117-124.
Kinutani M, Coltey M, Le Douarin NM. Postnatal development of a demyelinating disease in avian spinal cord chimeras. Cell, 1986;45(2):307-314.
Kulesa PM, Bailey CM, Cooper C, Fraser SE. In ovo live imaging of avian embryos. Cold Spring Harb Protoc, 2010;2010(6):pdb prot5446.
Le Douarin NM. Ontogeny of the peripheral nervous system from the neural crest and the placodes. A developmental model studied on the basis of the quail-chick chimacra system. Harvey Lect, 1984;80:137-186.
Le Douarin NM. Developmental patterning deciphered in avian chimeras. Dev Growth Differ, 2008;50 Suppl 1: S11-28.
Vali N. The Japanese Quail: A Review. International Journal of Poultry Science, 2008;7(9):925.
Huss D, Poynter G, Lansford R. Japanese quail (*Coturnix japonica*) as a laboratory animal model. Lab Anim (NY), 2008;37(11):513-519.
Petitte JN, Liu G, Yang Z. Avian pluripotent stem cells. Mech Dev, 2004;121(9):1159-1168.
MacDonald J, Glover JD, Taylor L, Sang HM, McGrew MJ. Characterisation and germline transmission of cultured avian primodial germ cells/ PLoS One, 2010;5(11):e15518.
Lavial F, Pain B. Chicken embryonic stem cells as a non-mammalian embryonic stem cell model. Dev Growth Differ, 2010;52(1):101-114.
Jung JG, et al. Development of novel markers for the characterization of chicken primordial germ cells. Stem Cells, 2005;23(5):689-698.
Van De Lavoir MC et al. Germline transmission of genetically modified primordial germ cells. Nature, 2006;441 (7094):766-769.
Park TS, Han JY. Derivation and characterization of pluripotent embryonic germ cells in chicken. Mol Reprod Dev, 2000;56(4):475-482.
Van De Lavoir MC, et al. High-grade transgenic somatic chimeras from chicken embryonic stem cells. Mech Dev, 2006;123(1):31-41.
Ezashi T, et al. Derivation of induced pluripotent stem cells from pig somatic cells. Proc Natl Acad Sci USA, 2009;106 (27):10993-10998.
Park TS, Kim MA, Lim JM, Han JY. Production of quail (*Coturnix japonica*) germline chimeras derived from in vitro-cultured gonadal primordial germ cells. Mol Reprod Dev, 2008;75(2):274-281.
Vates GE, Hashimoto T, Young WL, Lawton MT. Angiogenesis in the brain during development: the effects of vascular endothelial growth factor and angiopoietin-2 in an animal model. J Neurosurg, 2005;103(1):136-145.
Dupin E, Callon G, Real C, Goncalves-Trentin A, Le Douarin NM. Neural crest progenitors and stem cells. C R Biol, 2007;330(6-7):521-529.
Le Douarin NM, Tan K, Hallonet M, Kinutani M. Studying brain development with quail-chick neural chimeras. Kaibogaku Zasshi, 1993;68(2):152-161.
Teillet MA, Ziller C, Le Douarin NM. Quail-chick chimeras. Methods Mol Biol, 2008;461:337-350.
Zhang J, etal. Neural tube, skeletal and body wall defects in mice lacking transcription factor AP-2. Nature, 1996381 (6579):238-241.
Lewis JL, et al. Reiterated Wnt signaling during zebrafish neural crest development. Development, 2004;131 (6):1299-1308.
Meulemans D, Bronner-Fraser M. Gene-regulatory interactions in neural crest evolution and development. Dev Cell, 2004;7(3):291-299.

Shin S, et al. Long-term proliferation of human embryonic stem cell-derived neuroepithellal cells using defined adherent culture conditions. Stem Cells, 2006;24(1):125-138.
Lavial F, et al. The Oct4 homologue PouV and Nanog regulate pluripotency in chicken embryonic stem cells. Development, 2007; 134(19):3549-3563.
Avilion AA, et al. Multipotent cell lineages in early mouse development depend on SOX2 function. Genes Dev, 2003.
Ying QL, Nichols J, Chamber I, Smith A. BMP induction of Id proteins suppresses differentiation and sustains embryonic stem cell self-renewal in collaboration with STAT3. Cell, 2003;1 15(3):281-292.
Xu RH, et al. BMP4 initiates human embryonic stem cell differentiation to trophoblast. Nat Biotechnol, 2002;20 (12):1261-1264.
Nichols J, et al. Formation of pluripotent stem cells in the mammalian embryo depends on the POU transcription factor Oct4. Cell, 1998;95(3):379-391.
Sato N, Meijer L, Skaltsounis L, Greengard P, Brivanlou AH. Maintenance of pluripotency in human and mouse embryonic stem cells through activation of Wnt signaling by a pharmacological GSK-3-specific inhibitor. Nat. Med, 2004;10(1):55-63.
Ludwig TE, et al. Derivation of human embryonic stem cells in defined conditions. Nat Biotechnol, 2006;24 (2):185-187.
Capecchi MR. Altering the genome by homologous recombination. Science, 1989;244(4910):1288-1292.
Bronner-Fraser M. Neural crest cell formation and migration in the developing embryo. FASEB J, 1994;8 (10):699-706.
Wernig M, et al. Neurons derived from reprogrammed fibroblasts functionally integrate into the fetal brain and improve symptoms of rats with Parkinson's disease. Proc Natl Aced Sci U S A, 2008;105(15):5856-5861.
Msoffe PL, et al. Implementing poultry vaccination and biosecurity at the village level in Tanzania: a social strategy to promote health in free-range poultry populations. Trap Anim Health Prod, 2010;42(2):253-263.
Snoeck CJ, et al. Newcastle disease virus in West Africa: new virulent strains identified in non-commercial farms. Arch Virol, 2009;154(1):47-54.
Fasina FO, et al. Control versus no control: options for avian influenza H5N1 in Nigeria. Zoonoses Public Health, 2007,54(5):173-176.
Lyall J, et al. Suppression of avian influenza transmission in genetically modified chickens. Science, 2011;331 (6014):223-226.
Cornelissen LA, et al. A single immunization with soluble recombinant trimeric hemagglutinin protects chickens against highly pathogenic avian influence virus H5n1. PLoS One, 2010;5(5):e10645.
Rao S, et al. Multivalent HA DNA vaccination protects against highly pathogenic H5N1 avian influenza infection in chickens and mice. PLoS One, 2008;3(6):e2432.
West FD, Mumaw JL, Gallegos-Cardenas A, Young A, Stice SL. Human haploid cells differentiated from meiotic competent clonal germ cell lines that originated from embryonic stem cells. Stem Cells Dev, 2011;20:1079-1088.
Kee K, Angeles VT, Flores M, Nguyen HN, Reijo Pera RA. Human DAZL, DAZ and BOULE genes modulate primordial germ-cell and haploid garnete formation. Nature, 2009.
Wang Q, et al. GASZ promotes germ cell derivation from embryonic stem cells. Stem Cell Res, 2013;11:845-860.
Nayernia K, et al. In vitro-differentiated embryonic stem cells give rise to male gametes that can generate offspring mice. Dev Cell, 2006;11:125-132.
Antonarakis SE, Lyle R, Dermitzakis ET, Reymond A, Deutsch S. Chromosome 21 and down syndrome: from genomics to pathophysiology. Nat Rev Genet, 2004;5:725-738.
Hockner M, Pinggera GM, Gunther B, Sergi C, Fauth C, Erdel M, Kotzot D. Unravelling the parental origin and mechanism of formation of the 47,XY,i(X)(q10) Klinefelter karyotpye variant. Fertil Steril, 2008;90;2009 e13-7.
Mshelia GD, Amin JD, Woldehiwet Z, Murray RD, Egwu GO. Epidemiology of Bovine Venereal Campylobacteriosis: Geographic Distribution and Recent Advances in Molecular Diagnostic Techniques. Reprod Domest Anim, 2009.

(56) References Cited

OTHER PUBLICATIONS

Neal MS, Reyes ER, Fisher KS, King WA, Basrur PK. Reproductive consequences of an X-autosome translocation in a swine herd. Can Vet J, 1998;39:232-237.
Giesecke K, Sieme H, Distl O. Infertility and candidate gene markers for fertility in stallions: a review. Vet J, 2010;185:265-271.
Brown KH, Schultz IR, Cloud JG, Nagler JJ. Aneuploid sperm formation in rainbow trout exposed to the environmental estrogen 19{alpha}-ethynylestradiol. Proc Natl Acad Sci U S A, 2008;105:19786-19791.
Hauser R, Sokol R. Science linking environmental contaminant exposures with fertility and reproductive health impacts in the adult male. Fertil Steril, 2008;89:e59-65.
Hauser R, Chen Z, Pothier L, Ryan L, Altshul L. The relationship between human semen parameters and environmental exposure to polychlorinated biphenyls and p,p;—DDE. Environ Health Perspect, 2003;111:1505-1511.
Shamblott MJ, et al. Derivation of pluripotent stem cells from cultured human primordial germ cells. Proc Natl Acad Sci U S A, 1998;95:13726-13731.
Matsui Y, Toksoz D, Nishikawa S, Williams D, Zsebo K, Hogan BL. Effect of Steel factor and leukaemia inhibitory factor on murine primordial germ cells in culture. Nature, 1991;353:750-752.
Resnick JL, Bixler LS, Cheng L, Donovan PJ. Longer-term proliferation of mouse primordial germ cells in culture. Nature, 1992;359:550-551.
Mozdziak PE, Angerman-Stewart J, Rushton B, Pardue SL, Petitte JN. Isolation of chicken primordial germ cells using fluorescence-activated cell sorting. Poult Sci, 2005;84:594-600.
Mozdziak PE, Wysocki R, Angerman-Stewart J, Pardue SL, Petitte JN. Production of chick germline chimeras from fluorescence-activated cell-sorted gonocytes. Poult Sci, 2006;85:1764-1768.
IUCN2012. (Version 2012.2) The IUCN Red List of Threatened Species. <http://www.iucnredlist.org> Downloaded on Oct. 17, 2012.
Brooke MDE L, Butchart SH, Garnett ST, Crowley GM, Mantilla-Beniers NM, Stattersfield AJ. Rates of movement of threatened bird species between IUCN red list categories and toward extinction. Conserv Biol, 2008;22:417-427.
Ben-Nun IF, et al. Induced pluripotent stem cells from highly endangered species. Nat Methods, 2011;8:829-831.
Lavial F, et al. The Oct4 homologue PouV and Nanog regulate plurpotency in chicken embryonic stem cells. Development, 2007;134:3549-3563.
Pain B, Clark ME, Shen M, Nakazawa H, Sakurai M, Samarut J, Etches RJ. Long-term in vitro culture and characterisation of avian embryonic stem cells with multiple morphogenetic potentialities. Development, 1996;122:2339-2348.
Lu Y, et al. Avian-induced pluripotent stem cells derived using human reprogramming factors. Stem Cells Dev, 2012;21:394-403.
Wernig M, et al. In vitro reprogramming of fibroblasts into a pluripotent ES-cell-like state. Nature, 2007;448:318-324.
Li BC, et al. Directional differentiation of chicken primordial germ cells into adipocytes, neuron-like cells, and osteoblasts. Mol Reprod Dev, 2010;77:795-801.
Nakamura Y, et al. Migration and proliferation of primordial germ cells in the early chicken embryo. Poult Sci, 2007;86:2182-2193.
Dumstrei K, Mennecke R, Raz E. Signaling pathways controlling primordial germ cell migration in zebrafish. J Cell Sci, 2004;117:4787-4795.
Molyneaux KA, et al. The chemokine SDF1/CXCL12 and its receptor CXCR4 regulate mouse germ cell migration and survival. Development, 2003;130:4279-4286.
Doitsidou M, et al. Guidance of primordial germ cell migration by the chemokine SDF-1. Cell, 2002;111:647-659.
Motono M, Ohashi T, Nishijima K, Iijima S. Analysis of chicken primordial germ cells. Cyto technology, 2008;57:199-205.
Castrillon DH, Quade BJ, Wang TY, Quigley C, Crum CP. The human VASA gene is specifically expressed in the germ cell lineage. Proc Natl Acad Sci U S A, 2000;97:9585-9590.
Hay B, Jan LY, Jan YN. A protein component of *Drosophila* polar granules is encoded by vasa and has extensive sequence similarity to ATP-dependent helicases. Cell, 1988;55:577-587.
Tanaka SS, et al. The mouse homolog of *Drosophila vasa* is required for the development of male germ cell. Genes Dev, 2000;14:841-853.
Ikenishi K, Tanaka TS. Involvement of the protein of Xenopus vasa homolog (Xenopus vasa-like gene 1, XVLG1) in the differentiation of primordial germ cells. Dev Growth Differ, 1997;39:625-633.
MacDonald J, Glover JD, Taylor L, Sang HM, McGrew MJ. Characterisation and germline transmission of cultured avian primordial germ cells. PLoS One, 2010;5:e15518.
Lavial F, Acloque H, Bachelard E, Nieto MA, Samarut J, Pain B. Ectopic expression of Cvh (Chicken Vasa homologue) mediates the reprogramming of chicken embryonic stem cells to a germ cell fate. Dev Biol, 2009;330:73-82.
Xu EY, Moore FL, Pera RA. A gene family required for human germ cell development evolved from an ancient meiotic gene conserved in metazoans. Proc Natl Acad Sci, U S A, 2001;98:7414-7419.
Navarro-Costa P, et al. Incorrect DNA methylation of the DAZL promoter CpG island associates with defective human sperm. Hum Reprod, 2010;25:2647-2654.
Richardson TE, Chapman KM, Tenenhaus Dann C, Hammer RE, Hamra FK. Sterile testis complementation with spermatogonial lines restores fertility to DAZL-deficient rats and maximizes donor germline transmission. PLoS One, 2009;4:e6308.
Kee K, Angeles VT, Flores M, Nguyen HN, Reijo Pera RA. Human DAZL, DAZ and BOULE genes modulate primordial germ-cell and haploid gamete formation. Nature, 2009;462:222-225.
De Miguel MP, Cheng L, Holland EC, Federspiel MJ, Donovan PJ. Dissection of the c-Kit signaling pathway in mouse primordial germ cells by retroviral-mediated gene transfer. Proc Natl Acad Sci U S A, 2002;99:10458-10463.
Choi JW, et al. Basic fibroblast growth factor activates MEK/ERK cell signaling pathway and stimulates the proliferation of chicken primordial germ cells. PLoS One, 2010;5:e12968
Park HJ, Park TS, Him TM, Kim JN, Shin SS, Lim JM, Han JY. Establishment of an in vitro culture system for chicken preblastodermal cells. Mol Reprod Dev, 2006;73:452-461.
Rengaraj D, et al. Conserved expression pattern of chicken DAZL in primordial germ cells and germ-line cells. Theriogenology, 2010;74:765-776.
Ge C, Zhang C; Ye J, Tang X, Wu Y. Ginsenosides promote proliferation of chicken primordial germ cells via PKC-involved activation of NF-kappaB. Cell Biol Int, 2007;31:1251-1256.
Singh AM, Dalton S. The cell cycle and Myc intersect with mechanisms that regulate pluripotency and reprogramming. Cell Stem Cell, 2009;5:141-149.
Guo G, Yang J, Nichols J, Hall JS, Eyres I, Mansfield W, Smith A. F1f4 reverts developmentally programmed restriction of ground state pluripotency. Development, 2009;136:1063-1069.
Rossello RA, Chen CC, Dai R, Howard JT, Hochgeschwender U, Jarvis ED. Mammalian genes induce partially reprogrammed pluripotent stem cells in non-mammalian vertebrate and invertebrate species. Elife, 2013;2: e00036.
Van De Lavoir MC, et al. Interspecific germline transmission of cultured primordial germ cells. PLoS One, 2012;7: e35664.
Burt DW. Emergence of the chicken as a model organism: implication for agriculture and biology. Poult Sci, 2007;86:1460-1471.
Johnson PA, Giles JR. The hen as a model of ovarian cancer. Nat Rev Cancer, 2013;13:432-436.
Semple-Rowland SL, Lee NR, Van Hooser JP, Palczewski K, Baehr W. A null mutation in the photoreceptor guanylate cyclase gene causes the retinal degeneration chicken phenotype. Proc Natl Acad Sci U S A, 1998;95:1271-1276.
Lu Y, et al. Avian-induced pluripotent stem cells derived using human reprogramming factors. Stem Cells and Development 2012;21(3):394-403.
Hutcheson JM, et al. Delayed Newcastle disease virus replication using RNA interference to target the nucleoprotein. Biologicals, 2015;43:274-280.

(56) References Cited

OTHER PUBLICATIONS

Lu Y, et al. Induced Pluripotency in Chicken Embryonic Fibroblast Results in a Germ Cell Fate. Stem Cells and Development, 2014;23(15):1755-1764.
Yu P, et al. Nonviral Minicircle Generation of Induced Pluripotent Stem Cells Compatible with Production of Chimeric Chickens. Cellular Reprogramming, 2014;16(5):366-278.

* cited by examiner

E

POPULATION OF ISOLATED CHICKEN CELLS REPROGRAMMED FROM SOMATIC CELLS

RELATED APPLICATIONS AND GRANT SUPPORT

This application is a continuation of Ser. No. 14/100,809, filed Dec. 9, 2013 of identical title which is a continuation-in-part application which claims the benefit of priority of international patent application no. PCT/US2012/041873 filed on Jun. 11, 2012 entitled "Avian Induced Pluripotent Stem Cells and Their Use", which claims the benefit of priority of provisional application Ser. No. 61/495,499, filed Jun. 10, 2011 entitled "Avian Induced Pluripotent Stem Cells Generate Live Quail-chicken Chimeras and Undergo Advanced In Vitro Differentiation" the contents of which applications are incorporated herein in their entirety.

FIELD OF THE INVENTION

The present invention relates to the production of avian induced pluripotent stem cells from non-pluripotent somatic cells, including embryonic fibroblasts and adult somatic cells. In this method, avian (including quail or chicken) somatic cells are reprogrammed into a state closely resembling embryonic stem cells including the expression of key stem cell markers alkaline phosphatase, etc. by transfecting/transducing the non-stem cells with genes (preferably using a non-integrating vector as otherwise described herein or alternatively an integrating vector, such a lentiviral vector, retroviral vector or inducible lentiviral vector, among others) which express at least nanog, Lin28 and cMyc. In preferred aspects of the invention, the transfected/transduced vectors express nanog, Lin28, cMyc, Oct 4 (POU5F, 1 or PouV), SOX2 and KLF4. The induced stem cells which are produced contribute to all 3 germ layers, the trophectoderm and in certain aspects, the gonad in chimeric offspring. The experiments which are presented herein evidence that the induced quail and chicken pluripotent stem cells according to the present invention are bona fide stem cells that exist in a pluripotent state where they can be differentiated or turned into any cell type in the body or even a chimeric cell or mature bird. The present invention represents the first time that avian iPSCs were demonstrated to be capable of contributing to chimeric offspring, an essential component in their use as a biotechnology tool, including the preparation of vaccines. In alternative embodiments, avian induced pluripotent germ cells (aiPGCs) are produced from somatic cells using the methods which are described herein. These avian induced pluripotent germ cells (aiGSCs) exhibit behavior in developing embryo and offspring.

INTRODUCTION TO THE INVENTION

In mammals, embryonic stem cells (ESCs) and induced pluripotent stem cells (iPSCs) are highly proliferative populations capable of differentiating into multiple cell types and tissues representing all 3 germ layers and the germline (1-5). Similar to ESCs, mammalian iPSCs exhibit high levels of plasticity in both in vitro and in vivo environments (1). After the first derivation of mouse iPSCs in 2006, this technology has firmly proven its potency in generating iPSCs from various mammals and is advancing many scientific fields, from regenerative medicine to basic developmental biology (1, 2, 5-10). Given the diverse applications of mammalian iPSCs, avian iPSCs would have similar utility for developmental biologists, facilitating gene function and tissue transplant studies.

Although avian ESC and primordial germ cell (PGC) lines have been established (11, 12), they have not been used in gene targeting studies mostly likely because they have not been clonally isolated nor are they highly proliferative in extended cultures. Additionally, many of these avian lines have not been shown to robustly undergo directed in vitro differentiation into multiple lineages with phenotypic characteristic similar to mammalian pluripotent cells. Given some of the issues that plague the development of avian ESCs, the probability that avian iPSCs could be generated and show diverse differentiation potential in vitro and in vivo would seem unlikely. Generating non-mammal iPSCs faces other challenges and difficulties. Intuitively species specific or at least related reprogramming factors may be required for proper reprogramming and little is known of the required reprogramming factors in phylogenetically diverse species.

Avian embryonic models have a long history of providing critical new insights into developmental biology including organ function (13, 14), disease progression (e.g. Pompe disease) (15), eye disorders (16, 17) and many others (18, 19). The advantage that avian species have is their relative size and ease of access to the embryo for manipulation. Cells and tissues including whole sections of the spinal column can be transplanted into the avian embryo and can be monitored in real time during development (20). This is not possible in mammalian species. Moreover, the quail-chicken chimera is an attractive and widely used model for developmental patterning and cell fate studies given that cells can be readily tracked in this model (21, 22). The quail also has a short generation interval (3-4 generation per year)(23), facilitating genetic selection studies and experiments requiring multiple generational observations (24). Coupling a robust and clonal feeder free iPSC lines and derived committed cell lines or tissues with these model systems offers new opportunities to manipulate and study developmental process both in vitro and in vivo.

In the present application it is demonstrated for the first time in a non-mammalian species the successful generation of highly proliferative quail and chicken iPSC populations amenable to genetic manipulation and capable of generating live chimeric offspring and undergoing advanced directed neural differentiation in vitro. These first iPSCs in a non-mammalian species demonstrate the highly conserved nature of the reprogramming genes and provide for future mechanistic developmental studies in well characterized avian models.

The present invention also relates to germ cell development wherein pluripotent germ cells are induced from non-pluripotent somatic cells, including embryonic fibroblast cells and adult somatic cells. Germ cells are critically important as the vehicle that passes genetic information from one generation to the next. Correct development of these cells is essential and perturbation in their development often leads to reproductive failure and disease. Despite the importance of germ cells, little is known about the mechanisms underlying the acquisition and maintenance of the germ cell character. Using a reprogramming strategy, the present invention provides a method which demonstrates that over-expression of ectopic transcription factors in embryonic fibroblast and other somatic cells can lead to the generation of avian (chicken) induced-PGCs (ciPGCs). These ciPGCs express pluripotent markers POU5F1, SSEA1 and the germ cell defining proteins CVH and DAZL, closely resembling in vivo sourced PGCs instead of embryonic stem cells (ESCs). Moreover, it was shown that CXCR4 expressing ciPGCs of the present invention were capable of migrating to the embryonic gonad after injection into the vasculature of stage 15 embryos, indicating the acquisition of a germ cell fate in these cells. Direct availability of ciPGCs in vitro are useful to facilitate the study of germ cell development as well as providing a potential strategy for conservation of important genetics of agricultural and endangered birds using somatic cells.

The importance of understanding the molecular mechanisms driving germ cell development from an unspecified pluripotent cell to a fully functional gamete, and the factors that inhibit this process, has prompted interest in differentiating a pluripotent stem cell (PSC) to a primordial germ cell (PGC) and then finally to a mature germ cell (GC). The PSC differentiation process using embryonic (ESC) or induced pluripotent stem cells (iPSC) requires both sequential and simultaneous critical initiating events, ranging from GC specification andepigenetic reprogramming to meiosis [1-4]. Normal GC development is essential for the successful transfer of genetic material from one generation to the next and perturbation of this process is a leading cause of infertility in humans as well as bovine, porcine, equine and many other species [5-9]. The causative agents of abnormal GC development range from simple genetic mutations to environmental contaminants and significant chromosomal rearrangement [10-12].

Despite the utility and strength of PSCs, significant prohibitive limitations exists in mammalian systems. Often times it would be preferable to directly manipulate PGC cultures instead of PSCs. PGCs are likely more representative of a nave in vivo germ line transmissible cell type than the undifferentiated PSCs, thus their response to a germ cell toxin or other perturbations may be more representative of how PGCs and eventually GCs behave in the developing embryo and offspring. However, PGC studies are difficult in mammals since mouse PGCs, when cultured in vitro, do not maintain a PGC phenotype and will revert back to a cell type that is equivalent and resembles ESC [13-15]. These considerations need to be acknowledged when studying critical signaling or exposure to a toxin and subsequent transfer into an in vivo setting to examine transgenerational effects. In contrast, chicken and other avian PGCs may be easily isolated from embryos at several time-point in germ cell development and migration, i.e. germinal crescent, blood or nascent gonad [16,17], do not undergo overt dedifferentiation to an ESC like cell and they can be propagated as PGCs [18]. When transferred into the developing embryo, cultured PGCs migrate to the genital ridge fully undergoing GC development and have been used in avian transgenic studies. However, the early specification and developmental events of PGCs in the chicken are challenging to study as they happen before the egg is laid. A chicken iPSC germ cell differentiation system will enable the study of germ cell development from early specification to functional gamete.

PGCs have significant potential for the development of transgenic animals on unique backgrounds or conservation of valuable genetics as in the case of endangered birds. Over 1300 avian species, or 13% of the total population, are threatened by extinction, and an additional 880 species are threatened [19]. Although various conservation measures such as habitat protection and captive reproduction are a solution used to protect and repopulate endangered birds, the overall number of species is still on the decline and some of them are extinct [20]. A PSC to GC approach offers an additional theoretical strategy for the conservation of genetic diversity and repopulation of the endangered avian species and studies using unique adult genotypes [21].

In one embodiment, the present invention demonstrated that quail iPSCs could be generated from somatic cells using human pluripotency transcription factors and revealed that the regulatory mechanisms of pluripotency are conserved across species. Therefore, it was viewed that it might be possible to reprogram chicken somatic cells using similar factors and chicken and other avian germ cell culture conditions to derive chicken or other avian germ cells [18,23]. In the present invention, the inventors have successfully generated PSCs by over expression of human transcription factors in chicken somatic cells. The PSCs express typical stem cell markers and were capable differentiating into all 3 germ layers. Moreover, these induced chicken PSCs when propagated in medium used to expand PGCs expressed important germ cell genes such as CVH and DAZL. Functional tests demonstrated that these newly reprogrammed chicken induced primordial germ cells (ciPGCs) were capable of migrating to the embryonic gonad after injection into stage 15 chicken embryos, an indication of germ cell fate. The capability to derive PGCs from somatic cells is the first step towards definitive GC studies in birds and provides a new strategy for conservation of endangered birds as well as a cell source for the study of toxicology in germ cell development.

BRIEF DESCRIPTION OF THE INVENTION

Figure 1:
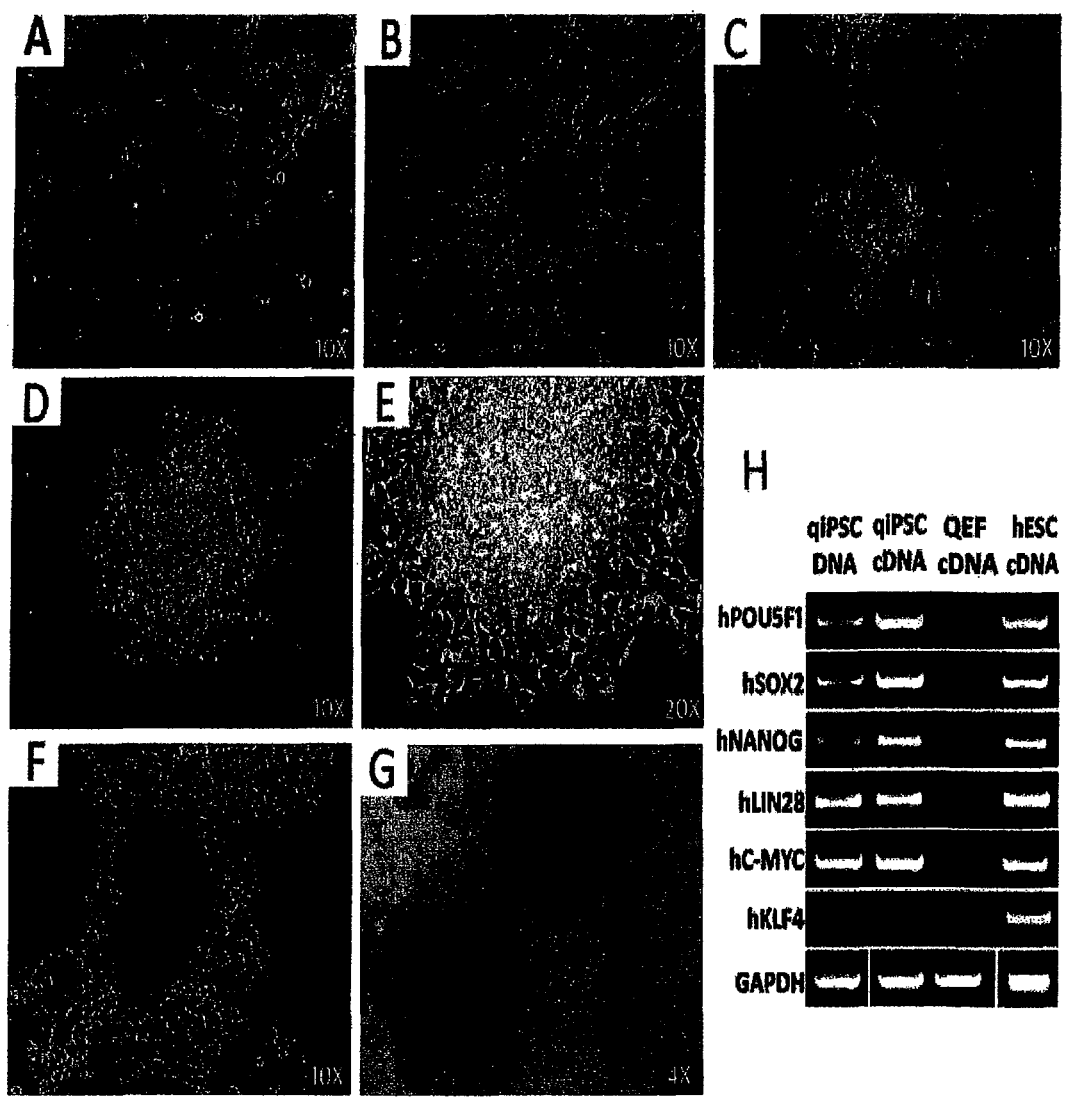
FIG. 1 shows the derivationof quail induced pluripotent stem cells (qiPSCs) from quail embryonic fibroblast cells (QEFs). QEFs prior to addition of reprogramming factors (A). Incomplete reprogrammed QEFs maintain a fibroblast-like morphology at day 6 post-transduction (B), while qiPSC colonies at day 17 showed defined borders (C) and at the single cell level a high nuclear to cytoplasm ratio, clear cell boarders and prominent nucleoli (D, E). qiPSCs were positive for Alkaline Phosphotase (AP; F) and Periodic Acid Schiff's (PAS) staining (G). 5 out of 6 human pluripotent stem cell factors were integrated and expressed in qiPSCs (H).

In one embodiment, the present invention relates to a method of inducing embryonic and/or mature avian, in particular, quail or chicken, somatic cells, including fibroblasts, to a pluripotent stem cell state (expressing the pluripotent stem cell markers Nanog, PouV (Oct 4) and preferably also SSEA1) comprising transfecting or transducing (often transfecting) said somatic cells (which can be from any number of avian species, especially including quail and chickens, preferably avian fibroblast cells, more preferably avian embryonic fibroblast cells) with at least three reprogramming genes consisting of Nanog, Lin28 and c-Myc and optionally, at least one additional reprogramming gene selected from the group consisting of Oct 4 (POU5F1 or PouV), SOX2 and KLF4 such that the somatic cell, after reprogramming, exhibits characteristics of an avian induced pluripotent stem cell (aiPSC).

In another embodiment, the present invention relates to a method of inducing embryonic and/or mature avian, in particular, chicken or quail, among other somatic cells, including fibroblasts, to a pluripotent germ cell state (expressing the pluripotent germ markers cell markers Nanog, PouV (Oct 4) and SSEA1, as well as the germ cell markers DAZL, CVH, EMA1 and CXCR4 as well as C-KIT)) comprising transfecting or transducing (often transfecting) said somatic cells (which can be from any number of avian species, especially including chicken and quail, preferably avian fibroblast cells, more preferably avian embryonic fibroblast cells) with at least four reprogramming genes consisting of Pou5F1 (PouV or Oct4), Nanog, SOX2 and Lin28 and optionally, c-Myc such that the somatic cell, after reprogramming, exhibits characteristics of an avian induced pluripotent germ cell (aiPSC).

In the present invention, at least one reprogramming vector population expressing the reprogramming genes is used to reprogram the cells, preferably more than one reprogramming vector population is used, preferably as many reprogramming vector populations as there are reprogramming genes to be transfected or transduced are used such that each reprogramming vector population comprises no more than one reprogramming gene (e.g., Nanog, Lin28, c-Myc, Oct4 (POU5F1 or PouV), SOX2, KLF4, depending on whether the desired pluripotent cell to be produced is a pluripotent stem cell or a pluripotent germ cell). In various aspects of the invention, the reprogramming vector is a non-integrating or integrating vector preferably selected from the group consisting of a circle DNA vector (episomal DNA), a lentiviral vector, an inducible lentiviral vector or a retroviral vector, preferably, a circle DNA vector or a lentiviral vector, and each vector preferably comprises only one reprogramming gene per vector). The somatic cells are transfected/transduced with the reprogramming vectors and reprogrammed under conditions wherein said reprogramming genes optionally integrate with the genome of the somatic cells, thus producing avian induced pluripotent stem cells (aiPSCs) according to the present invention. By introducing the reprogramming genes from the transfected/transduced vectors into the somatic cells, the somatic cells are thus converted into an induced pluripotent stem cell (iPSC) state, which closely resembles embryonic stem cells (as evidenced by their expressed biomarkers, as well as their differentiation capacity and other physical and functional characteristics), or the somatic cells are converted into inducted pluripotent germ cells (iPGCs), which closely resemble naturally occurring pluripotent germ cells. The induced pluripotent cells may be expanded/propagated in nutrient medium (e.g., stem cell expansion medium, germ cell explanation medium or related enriched culture medium), optionally stored (e.g. by cryopreservation) and used in differentiation processes to produce differentiated cells such as neural cells or muscle cells or gamete cells as in the case of aiPGCs or to genetically manipulate phenotypic changes in an avian population, preferably including chickens.

The avian (e.g. chicken or quail) induced pluripotent stem cells (iPSCs) or pluripotent germ cells (iPGCs) according to the present invention can be used in a number of ways to genetically manipulate chickens or other commercially relevant avian species, including turkeys. Genes (expressing a desired/modified phenotype) can be introduced into either the somatic cells which are used to derive iPSCs or iPGCs or directly into iPSCs or iPGCs which have been produced. These cells can then be utilized in a variety of differentiation methods to form differentiated cells such as neural cells or other differentiated cells or to form chimeras (e.g. by injecting genetically manipulated iPSCs or iPGCs into embryos) which can be used to generate offspring with the modified phenotype. In the case of iPGCs, these cells can be used also to differentiate into gametes, which can be used to produce or generate offspring with the modified phenotype. The phenotypes could include, but are not limited to, animals that exhibit improved production and disease resistance (in particular, Avian flu and/or Newcastle disease) or the development of animals to study specific diseases and/or injury.

Another aspect of the invention relates to chimeric embryos which are produced by injecting aiPSCs or aiPGCs into avian embryos (generally contained within eggs) in an effective amount, and allowing the chimeric embryo to grow to maturity. The resulting matured embryos exhibit phenotypic characteristics of the wild-type or native embryo as well as those of the aiPSCs or aiPGCs. In a method aspect of the invention, chimeric embryos and/or mature chimeric chickens according to the invention are produced by injecting an effective population of aiPSCs or aiPGCs (generally from about 1,000 to 50,000 or more, preferably about 8500-15,000, about 10,000 cells) into an avian, preferably chicken embryo in an egg shell anytime during stage X to XV, preferably at stage X soon after incubation begins (preferably within the first few hours of incubation), by providing an opening in the shell and injecting the cells (preferably, those cells exhibiting disease resistance) into the subgerminal cavity of an avian, preferably chicken egg. The chimeric embryo produced by injecting the aiPSCs/aiPGCs into the embryo is allowed to grow and mature, thus producing a chimeric embryo soon after injection (generally, between two and tens days after injection, depending upon the stage X-XV when the aiPSC/aiPGC is injected into the embryo, exhibiting at least in part, the characteristics of the injected aiPSCs/aiPGCs. The resulting chimeric embryo may be grown to maturity producing chimeric adults exhibiting characteristics of the aiPSCs/aiPGCs, including resistance to disease, other desired characteristics or they may be used in vaccine production or research.

In an alternative embodiment, the aiPSCs/aiPGCs can be used to produce a chimeric germline cell, by introducing the aiPSCs/aiPGCs into a germline cell population, thus producing a chimeric germline cell, which can mature into gametes such that any selected trait which is introduced into the aiPSCs/aiPGCs, including disease resistance, may be transmitted to offspring through the gamete. In an alternative method, the aiPSCs/aiPGCs (which may advantageously exhibit advantageous selected traits such as disease resistance) are injected into the reproductive organs, including the testes or ovaries of an adult bird and in the environment of the testes or ovaries, differentiate into sperm cells or ova.

In an alternative embodiment according to the present invention aiPSCs/aiPGCs are selected for disease resistance (Cellular Adaptive Resistance or CAR) by exposing the naïve cells (i.e., those cells not exposed to a disease agent), generally about 10×109 or more cells) to a disease agent for which resistance as a trait is desired (e.g. Newcastle disease, Avian influenza) in a growth medium for a period sufficient to induce cell death in a large majority of cells (often approaching 100% of the naïve cells), generally at least about 48 hours to about 72 hours, preferably at least about 72 hours where almost all cells (generally, greater than 99%, and often close to 100% of the naïve cells) die from infection. A small percentage of the original naïve cells that survive are then isolated/collected, expanded and utilized to produce disease resistant differentiated cells and/or tissue or chimeric embryos which will allow the maturation of the embryos into disease resistant adults (especially commercially relevant chickens, turkeys, quail or geese). In this aspect of the invention, the resistant cells which are isolated may be reprogrammed pursuant to methods according to the present invention to increase the number of aiPSCS/aiPGCs in the resistant cell population. Given that species specific cell lines offer potential for species specific vaccines, these resistant cells may be particularly useful for providing a better host for species specific vaccines, especially where vaccines could be generated from a specific genetic or tissue specific genetic or epigenetic background that is shown to be a better host for the production of vaccines, for example, an animal infected with a virus, but cells from it demonstrate resistance to cell death.

In another embodiment, the present invention is directed to a cell viability assay for identifying cells which are viable and resistant after exposure to a disease agent as described above. In this assay, a measurement of metabolic activity of the cells exposed to disease agent after an appropriate time (e.g. 72 hours) is taken by measuring the conversion of MTS tetrazolium ([3-(4,5-dimethylthiazol-2-yl)-5-(3-carboxymethonyphenol)-2-(4-sulfophenyl)-2H-tetrazolium, inner salt]) to formazan (colorimetric) due to the production of NADPH and NADH during normal cellular respiration and comparing the decline with a standard (usually a population of cells which are resistant or non-resistant to the disease agent). A decline in the conversion of MTS tetrazolium to formazan as evidenced by a reduction in the intensity or the absence of color from formazan formation indicates non-viability, whereas a conversion to formazan which is approximately the same as or slightly higher than the viable resistant cells is indication of viability. This method is preferably conducted using flow cytometry. In certain aspects of the invention, viable resistant aiPSCs/aiPGCs demonstrate metabolic activity which is at least about 10 times, at least about 20 times, at least about 25 times, at least about 30 times and at least about 35-40 times the metabolic activity of naïve cells after exposure to ND virus which are not resistant.

In a further embodiment, a method referred to as the aiPSC/aiPGC virus exposure survival and recovery assay, is used to determine the resistance of cells in a sample. In this assay a sample of resistant aiPSCs or resistant aiPGCs which have been exposed previously to a disease agent (e.g. ND virus) is plated, exposed to the disease agent and then measured to determine viability. Resistant cells evidence higher cell numbers at earlier points in time and a more rapid increase in cell numbers over time at later points in time evidencing a faster recovery rate in comparison to naïiv cells which have not been exposed to the disease agent. In the present invention, resistant aiPSCs/aiPGCs demonstrated a higher survival than naïve aiPSCs/aiPGCs at early (about 12-14 fold or more higher than naïve aiPSCs/aiPGCs) and later (20 to 26 fold or more high than naïve aiPSCs/aiPGCs) time points, evidencing a resistant population of aiPSCs/aiPGCs which exhibits increased survivability and rapid recovery of resistant cell lines.

Thus, in one aspect, the present invention is directed to a method for producing avian induced pluripotent stem cells comprising providing a population of somatic cells, preferably quail, chicken, turkey, duck or geese somatic cells (including fibroblast cells, especially embryonic fibroblast cells), to be reprogrammed to pluripotent stem cells (PSCs) or pluripotent germ cells (PGCs), transfecting or transducing these somatic cells with at least one population of reprogramming vectors (preferably more than one reprogramming vector) comprising reprogramming genes selected from at least Nanog, Lin28 and c-Myc and optionally one or more of Oct4 (POU5F1 or PouV), SOX2 and KLF4 in the case of PSCs, or Oct4 (Pou5F1 or PouV), SOX2, Nanog and LIN28, and optionally c-MYC in the case of PGCs, allowing said reprogramming genes to reprogram said somatic cells into pluripotent stem cells or pluripotent germ cells and optionally, separating and/or isolating said pluripotent stem cells (PSCs) or pluripotent germ cells (PGCs).

The present invention is directed to embodiments related to one or more of the following specific embodiments of the invention, among others.

A population of avian induced pluripotent stem cells reprogrammed from avian somatic cells, said somatic cells being reprogrammed with at least the three reprogramming genes Nanog, LIN28 and c-MYC and optionally, at least one reprogramming gene selected from the group consisting of OCT4, SOX2 and KLF4.

The population of cells wherein the cells have been reprogrammed with Nanog, LIN28, c-MYC, Oct4 and optionally SOX 2, KLF4 or a mixture of SOX 2 and KLF4.

The population of cells wherein the cells have been reprogrammed with Nanog, LIN28, c-MYC, SOX2 and optionally Oct4 and/or KLF4.

The population of cells above wherein the cells have been reprogrammed with Nanog, LIN28, c-MYC and SOX2.

The population of cells above wherein the cells have been reprogrammed with Nanog, LIN28, c-MYC, KLF4 and optionally, SOX2 and/or Oct4.

The population of cells above wherein the cells have been reprogrammed with Nanog, LIN28, c-MYC, Oct4, SOX2 and KLF4.

The population of cells above wherein the cells have been reprogrammed with Nanog, LIN28 and c-MYC in the absence of Oct4, SOX2 and KLF4.

The population of cells above wherein the somatic cells are embryonic somatic cells, preferably, embryonic fibroblast cells.

The population of cells above wherein the somatic cells are adult somatic cells.

A population of avian induced pluripotent germ cells reprogrammed from avian somatic cells, said somatic cells being reprogrammed with at least the reprogramming genes OCT4(Pou4F1/PouV), SOX2, Nanog and LIN28 and optionally, c-MYC.

The population of cells wherein the cells have been reprogrammed with OCT4(Pou4F1/PouV), SOX2, Nanog, LIN28 and c-MYC.

The population of cells above wherein the somatic cells are adult fibroblast cells.

The population of cells above wherein the somatic cells are reprogrammed by transfecting or transducing the cells with at least one vector comprising the reprogramming genes.

The population of cells above wherein the reprogramming genes are avian or mammalian genes each of which has a sequence homology of at least about 50% of the identical gene of the avian species from which the somatic cells are reprogrammed.

The population of cells above wherein the reprogramming genes are chicken, mouse, human, pig or cow genes.

The population of cells above wherein the cells are transfected or transduced with vectors wherein each of said vectors comprises a single reprogramming gene.

The population of cells above wherein the avian induced pluripotent cell is a quail, chicken, turkey, duck or goose pluripotent cell.

A population of induced avian pluripotent stem cells exhibiting the following four characteristics:
 form colonies with cells with a high nuclear to cytoplasmic ratio ranging from about 4.1 to about 1:2;
 express alkaline phosphatase;
 are developmentally identical to avian embryonic stem cells (aESCs); and
 are capable of in vitro differentiation to all three germ layer types (mesoderm, endoderm and ectoderm) as determined by gene expression.

The population of pluripotent stem cells above wherein the cells exhibit one or more of the following characteristics:
 express the following genes and proteins: Nanog, PouV, Sox2;
 exhibit a normal karyotype;
 express high levels of telomerase; and
 express Periodic Acid Schiff (PAS).

The population of pluripotent stem cells described above wherein the cells exhibit one or more of the following characteristics:
 express at least one of of the cell surface markers SSEA1, SSEA3, SSEA4, TRA 1-61 and TRA 1-81;
 exhibit stable/robust pluripotency and can differentiate or contribute to chimeras even after more than 25 passages;
 fast cell cycle with high population doubling;
 when injected into avian embryos, contribute to all germ cell lineages during development;
 chimera generate protein and morphologically distinct cells in vitro such as neurons and muscle cells, among numerous others; and
 the cells are clonigenic.

A population of induced avian pluripotent germ cells exhibiting at least four of the following characteristics:
 aiPGC Characteristics
 Morphologically possess high nucleus to cytoplasm ratio and large nucleoli
 Cell populations express Alkaline Phosphotase, SSEA1, EMA1, POU5F1, SOX2, NANOG, Chicken Vasa Homolog (CVH), DAZL, CXCR4, C-KIT and express high levels of telomerase
 Cells migrate to the gonad when injected in vivo
 aiPGCs can be maintained in adherent or suspension culture; traditional PGCs are cultured in suspension
 aiPGCs can be derived from any somatic cell of the body
 aiPGCs show robust differentiation in vitro
 aiPGCs incorporate transfection/transduction vectors which express reprogramming genes
 iPGCs are capable of differentiating into all 3 germ layers in vitro
 Can be used to generate gametes (ova and sperm)
 Can be used to generate chimeric animals
 Can be expanded in adherent cultures
 aiPGCs are produced by growing reprogrammed somatic cells in Avian Induced Primordial Germ Cell Programming and Expansion Media and expand poorly in cKSR which is a typical iPSC media.

The population of pluripotent stem cells or pluripotent germ cells described above which have been instilled with disease resistance from a disease agent.

The population of pluripotent stems cells or pluripotent germ cells described above wherein the disease agent is an agent against which a vaccine is to be made.

The population of pluripotent stem cells or pluripotent germ cells described above wherein the disease agent is Newcastle disease virus or an influenza virus, especially avian influenza virus.

The population of pluripotent stem cells or pluripotent germ cells described above wherein the cells are reprogrammed after an initial reprogramming.

The population of cells reprogrammed after an initial reprogramming which cells express SSEA1.

A chimeric bird produced from pluripotent stem cells or pluripotent germ cells described above.

The chimeric bird described above which is a quail, chicken, turkey, duck or goose, often a chicken or turkey, most often a chicken.

The chimeric bird described above which exhibits resistance to a disease agent, including Newcastle disease virus or avian influenza virus.

A bird produced from pluripotent germ cells (which are differentiated or mature into gametes) described above.

The bird described above which is a quail, chicken, turkey, duck or goose, often a chicken or turkey, most often a chicken.

The bird described above which exhibits resistance to a disease agent, including Newcastle disease virus or avian influenza virus.

A method comprising reprogramming an avian embryonic or adult somatic cell to an avian induced pluripotent stem cell (aiPSC) or an avian induced pluripotent germ cell (aiPGC), the method (in the case of aiPSCs) comprising transfecting or transducing the somatic cell with the three reprogramming genes Nanog, Lin28 and c-Myc and optionally, at least one reprogramming gene selected from the group consisting of Oct 4 (Pou5F1/PouV), SOX2 and KLF4, or (in the case of aiPGCs) with the four reprogramming genes Oct 4 (Pou5F1/PouV), SOX2, Nanog, LIN28 and optionally c-MYC, allowing the genes to reprogram the somatic cells into pluripotent stem cells or pluripotent germ cells and optionally, isolating and/or expanding the stem or germ cells, wherein each of the reprogramming genes is an avian or mammalian gene which exhibits at least about 50% sequence homology with the identical gene from the species from which the somatic cells are reprogrammed.

The method described above wherein the avian somatic cell is reprogrammed with the reprogramming genes Nanog, LIN28, c-MYC, Oct4, SOX2 and KLF4 to produce avian induced pluripotent stem cells (aiPSCs).

The method described above wherein the avian somatic cell is reprogrammed with the reprogramming genes Oct4, SOX2, Nanog, LIN28 and c-MYC to produce avian induced pluripotent germ cells (aiPGCs).

The method described above wherein the reprogramming genes are human, chicken, mouse, pig or cow genes.

The method described above wherein the reprogramming genes are transduced into the somatic cells via a viral vector and integrated into the genome of the somatic cell.

The method described above wherein the reprogramming genes are transfected into the somatic cells via a non-integrating reprogramming vector.

The method described above wherein the somatic cells have been reprogrammed with Nanog, LIN28, c-MYC; Oct4 and optionally SOX 2, KLF4 or a mixture of SOX 2 and KLF4.

The method described above wherein the cells have been reprogrammed with Nanog, LIN28, c-MYC, SOX2 and optionally Oct4 and/or KLF4.

The method described above wherein the somatic cells have been reprogrammed with Nanog, LIN28, c-MYC and SOX2.

The method described above wherein the stomatic cells have been reprogrammed with Nanog, LIN28, c-MYC, KLF4 and optionally, SOX2 and/or Oct4.

The method described above wherein the cells have been reprogrammed with Nanog, LIN28, c-MYC, Oct4, SOX2 and KLF4.

The method described above wherein the cells have been reprogrammed with Nanog, LIN28 and c-MYC in the absence of Oct4, SOX2 and KLF4.

The method described above wherein the somatic cells are embryonic somatic cells, often embryonic fibroblast cells or adult somatic cells, including adult fibroblast cells.

The method described above wherein the somatic cells are reprogrammed by transfecting or transducing the cells with at least one vector comprising the reprogramming genes.

The method described above wherein the vector is a viral vector and the reprogramming genes integrate into the genome of the somatic cell to produce the induced pluripotent stem cell.

The method described wherein the vector is a non-viral vector and the reprogramming genes are non-integrated with the genome of the somatic cells to produce the induced pluripotent stem cell.

The method described above wherein the somatic cells are transfected or transduced with vectors wherein each of the vectors comprises a single reprogramming gene.

The method described above wherein the avian induced pluripotent cell is a quail, chicken, turkey, duck or goose pluripotent cell, often a chicken pluripotent cell.

The method described above wherein the pluripotent stem cells or the pluripotent germ cells once produced are reprogrammed at least one further time and express SSEA1.

A method of genetically manipulating avian species, especially chickens, comprising selecting and introducing genes into somatic cells to be reprogrammed into avian iPSCs or aiPGCs or directly into avian aiPSCs or aiPGCs or to produce genetically manipulated aiPSCs or aiPGCs, introducing the genetically manipulated avian aiPSCs cells or aiPGCs into avian embryos to form chimeric embryos; and generating offspring with the chimeric embryos, wherein said offspring exhibit a phenotype consistent with the introduced genes.

The method described above wherein the genes are introduced directly into said aiPSCs or aiPGCs.

The method described above wherein the genes are introduced into the somatic cells before being reprogrammed to iPSCs or aiPGCs.

The method described above wherein the genetically manipulated aiPSCs or aiPGCs are introduced into a subgerminal cavity of the embryos and the embryos are allowed to mature.

The method described above wherein the genetically manipulated aiPGCs are matured or differentiated into gametes from which a bird is reproduced. A bird produced by such a method.

The method described above wherein the genetically manipulated aiPGCs are introduced into the gonads of an avian species and allowed to mature into gametes from which a bird is reproduced. A bird produced by such a method.

The method described above wherein the embryo is a chicken, turkey or duck embryo, often a chicken embryo.

A method of instilling disease resistance in an avian induced pluripotent stem cell (aiPSC) or an avian induced pluripotent germ cell (aiGSC), the method comprising producing an avian induced pluripotent stem cell or avian induced pluripotent germ cell from somatic cells according to any of the methods described above, exposing the pluripotent cells to a disease agent for a period of time sufficient to produce resistance to the disease agent in the cells so that more than 99% of the population of the pluripotent stem cells or pluripotent germ cells succumb to the disease agent, isolating the remaining viable cells, optionally testing the cells for resistance to the disease agent and optionally, propagating the resistant cells to provide a population of avian induced pluripotent stem cells or avian induced pluripotent germ cells exhibiting resistance to the disease agent.

A method of instilling disease resistance into a population of avian induced pluripotent stem cells or avian induced pluripotent germ cells from disease resistant somatic cells, the method comprising producing disease resistant somatic cells by exposing somatic cells to a disease agent for a period of time sufficient to produce resistance to the disease agent in the cells, more than 99% of the population of which succumb to the disease agent, isolating the resistant somatic cells, propagating the cells to provide a population of resistant somatic cells and producing a population of disease resistant avian induced pluripotent stem cells or avian induced pluripotent germ cells from the disease resistant somatic cells according to any of the methods described above.

The method described above wherein the resistant aiPSCs or aiPGCs are injected into an avian embryo to produce a chimeric bird, the chimeric bird exhibiting resistance to the disease agent.

The method described above wherein the resistant aiPGCs are allowed to mature into gametes or are differentiated into gametes which may be used to reproduce disease resistant birds.

A method described above wherein the bird is a chicken and the disease agent is Newcastle disease virus or avian influenza virus.

A method of producing a chimeric avian gamete comprising administering into a germline cell an avian induced pluripotent stem cell or an avian induced pluripotent germ cell described above to produce a chimeric germline cell, introducing the chimeric germline cell into the testes or ovaries of an adult bird and isolated a chimeric gamete after a period sufficient to produce the chimeric gamete from the germline in the adult bird.

A method of producing an avian gamete cell comprising introducing an aiPGC into the testes or ovaries of an adult bird and isolating the gamete after a period sufficient to produce the gamete from the aiPGC in the adult bird.

The method described above wherein said gamete is an ovum or a sperm.

A method of producing immunogenic material for a vaccine comprising providing a population of aiPSCs or aiPGCs resistant to a disease agent described above, growing the disease agent in the population of aiPSCs or aiPGCs and removing the disease agent from the population of aiPSCs or aiPGCs after said growing step.

The method described above wherein the disease agent is influenza virus or Newcastle disease virus.

The method described above wherein said disease agent is inactivated after the removing step.

The method described above wherein the disease agent is inactivated before being grown in the aiPSCs or aiPGCs.

A vaccine produced with immunogenic material prepared according to the method described above.

aiPSCs according to the present invention exhibit a robust clonal rate of 20% (i.e. a single cell will produce a colony of cells 20% of the time). This unique feature of aiPSCs according to the present invention allows these cells to be particularly useful in studies that require multiple clonal isolation, such as complex genetic manipulation or virus screening, among others.

In an embodiment according to the present invention, the present invention is directed to a method comprising reprogramming an avian embryonic or adult somatic cell to an avian induced pluripotent germ cell (aiPGC), the method comprising transfecting or transducing the somatic cell with the four reprogramming genes Oct4 (Pou5F, 1 or PouV), SOX2, Nanog and Lin28 and optionally, c-Myc, allowing the genes to reprogram the somatic cells into pluripotent germ cells (which are believed to pass through a transitory pluripotent stem cell which could not be isolated on their way to a germ cell state) and optionally, isolating and/or expanding the germ cells, wherein each of the reprogramming genes is an avian or mammalian gene which exhibits at least about 50% sequence homology with the identical gene from the species from which the somatic cells are reprogrammed.

In a further embodiment, the present invention is directed to a population of avian cells consisting essentially of avian induced pluripotent germ cells having the following characteristics similar to or distinguishable from other related cells):

aiPGC Characteristics
Similarities to non-induced (wild-type) PGCs:
Morphologically both possess high nucleus to cytoplasm ratio and large nucleoli
Both cell populations express Alkaline Phosphotase, SSEA1, EMA1, POU5F1, NANOG, Chicken Vasa Homolog (CVH), DAZL, CXCR4, C-KIT and express high levels of telomerase
Both migrate to the gonad
aiPGCs are the functional equivalents to non-induced PGCs. However there are differences:
aiPGCs can be maintained in adherent or suspension culture, while traditional PGCs are cultured in suspension
aiPGCs can be derived from any somatic cell of the body
aiPGCs show robust differentiation in vitro
aiPGCs incorporate transaction/transduction vectors which express reprogramming genes
aiPGC Similarities to induced pluripotent stem cells (aiPSCs):
Both cell populations express the pluripotency markers Alkaline Phosphotase, SSEA1, POU5F1, SOX2 and NANOG
Morphologically both possess high nucleus to cytoplasm ratio and large nucleoli
Both (intermediary PSC/PGC and aiPSCs) are capable of differentiating into all 3 germ layers in vitro
Both can be used to generate chimeric animals
Both can be expanded in adherent cultures
a. Differences between aiPGCs and the aiPSCs disclosed previously:
aiPGCs express CVH, EMA-1 and DAZL while iPSCs do not.
aiPGCs are capable of active migrating to the gonad while iPSCs do not.
aiPGCs are preferably grown in Avian Induced Primordial Germ Cell Programming and Expansion Media and expand poorly in cKSR which is a typical iPSC media.

DETAILED DESCRIPTION OF THE INVENTION

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compositions and methods are disclosed and described, it is to be understood that this invention is not limited to specific conditions, or specific methods, etc., as such may, of course, vary, and the numerous modifications and variations therein will be apparent to those skilled in the art.

Standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

The term "subject", or in some instances, "patient" is used throughout the specification within context to describe an animal, generally an animal which is a member of an avian species, especially, for example, a quail, a chicken, a turkey or other commercially relevant species which is exposed to methods and/or compositions which are described herein (including vectors and/or cells) according to the present invention. For treatment of those infections, conditions or disease states which are specific for a specific animal including a human patient, the term patient refers to that specific animal, including numerous avian species, especially quail, chicken, turkeys, ducks and geese, among others.

The terms "transfect", "transfecting", "tranduct", "transduction" are used (in many instances synonymously) to describe a process of introducing nucleic acids into cells pursuant to the present invention. The term transfecting is used notably for introducing non-viral DNA (generally plasmids, although naked DNA, including supercoiled naked DNA and RNA including modified mRNA and Micro-RNA may also be used) into eukaryotic cells, but the term may also refer to other methods and cell types, although other terms may also be used. Transfection or transduction of animal cells typically involves opening transient pores or "holes" in the cell membrane, to allow the uptake of material into the cells to be transfected. Transfection is often carried out using an agent such as calcium phosphate or other agent to assist transfection into the target cell, by electroporation, or by mixing a cationic lipid with the material to produce liposomes, which fuse with the cell membrane and deposit cargo within the cell. Transduction is a term which describes the process by which foreign DNA is introduced or transferred from one bacterium to another by a virus. This term also refers to the process whereby foreign DNA is introduced into another cell via a viral vector, as are preferred aspects of the present invention. Transduction does not require cell-to-cell contact (which occurs in conjugation), and it is DNAase resistant, but it often is benefited by the inclusion of a transduction factor such as GeneJammer™ or TransDux™ transduction reagents. Transduction is a relatively common tool used by those of skill to stably introduce or integrate a foreign gene into a host cell's genome.

The term "somatic cell" is used to describe any cell which forms the body of a multicellular organism that is other than a gamete, germ cell, gametocytes or undifferentiated stem cell. In contrast to somatic cells, gametes are cells that are involved in sexual reproduction, germ cells are gamete precursory cells and stem cells are cells that can divide (mitosis) and differentiate into a variety of cell types. In avian species, somatic cells make up all of the internal organs, skin, feathers, bones, blood, and connective tissue. Somatic cells are diploid. According to the present invention any avian somatic cell may be used to induce pluripotent stem cells, but preferred somatic cells for use in the present invention include those cells which may be readily propagated, especially including fibroblast cells, including adult fibroblast cells. Embryonic fibroblast cells are preferred for use in the present invention although stomach cells, liver cells, keratinocytes, amniotic cells, blood cells, adipose cells, neural cells, melanocytes, among numerous others, may also be used.

The term "germ cell" is used to describe a biological cell that is a pluripotent precursor cell that eventually matures into gametes of an organism that engages in sexual reproduction. In many animals, the germ cells originate near the gut of an embryo and migrate to the developing gonads of the embryo. There, in the gonads, they undergo cell division, which is of two types, mitosis and meiosis and these cells further differentiate into mature gametes (eggs or sperm). In avian species and mammals, the germ cell lines are established by signals controlled by genes in the zygotes of the animal.

The term "avian induced pluripotent stem cells" (aiPSCs), of which "quail induced pluripotent stem cells" (qiPSCs), "chicken induced pluripotent stem cells" (ciPSCs), turkey induced pluripotent stem cells" (tiPSCs) and goose induced pluripotent stem cells (giPSCs) are a subset, are derived from avian somatic cells by reprogramming the somatic cells with at least three reprogramming genes including NANOG; LIN28 and c-MYC, and optionally one or more of Oct4 (POU5F1, PouV) SOX2 and KLF4 using transfection and/or transduction of the reprogramming genes in certain instances (when higher efficiency is desired) to preferably integrate the genes into the genome of the somatic cells. Avian induced pluripotent stem cells include both adult and embryonic induced pluripotent stem cells, often produced from adult fibroblast cells or embryonic fibroblast cells.

Included in the definition of avian induced pluripotent stem cells or (aiPSCs) are adult and embryonic cells from various types of somatic cells, preferably fibroblast cells, often embryonic fibroblast cells. Any cells of avian origin that are capable of producing progeny that are derivatives of all three germinal layers are included, regardless of whether they were derived from adult somatic cells, embryonic somatic tissue (e.g., embryonic fibroblasts), fetal, or other sources. The aiPSCs are preferably not derived from a malignant source.

aiPSCs according to the present invention exhibit a robust clonal rate of 20% (i.e. a single cell will produce a colony of cells 20% of the time). This unique feature of aiPSCs according to the present invention allows these cells to be particularly useful in studies that require multiple clonal isolation, such as complex genetic manipulation or virus screening, among others.

aiPSC cultures are described as "undifferentiated" when a substantial proportion of the stem cells and their derivatives in the population display morphological characteristics of undifferentiated cells, clearly distinguishing them from differentiated cells of embryo or adult origin. Undifferentiated aiPSCs are easily recognized by those skilled in the art, and typically appear in the two dimensions of a microscopic view in colonies of cells with high nuclear/cytoplasmic ratios and prominent nucleoli. It is understood that colonies of undifferentiated cells in the population may often be surrounded by neighboring cells that are differentiated. "Naïve" aiPSCs refer to aiPSCs that have not been exposed to a disease agent (such as Newcastle disease virus or avian flu virus). "Resistant" aiPSCs refer to aiPSCs that have been exposed to a disease agent and are viable after such exposure compared to non-resistant aiPSCs, which exhibit substantially reduced metabolic activity compared to resistant aiPSCs in the virus exposure cell viability assay as otherwise described herein.

aiPSCs according to the present invention generally display the following characteristics:
1. Form colonies with cells with a high nuclear to cytoplasmic ratio (ranging from about 4:1 to about 1:2 nuclear to cytoplasmic, often about 2.1);
2. Express alkaline phosphatase;
3. Are developmentally identical to avian embryonic stem cells (aESCs);
4. Are capable of in vitro differentiation to all three germ layer types (mesoderm, endoderm and ectoderm) as determined by gene expression;
5. Express the following genes and proteins: Nanog, PouV, Sox2;
6. Exhibit a normal karyotype (euploid with all avian chromosomes present and an absence of altered chromosomes);
7. Express high levels of telomerase (often 5-10 fold greater than somatic cells); and
8. Express Periodic Acid Schiff (PAS).
Of the above eight (8) characteristics, the first four (4) are always present; and any one or more (1, 2, 3 or 4, preferably all 4) of characteristics 5-8 are usually present.

aiPSCs according to the present invention often exhibit one or more (1, 2, 3, 4, 5 or 6) of the following characteristics:
9. Expression of at least one (i.e., one, two, three, four or five) of the cell surface markers SSEA1, SSEA3, SSEA4, TRA 1-61 and TRA 1-81;
10. Exhibit stable/robust pluripotency—can differentiate or contribute to chimeras even after more than 25 passages;
11. Fast cell cycle with high population doubling (often, at least about 1.2 or higher the rate or more of embryonic stem cells);
12. When injected into avian, preferably chick embryos, contribute to all germ cell Lineages during development;
13. Chimera generate protein and morphologically distinct cells in vitro such as neurons and muscle cells, among numerous others;
14. The cells are clonigenic—i.e., can give rise to a colony of aiPSCs from a single cell.

aiPSCs according to the present invention usually do not exhibit the following characteristics unless those characteristics are further induced in the cell population:
13. Resistance to cell death induced by lethal viruses (Newcastle disease, avian flu, etc.)

aiPSCs according to the present invention are distinguishable over avian embryonic pluripotent stem cells (ESCs) in the following ways:
1. The embryonic stem cells (ESCs) and aiPSCs are produced in entirely different ways from different cellular origins (ESCs obtained from blastocyst stage embryo vs. somatic cells for aiPSCs).
2. The aiPSCs exhibit much more stable potency than ESCs. aiPSCs exhibit robust differentiation even after >25 passages, whereas ESCs exhibit differentiation slowdown after about 20-25 passages.
3. aiPSCs can contribute to chimeras even after >25 passages, whereas the ESCs lose the ability to contribute to chimeras after about 20-25 passages.
4. The aiPSCs exhibit a faster population doubling than ESCs (in some cases at least about 1.2 or higher the rate of population doubling of ESCs).
5. aiPSCs are often clonigenic (because of the fast cell cycle and stable pluripotency) and exhibit a clonal rate of about 10-20% or sometimes higher (i.e., where a single cell will produce a colony at least 10-20% of the time) whereas the ESCs are generally non-clonigenic.

A desirable phenotype of propagated aiPSCs is the high potential to differentiate into cells of all three germinal layers: endoderm, mesoderm, and ectoderm tissues. Pluripotency of pluripotent stem cells which may be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers, using RT-PCR as otherwise described herein.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all chromosomes are present and not noticeably altered.

At any time the propagated aiPSCs may be re-exposed to the reprogramming vectors (DNA integrating or non-integrating transient expression) and selected again for pluripotent traits as provided above, especially including positive expression of the biomarker SSEA1.

The term "avian induced pluripotent germ cells" (aiPGCs), of which "induced chicken pluripotent germ cells" (icPGCs), "induced quail pluripotent germ cells" (iqPGCs), "induced turkey pluripotent germ cells" (itPGCs) and "induced goose pluripotent germ cells" (igPGCs) are a subset, are derived from avian somatic cells by reprogramming the somatic cells with the reprogramming genes Oct4 (Pou5F1 or PouV), SOX2, NANOG and LIN28 and optionally c-MYC, using transfection and/or transduction of the reprogramming genes in certain instances (when higher efficiency is desired) to preferably integrate the genes into the genome of the somatic cells. Avian induced pluripotent germ cells (aiPGCs) according to the present invention may be produced from both adult and embryonic somatic cells, often from adult or embryonic fibroblast cells, more often embryonic fibroblast cells.

Included in the definition of avian induced pluripotent germ cells or (aiPGCs) are aiPGCs produced from various types of somatic cells, preferably fibroblast cells. Any cells of avian origin that are capable of producing gametes are included, regardless of whether they were derived from adult somatic cells, embryonic somatic tissue (e.g., embryonic fibroblasts), fetal, or other sources. The aiPGCs are preferably not derived from a malignant source.

aiPGCs according to the present invention generally display the following characteristics:
  Morphologically possess high nucleus to cytoplasm ratio and large nucleoli
  Cell populations express Alkaline Phosphotase, SSEA1, EMA1, POU5F1, SOX2, NANOG, Chicken Vasa Homolog (CVH), DAZL, CXCR4, C-KIT and express high levels of telomerase
  Cells migrate to the gonad
  aiPGCs can be maintained in adherent or suspension culture; traditional PGCs are cultured in suspension
  aiPGCs can be derived from any somatic cell of the body
  aiPGCs show robust differentiation in vitro
  aiPGCs incorporate transfection/transduction vectors which express reprogramming genes
  intermediary PSCs are capable of differentiating into all 3 germ layers in vitro
  Can be used to generate chimeric animals
  Can be expanded in adherent cultures
  aiPGCs are preferably grown in Avian Induced Primordial Germ Cell
  Programming and Expansion Media and expand poorly in cKSR which is a typical iPSC media.

The term "chimera" refers to cells and/or embryos in which aiPSCs according to the present invention have been introduced. Pursuant to the present invention, aiPSCs may be injected into avian embryos to instill those embryos with certain favorable characteristics which may introduced into the aiPSCs, including resistance to disease agents such as Newcastle disease virus, avian influenza virus or other traits. aiPSCs may be introduced into an embryo preferably at embryonic Stage X to XV (i.e., from the point that an egg is freshly laid (about 20 hours uterine age) to about 6-8 hours of that time, although embryos of greater maturity may also be manipulated to produce a chimeric offspring. See, for example, Kochav, et al., *Developmental Biology,* 79, 296-308, 1980 and Eyal-Giladi, et al., *Developmental Biology,* 49, 321-337, 1976. Alternatively, a germline chimera may be produced (introduction of the aipSCS into germlines cells to produce germline chimeras) so that the germ cells may mature into gametes (ova or sperm) and any selected trait which is incorporated into the aiPSC may be transmitted to the offspring. Alternatively, aiPSCs may be injected directly into the testes of a chicken, such that in that environment The term "avian embryonic stem cell" refers to embryonic pluripotent cells, of avian origin, which are isolated from the blastocyst stage embryo. Embryonic stem cell refers to a stem cell from an avian species and are used for comparison purposes to the avian induced pluripotent stem cells of the present invention. Many of the physical and functional characteristics of aESCs are identical to aiPSCs, although there are some difference of functional significance.

The term "reprogramming" refers to a process pursuant to the present invention whereby avian somatic cells are supplied, transfected or transduced with a population of reprogramming vectors comprising the reprogramming genes Nanog, LIN28 and c-MYC and optionally one or more of Oct4 (Pou5F1 or PouV), SOX2 and KLF4 in the case of aiPSCs or Oct 4 (Pou5F1), SOX2, Nanog and LIN28, and optionally C-MYC, and reprogrammed such that each of the genes which are transfected or transduced into the somatic cells is incorporated into cell and preferably integrated with the somatic cell genome, whereby the reprogrammed genes instill characteristics in the somatic cells to produce a population of avian induced pluripotent stem cells (aiPSCs) or avian induced pluripotent germ cells (aiPSCs). Accordingly, the term reprogramming is used generically herein to describe a process by which a somatic cell is induced to become a pluripotent stem cell (PSC) or pluripotent germ cell (PGC) pursuant to the present invention. In certain preferred aspects, the reprogramming genes integrate into the genome of the somatic cells, but integration is not required to induce the somatic cells to a pluripotent stem cell state or pluripotent germ cell state, although such an approach is often efficient. In other preferred aspects of the invention, reprogramming genes are non-integrating and instead activate the endogenous pluripotency genes, resulting in alternative favorable characteristics (including the tendency to have much lower incidence of mutation and tumor formation).

The term "reprogramming genes" refers to the genes which are transfected or transduced into the avian somatic cells, are preferably integrated into the somatic cell genome and as a consequence of the expression of the induced polynucleotides reprogram or induce the somatic cells to a pluripotent stem cell state or a pluripotent germ cell state which the art refers to as an induced pluripotent stem cell or avian induced pluripotent stem cell (aiPSC) or induced pluripotent germ cell or avian induced pluripotent germ cell (aiPGC). In the case of aiPSCs, these genes include the following six genes, the first three of which are necessary and the last three of which are optionally used. These genes include Nanog, LIN28 and c-MYC as being required to produce avian induced pluripotent stem cells according to the present invention and additional genes which are optional, including one or more of POU5F1 (PouV), SOX2 and KLF4. It is noted that POU5F1 and PouV are the human and chicken homologues of Oct4 (octamer-binding transcription factor 4). It is an unexpected result that reprogramming of avian (preferably including chicken) somatic cells into aiPSCs may be induced using only the three genes Nanog, LIN28 and c-MYC as described. In the case of aiPGCs, the reprogramming genes include four genes, namely, OCT4 (Pou5F1 or PouV), SOX2, Nanog and Lin28 and optionally, a fifth reprogramming gene, C-MYC. It is noted that the reprogramming genes used to reprogram somatic cells into PSCs or PGCs may be from any number of avian or mammalian species, including humans, but preferably these genes are from avian sources, preferably a source which exhibits species identity with that of the somatic cell which is to be reprogrammed.

In general, the genes which are employed to reprogram the avian somatic cells pursuant to the present invention, have a sequence homology identity which is at least 50%, 55%, 60%, 65%, 70%, 75%, 80%, 85%, 90%, 95%, 99% up to 100% of the genes from the species from which the somatic cells to be induced to pluripotent cells are obtained and are generally from mammalian or avian species.

The term "reprogramming vector" is used to describe a transfection or transduction vector which may be used to reprogram a somatic cell to produce aiPSCs or aiPGCs according to the present invention. Preferred reprogramming vectors for use in the present invention may be integrating or non-integrating and include viral vectors, especially integrating lentiviral vectors (see, Yu, et al., Science, 38, 1917-1920, 2007; Stadtfeld, et al., Curr. Biol., 18, 890-894, 2008; Sommer, et al., Stem Cells, 27, 543-549, 2009; Anoyke, Danso, et al, Cell Stem Cell, 8, 376-388, 2011), retroviral vectors (see, Takahashi, et al., Cell, 126, 663-676, 2006; Takahashi, et al., Cell, 131, 861-872, 2007; Lowry, et a, Proc. Natl. Acad. Sci. USA, 105, 2883-2888, 2008; and Huangfu, et al., Nature Biotechnol., 26, 1269-1275, 2008) and inducible retroviral vectors (see, Maherali, N., Cell Stem Cell, 3, 340-345, 2008 and Stadtfeld, et al., Cell Stem Cell, 2, 230-240, 2008). Alternative vectors which may be used include, for example, non-integrating vectors, which may be preferred in certain aspects of the invention, such as adenoviral vectors (Zhou, et al., Stem Cells, 27, 2667-2674, 2009 and Stadtfeld, et al., Science, 322, 949-953, 2008), plasmid vectors (Okita, et al., Science, 322, 949-953, 2008 and Si-Tayeb, et al., BMC Dev., Biol., 1081, 2010), excisable vectors including transposon (Woltjen, et al., Nature, 458, 766-770, 2009) and loxP-lentiviral vectors (Somers, et al., Stem Cells, 28, 1728-1740, 2010) and DNA free vectors, including Sendai virus vectors (Fusaki, et al., Proc. Jpn Acad. 85, 348-362, 2009), protein vectors (Kim, et al., Cell Stem Cell, 4, 472-476, 2009 and Zhou, et al, Cell Stem Cell, 4, 381-384, 2009), modified mRNA vectors (Warren, et al., Cell Stem Cell, 7, 618-630, 2010) and MicroRNA vectors (Miyoshi, et al., Cell Stem Cell, 8, 633-638, 2011), as discussed generally in Robinton & Dailey, Nature, 481, 295-305, January 2012 and as generally known in the art. Vectors used in the present invention are well known in the art and may be purchased, readily constructed and manipulated to incorporate reprogramming genes using standing genetic engineering methods.

In the present invention vectors are prepared using methods which are generally known in the art. A number of reprogramming vectors are available commercially, from establishments including the viPS™ Vector Kit (integrating), developed by ArunA Biomedical Inc., Athens, Ga., and made available commercially by Thermo Fisher Scientific, Inc., Waltham Mass., USA or Minicircle DNA™ (non-integrating episomal DNA vectors) available from System Biosciences, LLC, Mountainview Calif., USA), the Piggy-Bac™ Mouse 4-in-1 Transposon Vector (non-integrating), also available from System Biosciences, LLC. and Non-integrating modified mRNAs of the reprogramming genes (e.g., Stealth Express™ exogenous gene expression system, available from Allele Biotechnology, San Diego, Calif. USA) expressing at least the reprogramming genes required for reprogramming (Nanog, LIN28, c-Myc).

The viPS™ Vector Kit for reprogramming fibroblasts (or other differentiated somatic cells) into induced pluripotent stem cells was developed by Thermo Fisher Scientific, Inc. in collaboration with ArunA Biomedical, Inc. Six transcription factors/genes (Lin28, c-Myc, Klf4, Nanog, Sox2 and Oct4 (Pou5f1)) have been cloned into a lentiviral vector system to create a resource for producing induced pluripotent stem (iPS) cells allowing for the generation of patient- and disease-specific cells. Ectopic expression of these factors has been shown to create pluripotent cells which resemble embryonic stem (ESCs) cells. The set of six factors is available in high-titer virus, ready for transduction. Separate vectors each of which expresses a single reprogramming gene are preferably used in the present invention. These vectors are commercially available from Thermo Fisher Scientific, Inc. or Systems Biosciences, LLC, as well as other sources and alternatively, may be readily prepared by inserting the relevant DNA sequence into the vector, the sequence of which genes are available online at Genebank.

The viPS™ vector kit lentiviral vectors express human Oct4 (POU5F1), Sox2, Nanog, Klf4, c-Myc, and/or Lin28 under control of the human elongation factor-1 alpha promoter (EF1α) or alternatively a CMV, SV40, UBC, PGK and/or CAGG promoter. Vectors are generated by PCR amplifying each pluripotency factor open reading frame (ORF) followed by direct cloning downstream of the EF1α promoter. Endonuclease restriction sites placed within the PCR primers are used to facilitate cloning. A Kozak consensus sequence may also be included to ensure efficient translation.

Minicircles are episomal DNA vectors that are produced as circular expression cassettes devoid of any bacterial plasmid DNA backbone. Their smaller molecular size enables more efficient transfections and offers sustained expression over a period of weeks as compared to standard plasmid vectors that only work for a few days. They are non-integrating. Non-integrating or footprint free transfection of reprogramming genes using mRNA (transposon vectors or cDNA expression vectors (minicircles) or even non-integrating virus such as Sendi virus or adenovirus, described above, may often be used to generate aiPSCs or aiPGCs according to the present invention because these systems are less likely to induce a mutation (and possibly a tumor in the resulting chimeric bird) because the reprogramming genes do not integrate into the somatic cell genome using these methods of transfection/transduction. With non-integrating systems the gene cannot be turned on later (as with integrated genes) and induce tumors, which may be preferably in certain instances. However, the integrating vectors described above (lentivirus, retrovirus, inducible retrovirus and additionally, adenoassociate virus AAV vectors) are usually more efficient, with higher and more uptake and reprogramming to aiPSCs.

The cDNAs used for PCR are obtained from the Human Pluripotency Tool Kit™ (Catalogue number PPK4919), which consists of: Oct4 (Pou5f1) (NM_002701, Incyte clone ID:LIFESEQ259583); Sox2 (NM_003106. IMAGE clone ID:2823424); Nanog (NM_024865. IMAGE clone ID: 40004920); Klf4 (NM_004235, IMAGE clone ID: 5111134); c-Myc (NM_002467, IMAGE clone ID: 2985844); and Lin28 (NM_024674, IMAGE clone ID: 841184), although a number of other cDNAs may also be used (see, for example, below). In the case of alternative reprogramming genes from other mammalian and/or avian species, including chickens, these are obtained by nucleotide synthesis of the gene sequences for each of the identified reprogramming genes. Examples include the following genes listed in the table below:

TABLE 1A

Pluripotent Reprogramming Genes

| Species | Genes Name | Gene ID | mRNA reference |
|---|---|---|---|
| Chicken (*Gallus gallus*) | OCT4 | 427781 | NM_001110178.1 |
| | SOX2 | 396105 | NM_205188.1 |
| | NANOG | 100272166 | NM_001146142.1 |
| | LIN28 | 428206 | NM_001031774.2 |
| | CMYC | 420332 | NM_001030952.1 |
| | KLF4 | 770254 | XM_001233583.2 |
| Mouse (*Mus musculus*) | OCT4 | 18999 | NM_001252452.1 |
| | SOX2 | 20674 | NM_011443.3 |
| | NANOG | 71950 | NM_028016.2 |
| | LIN28 | 83557 | NM_145833.1 |
| | CMYC | 17869 | NM_001177352.1 |
| | KLF4 | 16600 | NM_010637.3 |
| Human (*Homo sapiens*) | OCT4 | 5460 | NM_001173531.1 |
| | SOX2 | 6657 | NM_003106.3 |
| | NANOG | 79923 | NM_024865.2 |
| | LIN28 | 79727 | NM_024674.4 |
| | CMYC | 4609 | NM_002467.4 |
| | KLF4 | 9314 | NM_004235.4 |
| Pig (*Sus scrofa*) | OCT4 | 100127461 | NM_001113060.1 |
| | SOX2 | 407739 | NM_001123197.1 |
| | NANOG | 100170132 | NM_001129971.1 |
| | LIN28 | 100142662 | NM_001123133.1 |
| | CMYC | 448810 | NM_001005154.1 |
| | KLF4 | 595111 | NM_001031782.2 |
| Cattle (*Bos Taurus*) | OCT4 | 282316 | NM_174580.2 |
| | SOX2 | 784383 | NM_001105463.1 |
| | NANOG | 538951 | NM_001025344.1 |
| | LIN28 | 614997 | NM_001193057.1 |
| | CMYC | 511077 | NM_001046074.2 |
| | KLF4 | 520842 | NM_001105385.1 |

One of ordinary skill can identify the various reprogramming genes from a variety of avian and/or mammalian species with the requisite homology, synthesize the cDNA's in each instance and incorporate the cDNA's into reprogramming vectors as otherwise described herein to transfect/transduce avian somatic cells and provide aiPSCs according to the present invention.

In the case of the pVIPS lentiviral vector, each of the pluripotency factor ORFs has been sequenced verified. For efficient expression, the preferred lentiviral vector used in the present invention also contains a woodchuck hepatitis virus post-transcriptional regulatory element (WPRE) and the pput/cPPT (CTS, DNA flap) sequence. The pVIPS lentiviral vector is self-inactivating (SIN).

Figure 20:
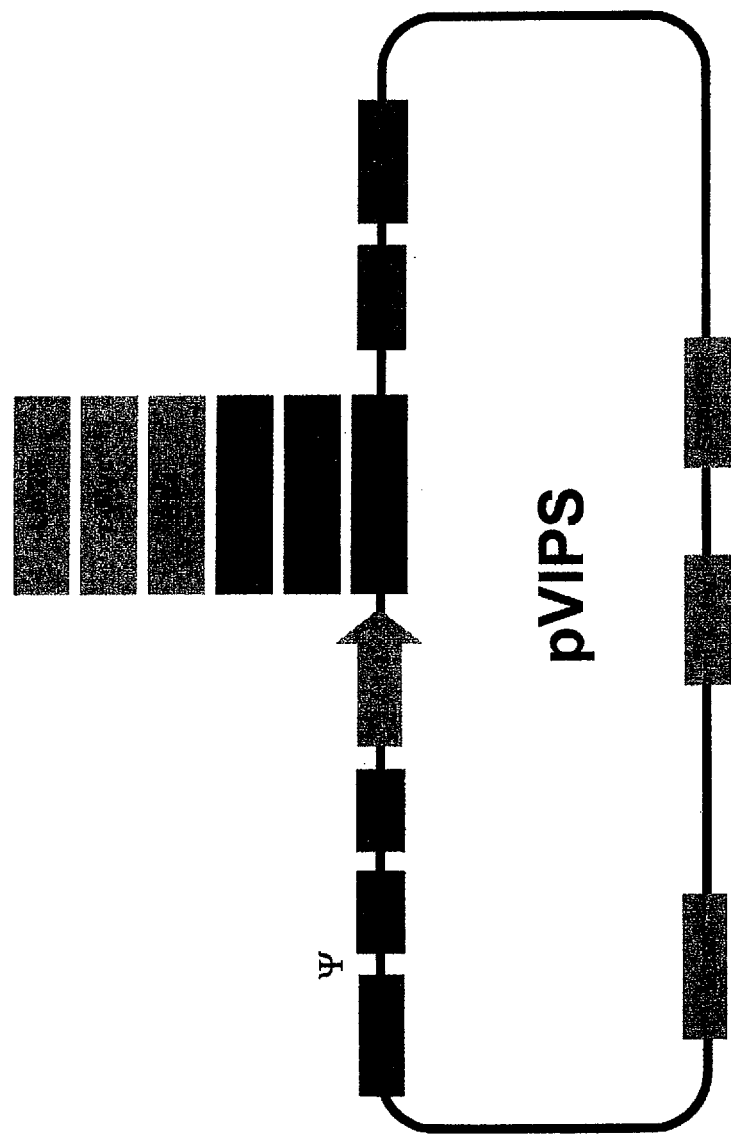
FIG. 20 shows the viPS™ vector kit lentiviral vector which expresses human Oct4 (POU5F1, Sox2, Nanog, Klf4, c-Myc, and Lin28 under control of the human elongation factor-1 alpha promoter (EF1α).

Features of the pVIPS lentiviral vector (see FIG. 20) make it a versatile tool for generating induced pluripotent stem cells (iPSCs) or pluripotent germ cells (iPGCs) include:
  The ability to perform transduction using the replication incompetent lentivirus even on difficult to transduce cell lines
  Expression driven by a RNA Polymerase II EF1α promoter
  Self inactivating (SIN) LTR to ensure minimal secondary recombination to form infectious particles The Following Table 2a Provides a Number of Features of the pVIPS Vector

TABLE 2A

Features of the pVIPS vector

| Vector Element | Utility |
|---|---|
| 5'LTR | 5' long terminal repeat |
| RRE | Rev response element |
| CTS | Central Polypurine tract helps translocation into the nucleus of non-dividing cells |
| EF1α Promoter | RNA Polymerase II promoter |
| WPRE | Enhances the stability and translation of transcripts |
| SIN-LTR | 3' Self inactivating long terminal repeat (Shimada, et al.) |
| SV40 Ori | SV40 On Allows for episomal replication of plasmid in eukaryotic cells |
| pUC Ori | High copy replication and maintenance of plasmid in *E. coli* |
| Amp resistance | Ampicillin (carbenicillin) bacterial selectable marker |

The terms "treat", "treating", and "treatment", etc., as used herein, refer to any action providing or imparting a benefit to a subject at risk for or afflicted by a disease state, condition or deficiency which may be improved using cellular compositions according to the present invention. Treating a condition includes improving the condition through lessening or suppression of at least one symptom, delay in progression of the effects of the disease state or condition, including the prevention or delay in the onset of effects of the disease state or condition, etc. Treatment, as used herein, encompasses both prophylactic and therapeutic treatment and especially includes instilling resistance to disease agents such as Newcastle disease virus or avian (bird) influenza.

The term "differentiation" is used to describe a process wherein an unspecialized ("uncommitted") or less specialized cell acquires the features of a more specialized cell such as, for example, a neural cell, a muscle cell, a cardiomyocyte or other somatic cell. The term "differentiated" includes the process wherein a pluripotent stem cell according to the present invention becomes a more specialized intermediate cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest. Pursuant to the present invention aiPSCs may be used to differentiate into a large number of somatic cells, in the same manner that ESCs may be differentiated. In the case of aiPGCs, these may be used to produce gamete cells after migrating to gonads in an embryo, or alternatively, through differentiation processes to gamete cells.

As used herein, the terms "cell growth medium", "cell propagating medium", "cell transfecting medium", "cell reprogramming medium" and "differentiation medium" are all used to describe a cellular growth medium in which (depending upon the additional components used) the somatic cells, aiPSCs or aiPGCs are grown and/or propagated, transfected and/or reprogrammed or instilled with resistance to a disease agent (e.g. Newcastle disease virus and/or avian influenza). Specific examples of these are presented in the examples section which follows. The somatic cells are generally maintained and/or propagated in a minimum essential medium such as a basic cellular medium (basic salt solution) which includes one or more components such as ascorbic acid, glucose, non-essential amino acids, salts (including trace elements), glutamine, insulin (where indicated and not excluded), and other agents well known in the art and as otherwise described herein. A useful cell growth medium is Dulbecco's modified Eagle's medium (DMEM) with greater than 0.1% bovine serum albumen (Sigma), 5% $CO_2$ at 37° C. For propagation or expansion of cells (generally, more than a million cells), a minimum essential medium with additional components, such as the preferred medium Dulbecco's modified Eagle's medium (DMEM) high glucose (Hyclone) with 10% fetal bovine serum (Hyclone), 4 mM L-glutamine (Gibco) and 50 U/ml penicillin and 50 mg/mL streptomycin (Gibco), 4 ng/ml of basic FGF in 5% $CO_2$ at 37° C. may be used. Alternatively, cells can be expanded in 10% knockout DMEM conditioned by exposure to buffalo rat liver cells for 24 hours, 7.5% fetal bovine serum, 2.5% chicken serum, 1% glutamax, 2% GS nucleoside supplement, 1% antibiotic, 2-mercaptoethanol, 4 ng/ml of basic FGF and 6 ng/ml of stem cell factor. Alternative media may also be used but may not be as effective as the above described media.

Exemplary preferred media for maintaining or expanding somatic cells, in particular, chicken cells is a cell expansion media which is based upon Dulbecco's Modified Eagle's Medium (DMEM) High Glucose (*2): General Range 50%-95%, preferred range of about 80%-90%; more preferably 89% KO-DMEM is used; however minimal essential medium (MEM) is sufficient and these media are further supplemented with Fetal Bovine. Serum (FBS) in the range of 0%-30%, with a preferred range of about 5%-20%. In most instances, about 10% FBS is used to supplement the somatic maintenance/expansion medium. In addition, the following components are often employed: L-glutamine within the general range of about 0.1-15 mM and preferred range of about 1-8 mM; most most about 4 mM L-glutamine is included; and penicillin/streptomycin: within a general range of about 0%-10%, a preferred range of about 0.5%-5% and a more preferred amount of about 1%. Note that the above media are exemplary and modifications of these media may be readily undertaken to maintain and/or expand somatic cells pursuant to the present invention. Many of these media are well-known in the art.

Reprogramming of the somatic cells to aiPSCs or aiPGCs should be done in an enriched culture medium ("reprogramming medium"). A minimum medium is (Dulbecco's modified Eagle medium (DMEM)/F12 (Gibco) or other similar minimum essential medium. In the reprogramming medium, a protein source is required to be added to the medium to assist in the reprogramming of the somatic cells, but the amount of protein required can range from 0.1% to 20%. Additional components such as knockout serum replacer (KSR) may also be preferably included. In addition, preferably, bFGF at effective concentrations (about 5-50 ng/ml) is added as well. A preferred reprogramming medium is [DMEM/F12 (Gibco), supplemented with 20% knockout serum-replacer (KSR; Gibco), 2 mM L-glutamine (Gibco), 0.1 mM nonessential amino acids (Gibco), 50 U/mL penicillin/50 mg/mL streptomycin (Gibco), 0.1 mM b-mercaptoethanol (Sigma-Aldrich), and 10 ng/mL basic fibroblast growth factor (bFGF; Sigma-Aldrich and R&D Systems)]. Other growth factor rich medium which can be used as a reprogramming medium includes a medium such as mTeSR1 medium (from Stemcell Technologies), but the reprogramming media, to be maximally effective must contain some protein source in effective amounts. Media may be pre-conditioned (e.g. 1 day in MEF (inactivated mouse embryonic fibroblasts) before use. An alternative reprogramming medium for production of aiPGCs is cKO medium (KO-DMEM, Invitrogen) containing 4 ng/ml bFGF, 7.5% defined FBS, 2.5% chicken serum (Sigma), 1× Pen/Strep, 1× GlutaMAX (GIBCO), 1× GS nucleoside supplement (Millipore) and 0.1 mM b-mercaptoethanol, with 10% of the KO-DMEM preconditioned in BRL (Buffalo rat liver) cells (ATCC) for 3 days before use.

In the case of avian induced pluripotent germ cells, a preferred media which is employed is a KO-DMEM (knockout dulbecco's minimal essential medium): within a general range of about 50%-90%, a preferred range of about 60%-80%, and a most preferred amount of about 75-80% (especially 75.8%), which includes Basic Fibroblast Growth Factor (bFGF) in a general range of about 0-100 ng/mL, a preferred range of about 2-50 ng/mL; and a more preferred amount of about 4 ng/mL, Fetal Bovine Serum (FBS) within a general range of about 5%-30%, a preferred range of about 6%-20%; and a most preferred amount of about 7.5% of the final medium, Chicken Serum in a general range of 0%-30%, preferred range of about 1%-10% and a most preferred amount of about 2.5%, Penicillin/Streptomycin: General Range 0%-10%, Preferred Range 0.5%-5%; Most Preferred 1%; GlutaMAX within a general range of 0%-15%, a preferred range of about 0.5%-10%, more preferably about 1%, GS Nucleoside Supplement within a general range of 0%-15%, a preferred range of about 0.5%-10% and most preferred about 1%, β-mercaptoethanol within a general range 0-5 mM, preferably within the range of about 0.05-1 mM, most preferably at about 0.1 mM. In addition, in preferred aspects, KO-DMEM preconditioned in buffalo rat liver (BRL) cells or equivalent such as chicken embryonic fibroblast is further added to the medium at a range of about 0%-30%, a preferred range of about 5%-20%, and a most preferred amount of about 10% of the final volume of the media used. It is noted that although a number of other media may be used as described herein, the above media is preferred because it produces high purity aiPGCs, whereas the other media, which can provide aiPGCs, results in the the formation of the pluripotent germ-cells which is not nearly as significant (as high purity) as is produced with the above media.

Induced pluripotent cells are generated and propagated in tissue culture plates. Cells can be in suspension or adherent with or without any additional extracellular matrix or feeder layer. Optimally a matrix like Matrigel or other is used and is adherent to the matrix. Most optimal is use of a mouse embryonic fibroblast feeder layer, although the cells may be grown feeder free.

Cells are propagated to the desired cell number and express Avian pluripotent markers as otherwise described herein. At a minimum, cells should display a high nucleus to cytoplasmic ratio and large nucleoli. Cells should also express alkaline phosphatase and be positive for the periodic acid shift assay. At a higher level of pluripotency of stem cells, the cells should be positive for the pluripotency markers Sox2, Nanog and PouV, possess high levels of telomerase whereas somatic cells are largely negative or low expressers of these genes and markers. Optimally the pluripotent stem cells express the cell surface marker SSEA1.

Differentiation media are well known in the art and comprise at least a minimum essential medium plus one or more optional components such as growth factors, including fibroblast growth factor (FGF), ascorbic acid, glucose, nonessential amino acids, salts (including trace elements), glutamine, insulin (where indicated and not excluded), Activin A, transferrin, beta mercaptoethanol, and other agents well known in the art and as otherwise described herein. Preferred media includes basal cell media which contains between 1% and 20% (preferably, about 2-10%) fetal calf serum, or for defined medium (preferred) an absence of fetal calf serum and KSR, and optionally including bovine serum albumin (about 1-5%, preferably about 2%). Preferred differentiation medium is defined and is serum free.

Other agents which optionally may be added to differentiation medium according to the present invention include, for example, nicotinamide, members of TGF-β family, including TGF-β 1, 2, and 3, Activin A, nodal, serum albumin, members of the fibroblast growth factor (FGF) family, platelet-derived growth factor-AA, and -BB, platelet rich plasma, insulin growth factor (IGF-I, II, LR-IGF), growth differentiation factor (GDF-5, -6, -8, -10, 11), glucagon like peptide-I and II (GLP-I and II), GLP-1 and GLP-2 mimetobody, Exendin-4, parathyroid hormone, insulin, progesterone, aprotinin, hydrocortisone, ethanolamine, epidermal growth factor (EGF), gastrin I and II, copper chelators such as, for example, triethylene pentamine, forskolin, Na-Butyrate, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, Calif.), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, heregulin, or combinations thereof, among a number of other components. Each of these components, when included, are included in effective amounts.

By way of further example, suitable media may be made from the following components, such as, for example, Dulbecco's modified Eagle's medium (DMEM) with high glucose (Hyclone) with 10% fetal bovine serum (Hyclone), 4 mM L-glutamine (Gibco) and 50 U/ml penicillin and 50 mg/ml streptomycin, DMEM/F12 (Gibco), supplemented with 20% knockout serum replacement KSR (Gibco), 2 mM L-glutamine (Gibco), 0.1 mM nonessential amino acids (Gibco), 50 U/ml penicillin/50 mg/ml streptomycin (Giobco), 0.1 mM b-mercaptoethanol (Sigma-Aldrich) and 10 ng/mL basic fibroblast growth factor (bFGF; Sigma Aldrich and R&D systems) as well as the following five (5) media, which utilized Matrigel as the substrate:

1. 20% KSR medium: DMEM/F12 (Gibco), supplemented with 20% knockout serum replacement (KSR; Gibco), 2 mM L-glutamine (Gibco), 0.1 mM nonessential amino acids (Gibco), 50 U/mL penicillin/50 mg/mL streptomycin (Gibco), 0.1 mM b mercaptoethanol (Sigma-Aldrich), and 10 ng/mL basic fibroblast growth factor (bFGF; Sigma-Aldrich and R&D Systems)];

2. TGFβ1/LIF medium: DMEM/F12, supplemented with 20% KSR, 2 mM L-glutamine, 0.1 mM nonessential amino acids, 50 U/mL penicillin/50 mg/mL streptomycin, 0.1 mM b mercaptoethanol, 0.12 ng/ml TGFβ1 (Pepro Tech), 1000 unites/ml LIF(Millipore).

3. LIF/Wnt3a medium: DMEM/F12, supplemented with 20% KSR, 2 mM L-glutamine, 0.1 mM nonessential amino acids, 50 U/mL penicillin/50 mg/mL streptomycin, 0.1 mM b mercaptoethanol, 100 ng/ml Wnt3a (R&D Systems), 1000 unites/ml LIF.

4. 2i/LIF medium: DMEM/F12 supplemented with N2 (Gibco) and mix 1:1 with Neurobasal medium (Gibco) supplemented with B27 (Gibco), 1 mM L-glutamine, 0.8 µM PD0325901(Sigma), 3 µM CHIR99021 (Selleckchem), 20 ng/ml LIF.

5. TGFβ2/activin A/nodal medium: DMEM/F12, supplemented with 20% KSR, 2 mM L-glutamine, 0.1 mM nonessential amino acids, 50 U/mL penicillin/50 mg/mL streptomycin, 0.1 mM b mercaptoethanol, 0.12 ng/ml TGFβ1 (Pepro Tech), 10 ng/ml Activin A (R& D Systems), 500 ng/ml mouse recombinant nodal (R & D systems).

An alternative medium growing/culturing aiPSCs and for differentiating aiPSCs in the present invention (depending upon the components which are used) is DMEM/F12 (50:50) which contains about 2% proalbumin (albumin; Millipore/Serologicals), 1× Pen/Strep, 1×NEAA, 1× Trace Elements A,B, C (Mediatech), Ascorbic Acid (10-100 ng/ml, about 25-65 ng/ml, about 50 ng/ml), about 0.1 mM (0.025-0.5 mM) β-Mercaptoethanol (Gibco), about 2-10 ng/ml, about 5-9 ng/ml, about 8 ng/ml bFGF (Sigma), with additional components added depending upon the cells to which the aiPSCs are to be differentiated.

Each of the above-media may also be used to provide aiPSGCs, however, the efficiency of production and relative purity are not as significant as occurs with the use of the preferred media, described in detail hereinabove.

Various media which are useful in the present invention include commercially available media available from and can be supplemented with commercially available components, available from Invitrogen Corp. (GIBCO), Cell Applications, Inc. and Biological Industries, Beth HaEmek, Israel, among numerous other commercial sources, including Calbiochem. In preferred embodiments at least one differentiation agent such as fibroblast growth factor (FGF), LR-IGF (an analogue of insulin-like growth factor), Heregulin and optionally, VEGF (preferably all three in effective amounts) is added to the cell media in which a PSC is cultured and differentiated into a mature differentiated cell line. One of ordinary skill in the art will be able to readily modify the cell media to produce any one or more of the target cells pursuant to the present invention. Cell differentiation medium is essentially synonymous with basal cell medium but is used within the context of a differentiation process and includes cell differentiation agents to differentiate cells into other cells. Growth/stabilizing medium is a basal cell medium which is used either before or after a reprogramming or differentiation step in order to stabilize a cell line for further use. Growth/stabilizing media refers to media in which a pluripotent or other cell line is grown or cultured prior to differentiation. In general, as used herein, the various cell media which are used may include essentially similar components of a basal cell medium, but are used within different contexts and may include slightly different components in order to effect the intended result of the use of the medium. In the case of a reprogramming medium, the inclusion of a protein in an effective amount is highly important.

As discussed, pluripotent stem and germ cells may be cultured (preferably) on a layer of feeder cells that support the pluripotent stem cells in various ways which are described in the art. Alternatively, pluripotent stem cells may also be cultured in a culture system that is essentially free of feeder cells, but nonetheless supports proliferation of pluripotent stem cells. The growth of pluripotent stem and germ cells in feeder-free culture without differentiation is often supported using a medium conditioned by culturing previously with another cell type. Alternatively, the growth of pluripotent stem cells in feeder-free culture without differentiation may be supported using a chemically defined medium. These approaches are well known in the art. In preferred aspects of the present invention, the cells are grown in the presence of feeder cells.

Approaches for culturing cells on a layer of feeder cells are well known in the art. For example, Reubinoff et al. (*Nature Biotechnology* 18: 399-404 (2000)) and Thompson et al. (*Science* 6 Nov. 1998: Vol. 282. no. 5391, pp. 1145-1147) disclose the culture of pluripotent stem cell lines from human blastocysts using a mouse embryonic fibroblast feeder cell layer, the teachings of which may be adapted for use in the present invention for aiPSCs and aiPGCs. Approaches for culturing PSCs in media, especially feeder-free media, are well known in the art and may be readily adapted for use in the present invention. U.S. Pat. No. 6,642,048 discloses media that support the growth of pluripotent stem (pPS) cells in feeder-free culture, and cell lines useful for production of such media, which can be readily adapted for use in the present invention. In another example, US20070010011 discloses a chemically defined culture medium for the maintenance of pluripotent stem cells, also adaptable for use in the present invention.

As discussed above, the cells, especially including the aiPSCs and aiPGCs may be grown on a cellular support or matrix, as adherent monolayers, rather than as embryoid bodies or in suspension. In the present invention, the use of Matrigel as a cellular support is preferred. Cellular supports preferably comprise at least one reprogramming or substrate protein. The term "reprogramming protein" or "substrate protein" is used to describe a protein, including a matrix protein, which is used to grow and/or propagate cells and/or to promote reprogramming of a somatic cell into a pluripotent stem cell. Reprogramming proteins which may be used in the present invention include, for example, an extracellular matrix protein, which is a protein found in the extracellular matrix, such as laminin, tenascin, thrombospondin, and mixtures thereof, which exhibit growth promoting and contain domains with homology to epidermal growth factor (EGF) and exhibit growth promoting and differentiation activity. Other reprogramming proteins which may be used in the present invention include for example, collagen, fibronectin, vibronectin, polylysine, polyornithine and mixtures thereof. In addition, gels and other materials such as methylcellulose of other gels which contain effective concentrations of one or more of these reprogramming proteins may also be used. Exemplary reprogramming proteins or materials which include proteins which may be used to reprogram cells include, for example, BD Cell-Tak™ Cell and Tissue Adhesive, BD™ FIBROGEN Human Recombinant Collagen I, BD™ FIBROGEN Human Recombinant Collagen III, BD Matrigel™ Basement Membrane Matrix, BD Matrigel™ Basement Membrane Matrix High Concentration (HC), Growth Factor Reduced (GFR) BD Matrigel™, BD™. PuraMatrix™ Peptide Hydrogel, Collagen I, Collagen I High Concentration (HC), Collagen II (Bovine), Collagen III, Collagen IV, Collagen V, and Collagen VI, among others. The preferred material for use in the present invention includes Matrigel™.

Another composition/material which contains one or more proteins for use in reprogramming is BD Matrigel™ Basement Membrane Matrix. This is a solubilized basement membrane preparation extracted from the Engelbreth-Holm-Swarm (EHS) mouse sarcoma, a tumor rich in ECM proteins. Its major component is laminin, followed by collagen IV, heparan sulfate, proteoglycans, entactin and nidogen.

The induced pluripotent stem and germ cells are generated and propagated in tissue culture plates. Cells can be in suspension or adherent with or without any additional extracellular matrix (e.g. Matrigel or other matrix protein as described above) or feeder layer. Preferably, a matrix like Matrigel or other as described above is used and is adherent to the matrix. In preferred aspects, use is made (in all instances, but preferably during reprogramming and/or propagation) of a mouse embryonic fibroblast feeder layer. The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Cells are reprogrammed and propagated to the desired cell number and express avian pluripotent biomarkers. At a minimum, cells should display a high nucleus to cytoplasmic ratio and large nucleoli. Cells should also express alkaline phosphatase and be positive for the periodic acid shift assay. At a higher level of pluripotency, aiPSCs should be positive for the pluripotency markers Sox2, Nanog and PouV, possess high levels of telomerase whereas somatic cells are largely negative or low expressers of these genes and markers. Optimally pluripotent cells express the cell surface marker SSEA1. In the case of aiPGCs, the cells are generally positive for the biomarkers OCT4 (PouV), AP, PAS, SSEA1, EMA1, Nanog, DAZL, CVH, CXCR4 and C-KIT.

aiPSCs and aiPGCs which are produced according to the present invention can be selected for certain in vitro traits such as expression of an added exogenous gene (transgene) or loss of a endogenous trait (knockout) which may be considered for the production of transgenic animals or a new trait such as resistance to cell death when exposed to a virus such as Newcastle virus as described in detail herein. A method of instilling resistance to a disease agent such as Newcastle disease virus or avian influenza represent an additional embodiment according to the present invention.

At any time the propagated reprogrammed cells can be re-exposed (reprogrammed) to reprogramming gene expression (DNA integrating or non integrating transient expression) and selected again for pluripotent traits as described above, including optimally SSEA1 expression.

As used herein, the term "activate" refers to an increase in expression or upregulation of a marker such as or an upregulation of the activity of a marker associated with aiPSC or aiPGC, a chimeric cell or a differentiated cell including a neuron, muscle cell or a related cell as otherwise described herein (e.g., nanog, SSEA1, etc.). The term "deactivate" generally refers to a decrease in expression or down regulation of the activity of a marker associated with a cell.

As used herein, the term "isolated" when referring to a cell, cell line, cell culture or population of cells, refers to being substantially separated from the natural source of the cells such that the cell, cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers. In the present invention, in aspects related to isolating full reprogrammed cells from non-fully reprogrammed cells, magnetic and florescence cell sorting have been found to significantly improve upon the ability to isolate fully reprogrammed selectively. Isolated cells typically express higher levels of pluripotency markers and behave more like pluripotent stem cells with respect to expandability.

As used herein, the term "express" refers to the transcription of a polynucleotide or translation of a polypeptide (including a marker) in or on the surface of a cell, such that levels of the molecule are measurably higher in or on a cell that expresses the molecule than they are in a cell that does not express the molecule. Methods to measure the expression of a molecule are well known to those of ordinary skill in the art, and include without limitation, Northern blotting, RT-PCT, in situ hybridization, Western blotting, and immunostaining.

As used herein, the term "markers" or "biomarkers" describe nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

As used herein, the term "contacting" or "exposing" (i.e., contacting or exposing a cell with a vector, compound or disease agent, among others) is intended to include incubating the compound and the cell together in vitro (e.g., adding the vector or compound to cells in culture). The step of contacting the cell with reprogramming or differentiation medium and one or more growth proteins or other components such as reprogramming vectors as otherwise described herein can be conducted in any suitable manner. For example, the cells may be treated in adherent culture as an adherent layer, as embryoid bodies or in suspension culture, although the use of adherent layers may be preferred because they provide an efficient process oftentimes providing reprogramming to a target cell population of high relative purity (e.g. at least 50%, 60%, 70-75%, 80% or more). It is understood that the cells contacted with the reprogramming or differentiation agent may be further treated with other cell differentiation environments to stabilize the cells, or to differentiate the cells further.

As used herein, the term "differentiation agent" refers to any compound or molecule that induces a cell such as an aiPSC or aiPGC or other cell to partially or terminally differentiate. The term "differentiation agent" as used herein includes within its scope a natural or synthetic molecule or molecules which exhibit(s) similar biological activity.

The term "effective" is used to describe an amount of a component, compound or composition which is used or is included in context in an amount and/or for a period of time (including sequential times) sufficient to produce an intended effect. By way of example, an effective amount of a differentiation agent is that amount which, in combination with other components, in a differentiation medium for an appropriate period of time (including sequential times when different differentiation agents are exposed to cells to be differentiated) will produce the differentiated cells desired.

Relevant Uses of the Present Invention

Agriculture/Veterinary:

The present invention is broadly applicable given that the avian species are a widely used developmental research and agricultural species, but gene targeting studies have been limited given an absence of robust pluripotent stem cells that can serve as a vector for these changes. Birds supply about 25-30% of the animal protein consumed in the world. Recent publications in Science and PLoS One have highlighted a number of gene based strategies (siRNA, DNA and recombinant protein) to prevent the spread of Avian Influenza (4-6). Genetically distinct disease resistant birds would in theory not require vaccination and offer the people of underdeveloped and developed countries alike animals that require reduced veterinary care and increased food source safety. However, these significant advances have several short comings that can be potentially overcome using avian induced pluripotent stem cells including:

1) the need to continually use DNA or recombinant protein vaccination of birds which is not economically or logistically possible in many of the poorest villages in southeast Asia or Africa, which makes up the majority of the farming population in these countries;

2) the ability to generate birds that carry resistant genes and transfer resistance to offspring is limited;

3) the restricted ability to generate animals with multiple genetic modifications to create disease resistance at multiple viral stages or to even more than one disease.

Utilizing avian stem cells that can be genetically manipulated, clonally isolated, easily expanded over numerous passages and can form chimeric animals, can overcome these major challenges and provide an economically advantageous approach to advantageous phenotypic modification of the animal.

aiPGCs may be used to produce gametes for fertilization efforts for birds for agricultural production or in instances where a species is endangered. The use of these cells in promoting agricultural efficiency and in enhancing a population of endangered bird species or otherwise producing particular birds where such a need arises. In addition, these cells may be used to do further genetic modification to the cells to incorporate genes for knockout models or for incorporating genes for animals studies in drug development.

Research Biomedical Applications:

Avian embryonic models have a long history of providing critical new insights into developmental biology including organ function (13, 14), disease progression (e.g. Pompe disease) (15), eye disorders (16, 17) and many others (18, 19). The advantage that avian species have is their relative size and ease of access to the embryo for manipulation. Cells and tissues including whole sections of the spinal column can be transplanted into the avian embryo and can be monitored in real time during development (20). This is not possible in mammalian species. Moreover, the quail-chicken chimera is an attractive and widely used model for developmental patterning and cell fate studies given that cells can be readily tracked in this model (21, 22). The quail also has a short generation interval (3-4 generation per year)(23), facilitating genetic selection studies and experiments requiring multiple generational observations (24). Coupling a robust and clonal feeder free iPSC lines and derived committed cell lines or tissues with these model systems offers new opportunities to manipulate and study developmental process both in vitro and in vivo.

Vaccines:

For decades, vaccines have provided effective protection from influenza for Americans. While they have traditionally been produced in chicken eggs, a new technology-cell-based vaccine production-could save hundreds of thousands of lives in the event of an outbreak of pandemic influenza, or some other infectious disease.

A new approach would use avian iPSC to grow the influenza viruses. Cell-based vaccine production could more easily meet "surge capacity needs" because iPSCs could be frozen and stored in advance of an epidemic or developed rapidly in response to an epidemic. Cell-based vaccine production dramatically reduces the possibility for contamination and promises to be more reliable, flexible, and expandable than egg-based methods. In place of eggs, cell-based vaccine production utilizes avian iPSC cell lines that are capable of hosting a growing virus in bioprocessing cell culture vessels. The virus is introduced into the cells where it multiplies to produce a large amount of virus per iPSC. Generally the cells' outer walls are removed, harvested, purified, and inactivated. A vaccine can be produced in a matter of weeks. While other cell lines are capable of generating a vaccine. The avian iPSC will produce high concentrations and thus be more economical and faster than mammalian cell lines.

Examples/Results

Quail Pluripotent Stem Cells qiPSCs Display Morphological Characteristics Consistent with a Pluripotent Cell Type The generation of qiPSCs was initiated by testing the lentiviral transduction efficiency of isolated (QEF) (FIG. 1A) with an eGFP reporter construct using both GeneJammer and TransDux transduction reagents. A 20 MOI transduction with Transdux resulted in the highest efficiency with 40.5% (GFP) positive cells (S. FIG. 1). QEFs were then transduced with the six human pluripotency genes hPOU5F1, hNANOG, hSOX2, hLIN28, hC-MYC and hKLF4 driven by the elongation factor 1-alpha (EF1-α) promoter with each construct in individual lentiviral vectors. After 24 hrs, cells were replated on feeder cells in stem cell expansion medium.

Colonies were observed beginning 6 days after transduction with irregular shaped borders and fibroblast-like cell morphology (FIG. 1B). These initial colonies failed to proliferate and expand indicating that these colonies were not fully reprogrammed. Potential qiPSCs were observed around 17 days after transduction and grew as compact colonies (FIG. 1C). The compact colonies were mechanically picked and initially replated on feeder plates in stem cell expansion medium. However, replated cells failed to proliferate and appeared apoptotic. Additional colonies were collected and replated on matrigel coated plates in mTeSR1 stem cell medium. This system supported the growth and expansion of colonies and subsequent qiPSC expansion was performed using this system.

Figure 2:
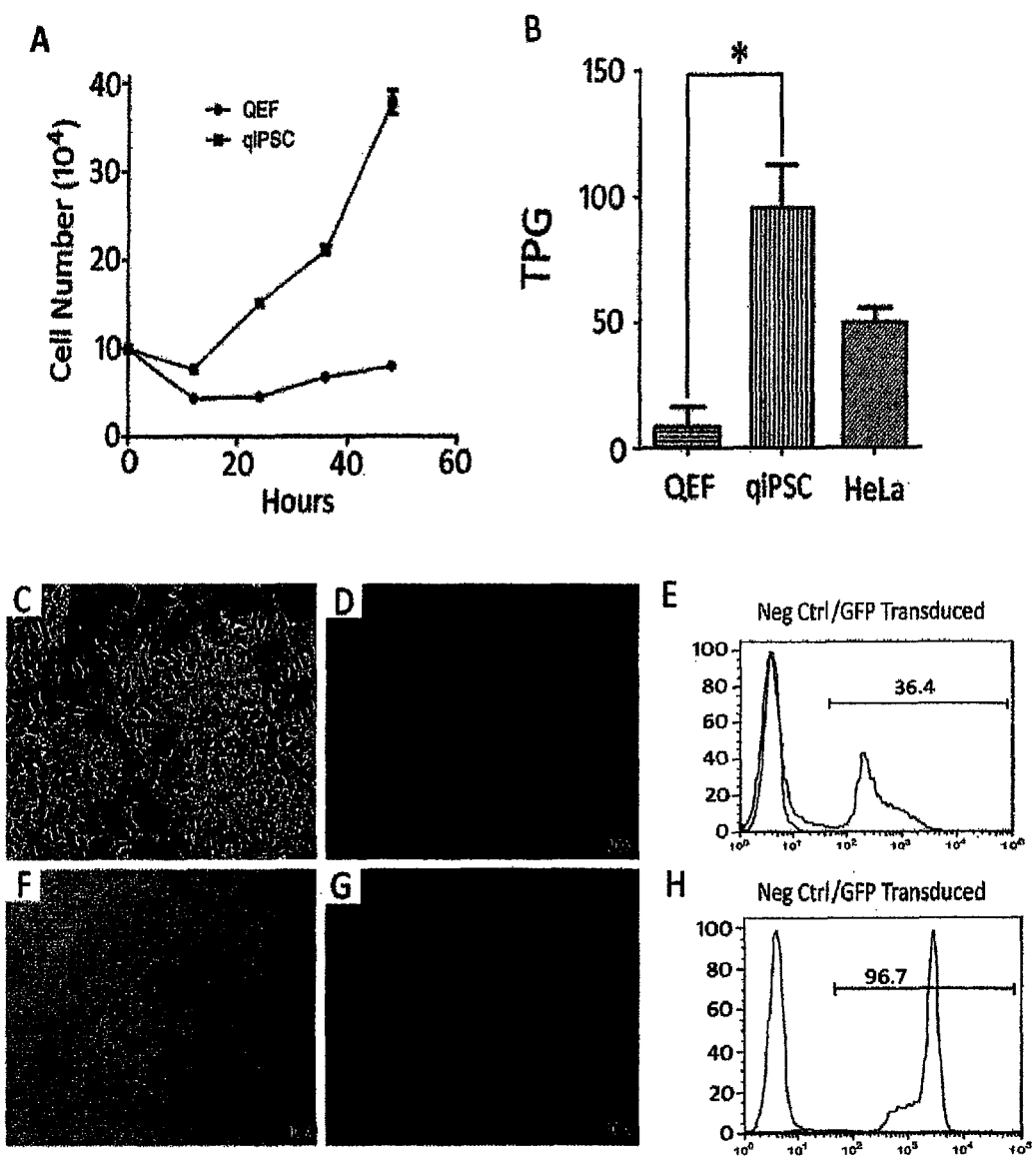
FIG. 2 shows qiPSCs demonstrate rapid proliferation, high levels of telomerase activity and clonal expansion after genetic manipulation. qiPSCs doubling time was 16.6 hr (n=3), significantly faster than the QEF cells (36.9 hr; $P<0.01$) (A). Telomerase activity in qiPSC was higher than QEF (>11 fold, *$P<0.01$) and comparable to HeLa cells (P=0.07) (B). 8 days post transduction a subpopulation qiPSC expressed green fluorescent protein (GFP). (C, D, E). After 9 days post-fluorescence activated cell sorting (FACS), clonally expanded GFP+ qiPSCs generated colonies (F, G) that have maintained GFP expression long term (H).

Morphologically, qiPSC colonies were highly refractive and at the single cell level showed clear cell boarders, high nuclear to cytoplasm ratio and prominent nucleoli (FIG. 1D, 1E). qiPSCs were strongly positive for alkaline phosphatase (AP) and periodic acid Schiff staining (PAS; FIG. 1F, 1G). PCR and RT-PCR using human specific primers revealed that 5 out of 6 pluripotent stem cell factors, hPOU5F1, hSOX2, hNANOG, hLIN28 and hC-MYC, were integrated and expressed in qiPSCs, while hKLF4 was not present (FIG. 1H).

qiPSCs are Highly Proliferative, Express Pluripotent Marks and are Capable of Clonal Expansion after Genetic Manipulation Rapid proliferation and high levels of telomerase activity are hallmarks of pluripotent stem cells. To determine the doubling time, plated cells were quantified every 12 hours for 48 hr. The population doubling time of qiPSCs was 16.6 hr, much faster than the QEF parent cell line (36.9 hr, $P<0.01$) (FIG. 2A). qiPSCs are highly proliferative and are passaged every 4 days. Cells have been maintained for more than 50 passages without loss of the pluripotent phenotype. Telomerase activity revealed a significant ($P<0.01$) increase of >11 fold from 8.4 total product generated (TPG) in QEFs to 95.3 TPG in qiPSCs (FIG. 2B). Telomerase activity of qiPSCs was comparable to that of positive control HeLa cell line (50.8 TPG, $P=0.07$), which indicates the immortality of qiPSCs. Moreover, these cells were capable of clonal expansion after genetic manipulation. qiPSCs were transduced with the eGFP gene resulting in a 36.1% GFP+ population (FIG. 2C-E). Single GFP+ cells were FACS sorted into each well of a 96-well plate and colonies were found in 2 wells 9 days after sorting (FIG. 2F, 2G). Flow cytometry analysis of cells expanded from one colony showed that >96% of the cells still expressed GFP after serial subculture (FIG. 2H).

Figure 3:
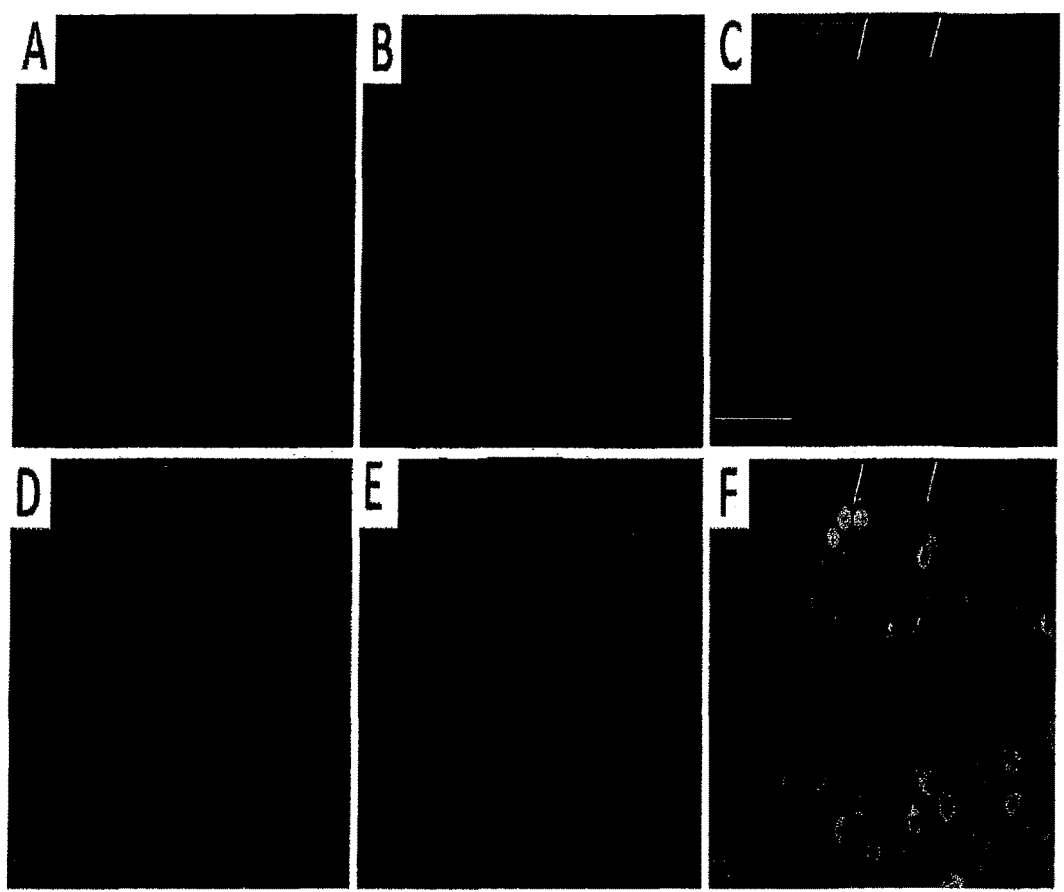
FIG. 3 shows qiPSCs express pluripotent genes. Immunocytochemistry demonstrated that QEFs were negative for POU5F1 (A) and SOX2 (B), while qiPSCs were POU5F1 (D) and SOX2 (E) positive. Scale bars are 50 µm.

Immunocytochemistry revealed that POU5F1 and SOX2 proteins were absent in QEFs (FIG. 3A, 3B, 3C), but positive in qiPSCs (FIG. 3D, 3E, 3F). Immunocytochemistry of qiPSCs showed cells were negative for the pluripotency markers SSEA4, TRA-1-81 or TRA-1-60 (data not show).

Embryoid Body Differentiation of qiPSC Results in the Formation 3 Germ Layers

Figure 4:
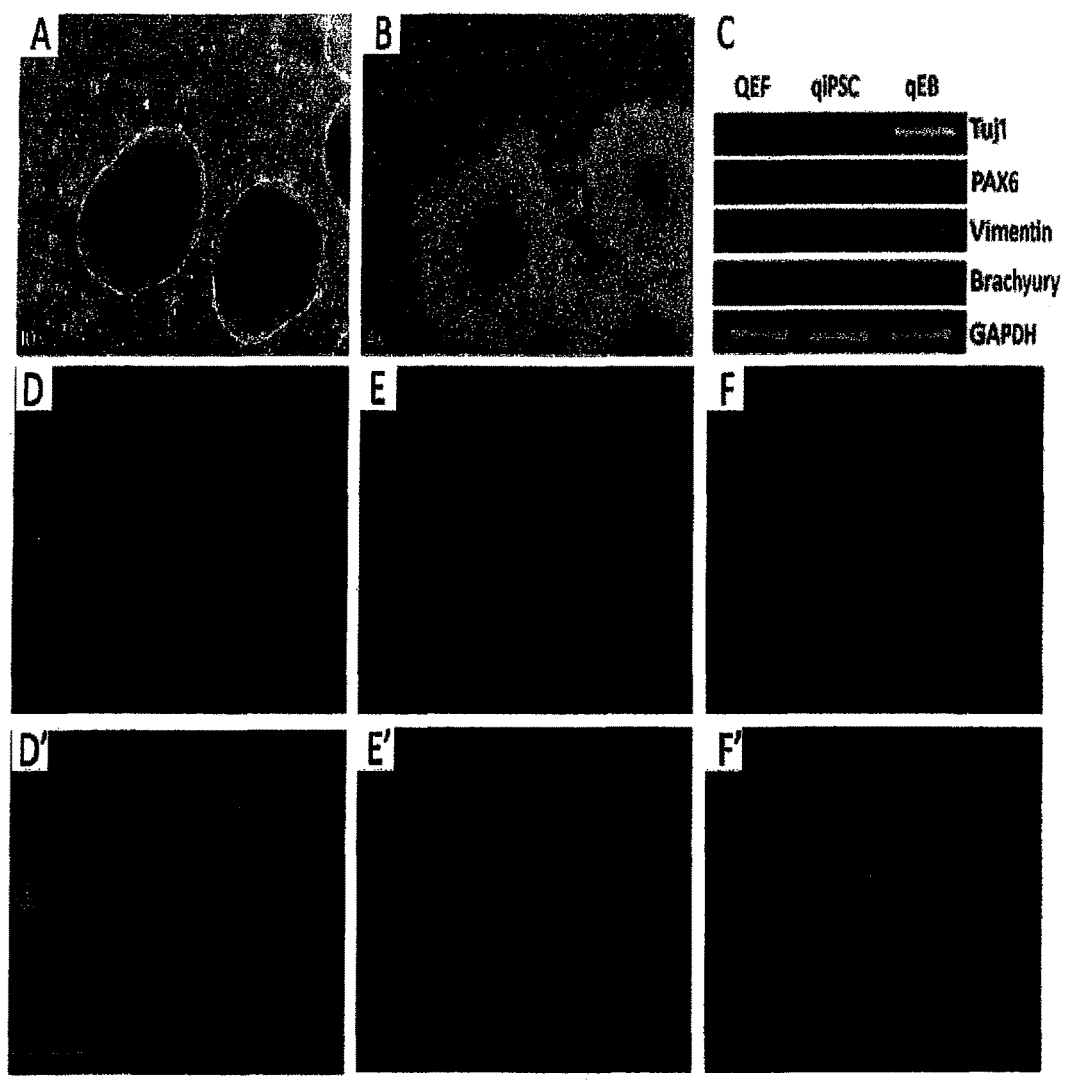
FIG. 4 shows that qiPSCs generate EBs that form all 3 germ layers. Compact EBs were formed after culture for 6 days (A). EBs were replated for further differentiation for 2 days (B). Ectoderm (TUJ1, PAX6), endoderm (Vimentin) and mesoderm (*Brachyury*) genes were expressed in EBs (C). Immunocytochemistry demonstrated that EB derived cells were positive for ectoderm (TUJ1, D), endoderm (SOX17, E) and mesoderm (αSMA, F) proteins. Scale bars are 50 µm.

To derive embryoid bodies (EBs), qiPSCs were plated in AggreWell plates for 24 hrs and then transferred to suspension culture in mTeSR1 medium for differentiation. Six days of suspension culture resulted in round and compact EBs from qiPSCs (FIG. 4A). EBs were collected for RNA isolation and RT-PCR or replated for additional differentiation for 2 days in stem cell expansion medium without bFGF the removal of which will enable differentiation (FIG. 4B). Results of RT-PCR showed expression of TUJ1 (ectoderm), PAX6 (ectoderm), Vimentin (endoderm) and Brychyury (mesoderm) in EBs, but not in qiPSCs or QEF cells (FIG. 4C). Immunocytochemistry showed cells positive for TUJ1 (ectoderm, FIG. 4D), SOX17 (endoderm, FIG. 4E) and alpha smooth muscle actin (αSMA, mesoderm, FIG. 4F) in plated EBs. These results indicated that qiPSCs could differentiate into various cell types from all three germ layers.

qiPSC Differentiate In Vitro into Neuronal, Astrocytes and Oligodendrocytes

Figure 5:
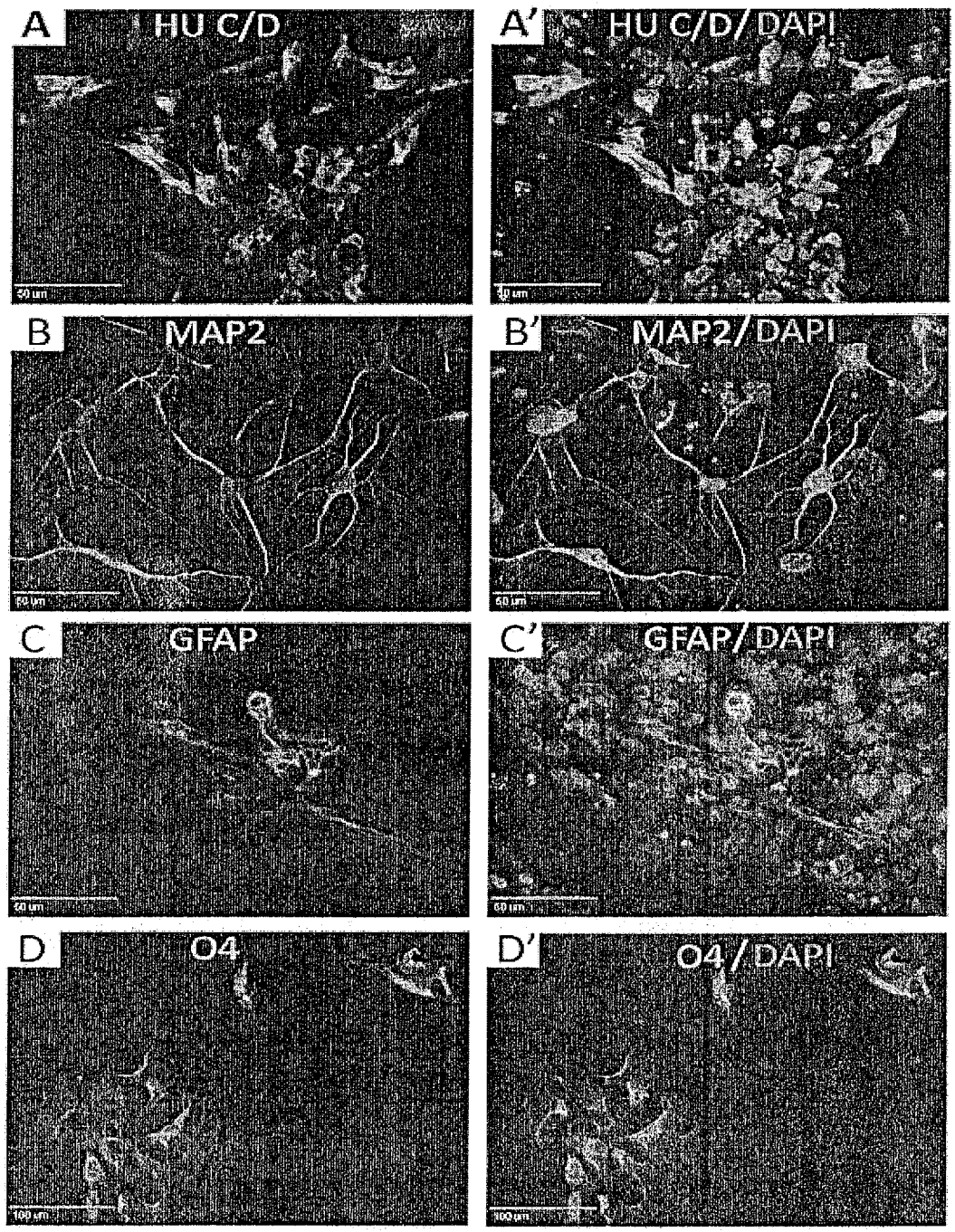
FIG. 5 shows directed differentiation of qiPSCs to 3 neural lineages. qiPSCs were subjected to a 3 step neural differentiation process, with cells first cultured in neural derivation medium for 12 days, then in proliferation medium for 7 days, followed by continual maintenance in differentiation medium. Neurite extensions could be found after culture in differentiation medium for 48 days. Neuron-like cells expressing Hu C/D+ (A) and MAP2 (B) were present after 10 days of differentiation and astrocytes (C) and oligodendrocyte (D) like cells after 23 and 39 days of differentiation respectively. Scale bars in E, F and G are 50 µm. Scale bars in H are 100 µm.

To derive neural cells, qiPSCs were subjected to a 3 step neural differentiation process. Cells were initially cultured in neural derivation medium for 12 days, proliferation medium for 7 days and differentiation medium continuously. Immunostaining showed that these cells were positive for neural proteins Hu C/D+ and MAP2+(FIGS. 5A, 5B) after 10 days of differentiation. A significant number of neurite extensions were observed after differentiation. Differentiated qiPSCs were found to be positive for the astrocyte and oligodendrocyte associated proteins GFAP and O4 after 23 and 39 days of differentiation, respectively, in neural differentiation medium (FIG. 5C, 5D). These data demonstrated the neural competence of qiPSC and differentiation into all 3 neural lineages, which is not seen in any previous avian stem cell lines.

Incorporation of qiPSCs into Chimeric Embryo and Live Offspring

Figure 6:
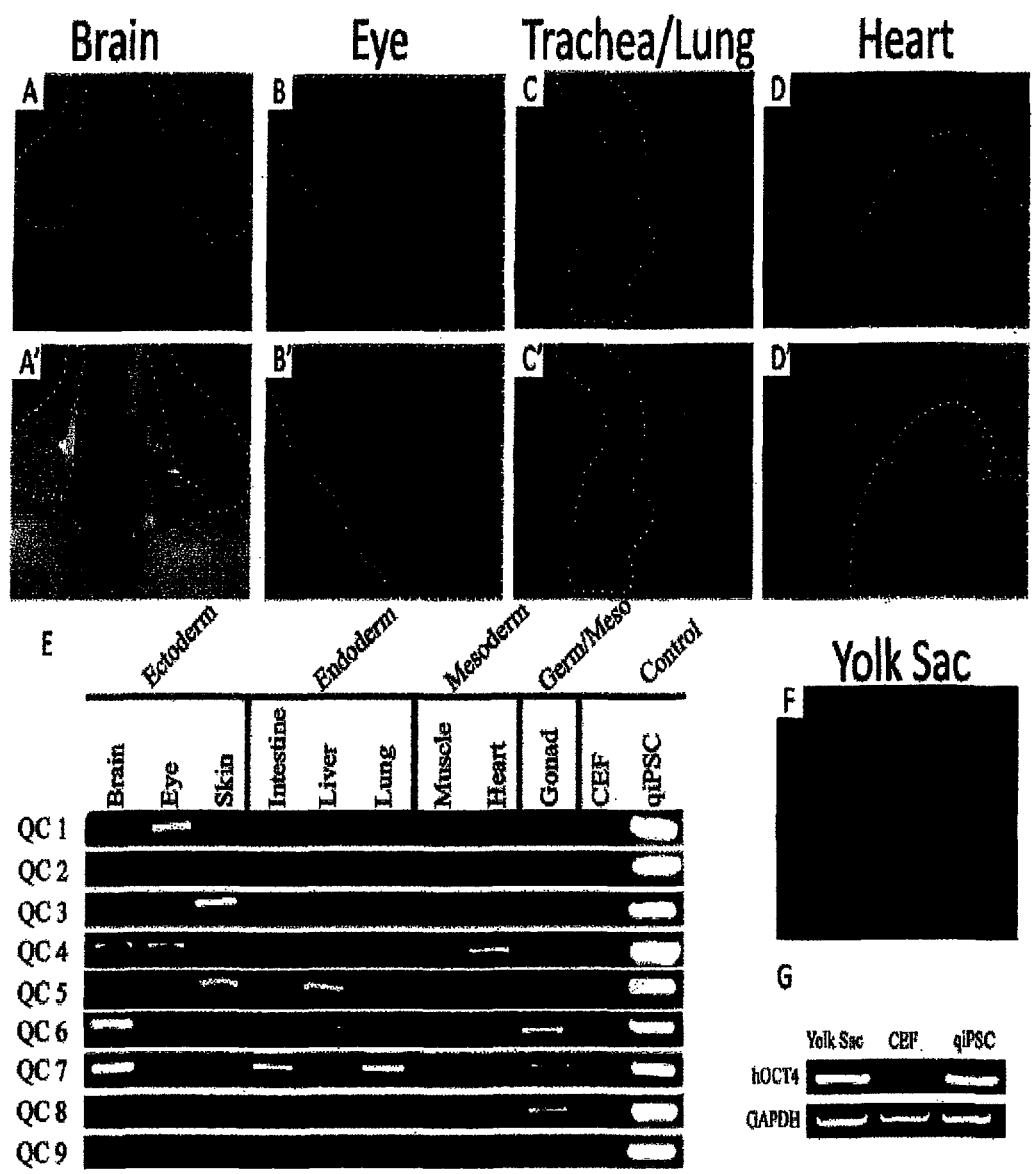
FIG. 6 shows chimeric chicken embryos derived from qiPSC. GFP+ qiPSCs were incorporated in brain (A, ectoderm), eye (B, ectoderm), trachea/lung (C, endoderm), heart (D, mesoderm) and yolksac (F, extraembryonic tissue) of quail-chicken chimeric embryos. PCR results demonstrated that various tissues were positive for the hPOU5F1 transgene (E, G).
Figure 9:
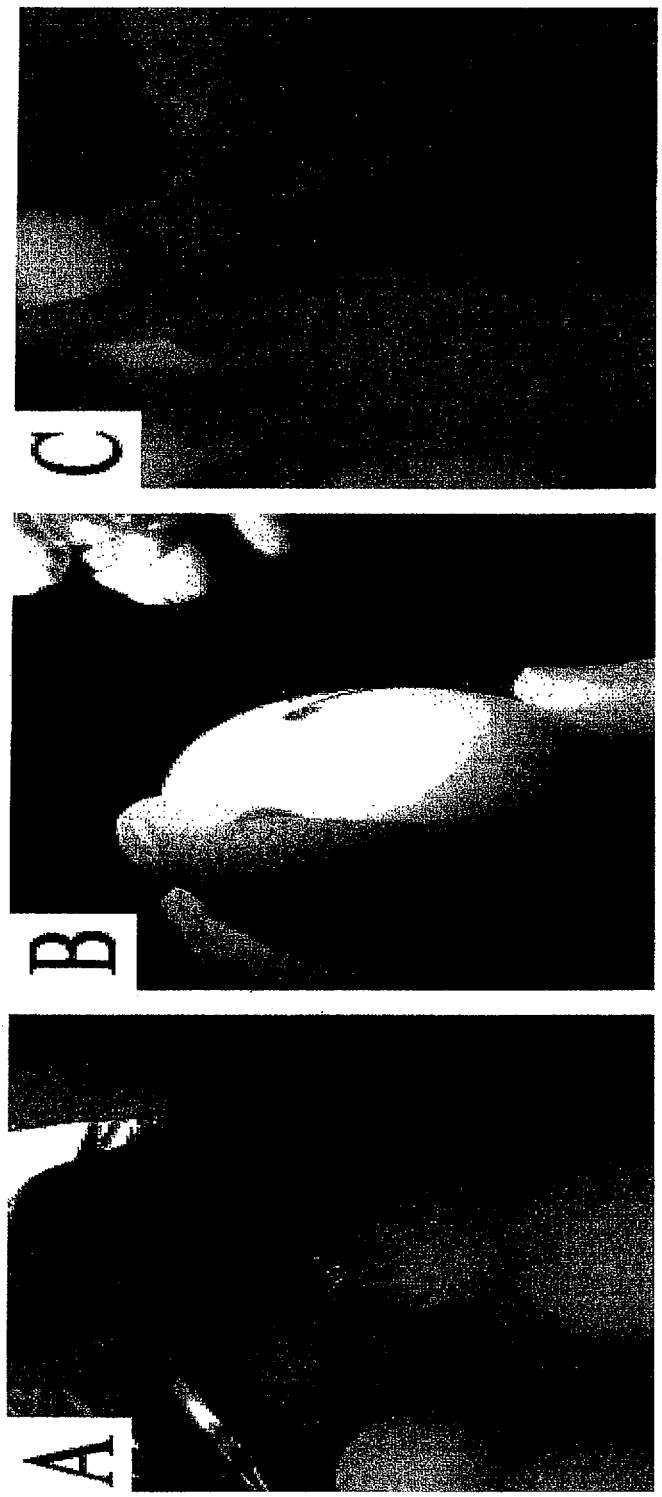
FIG. 9 shows the injection of qiPSC into stage X chicken embryo. To inject qiPSCs into chicken embryos, a single window was drilled into the shell of stage X White Leghorn chicken egg (A). qiPSC were then injected into the subgerminal cavity with a micropipette (B). Windows were sealed with hot glue and injected eggs were then transferred to incubators (C).
Figure 10:
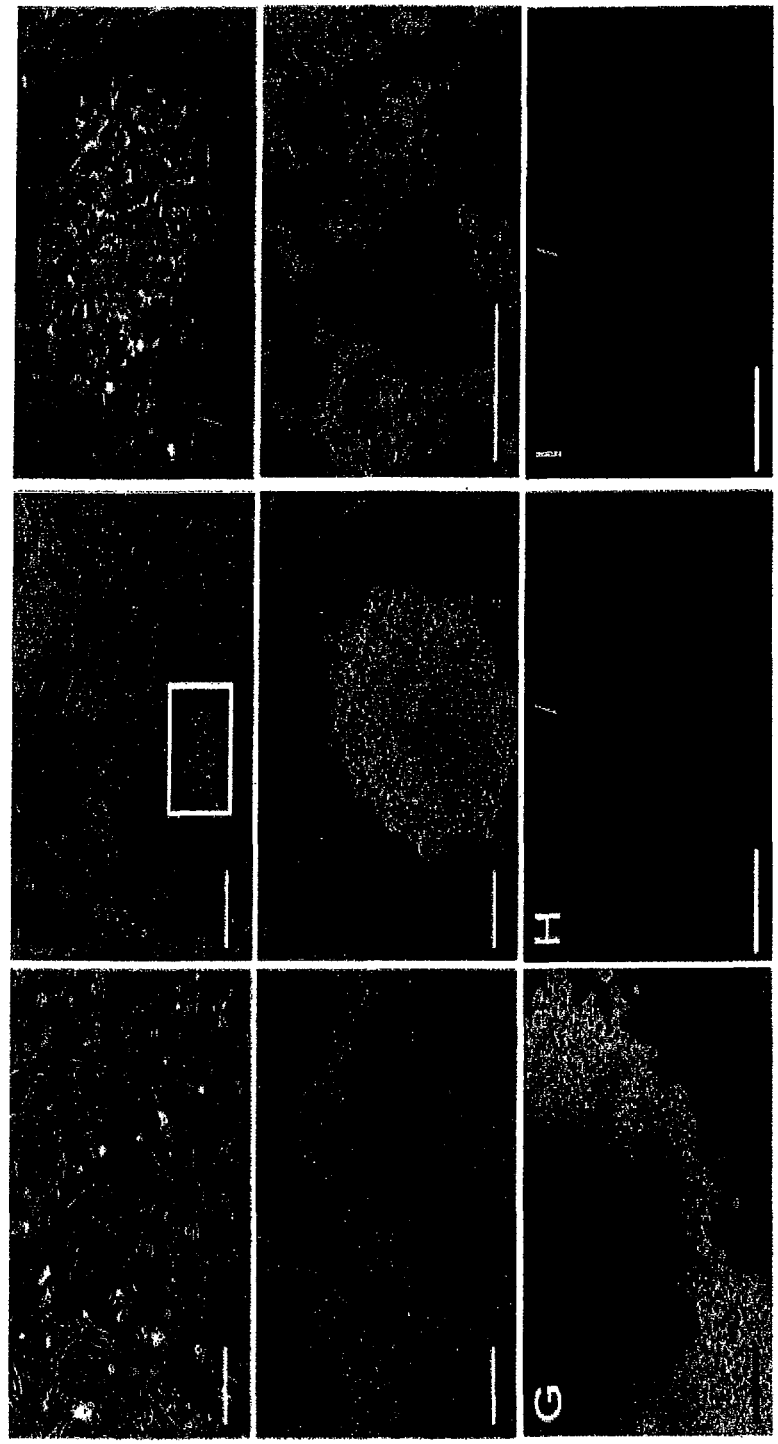
FIG. 10 shows the derivation of ciPSCs. Chicken embryonic fibroblasts (CEFs) were transduced with lentiviral vectors containing human stem cell factor (A) and then replated onto MEF feeder. Colonies of reprogrammed CEFs were observed at day 5 (B) and an enlarged view of the typical ciPSC-like colony demonstrating stem cell morphology (C). The reprogrammed cells were around 50% confluent at day 7 after transduction and subjected to serial passages (D) and finally plated on Matrigel coated plates (E). The ciPSCs were positive for Alkaline Phosphotase (F) and Periodic Acid Schiff's Staining (G) were also positive for pluripotent markers SSEA1 (H) and germ cell marker DDX4 (I) in immunostaining.

To generate qiPSC-chicken chimeras, GFP+ qiPSCs at passage 26 were injected into the subgerminal cavity of stage X embryos (FIG. 10). Embryos were incubated for 14 or 19 days and were then dissected to determine GFP+ qiPSC incorporation into embryos. GFP+ qiPSCs were incorporated in brain (FIG. 6A), eye (FIG. 6B), trachea/lung (FIG. 6C), heart (FIG. 6D) and yolk sac (FIG. 6F) tissues. PCR was performed for the human POU5F1 gene used to reprogram QEFs into iPSCs to further determine qiPSC contribution in chimeric animals. qiPSCs were present in tissues from the ectoderm (brain, eye and skin), endoderm (intestine, liver and lung), mesoderm (muscle and heart), extraembryonic tissue (yolk sac) and the gonad (FIGS. 6E and 6G, FIG. 9). PCR products from qiPSCs from the yolk sac and skin were sequenced to validate that PCR primers were solely expanding the human POU5F1 sequence. Blast of the sequenced DNA amplified from these tissues showed identity of 99% to 100% for human POU5F1 genomic context sequence NC_000006.11, but only 72% to 74% maximum identity for chicken PouV(Oct4 homologue) mRNA NM_001110178.1 and no significant similarity to its genomic context sequence NW_001471503.1. These results indicate that qiPSCs incorporated and contributed to chicken embryonic tissues from all 3 germ layers, extraembryonic tissues and potentially the germline.

Figure 7:
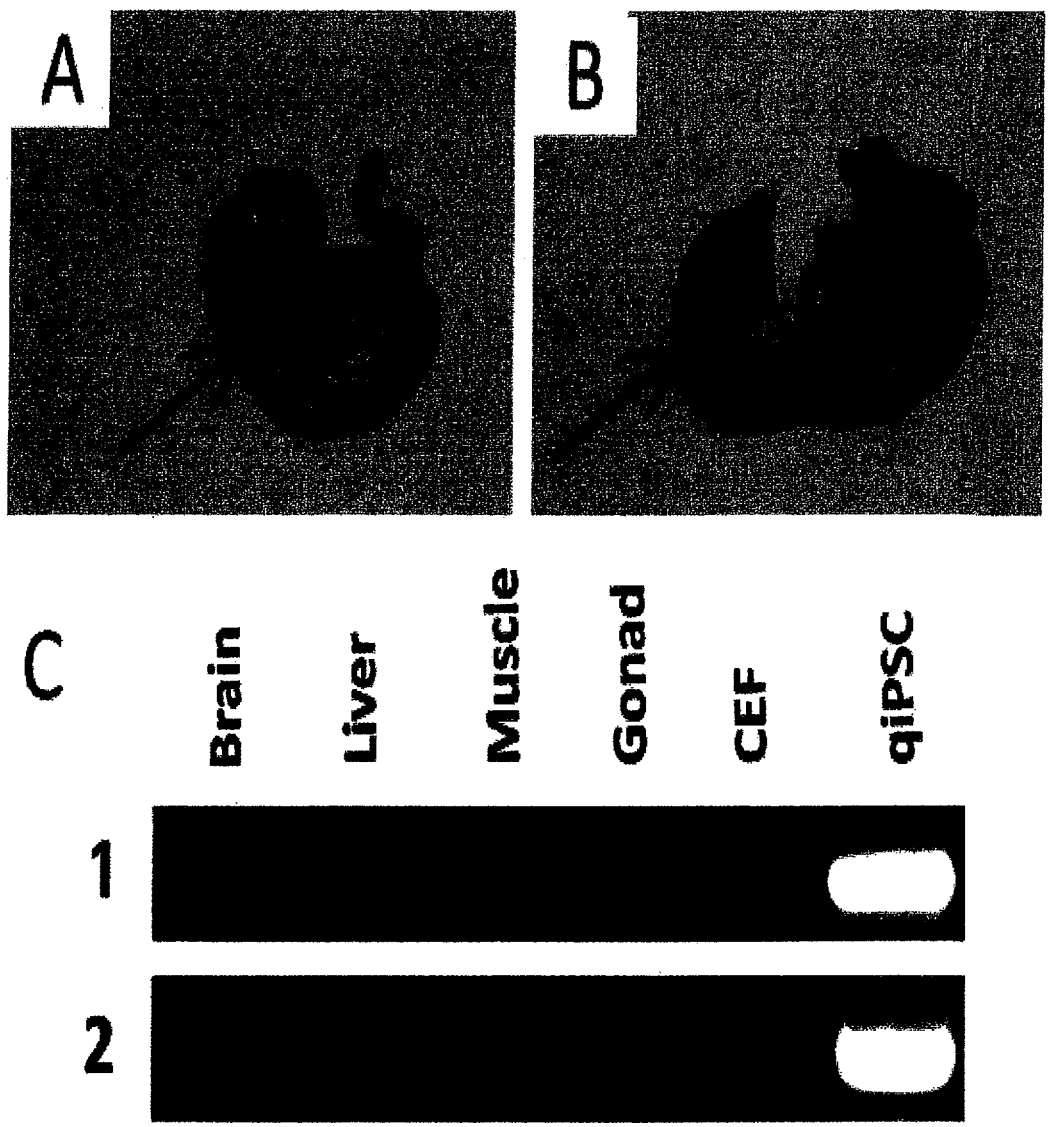
FIG. 7 also shows chimeric chickens derived from qiPSC Two chicks produced by low passage qiPSC (P7) determined to be at day 14 (A) and 19 (B) developmental stages exhibited significant levels of feather chimerism (black arrow), yet failed to hatch. High passage qiPSC (P45) contributed to live chemeras as indicated by the presents of the human POU5F1 gene in the brain, liver and gonad of two individuals (N=15; C).

An additional two rounds of injections were performed to generate chimeric chicks using passage 7 and passage 45 qiPSCs. Early passage qiPSCs were injected into 30 eggs. Three embryos developed to term and hatched after 21 days of incubation, while 18 embryos failed to hatch. Hatched offspring were not chimeric, but two chicks at late stages of development showed feather chimerism (FIG. 7A, 7B). Passage 45 qiPSCs were injected into 102 eggs, resulting in 47 live offspring. Two chicks died soon after hatching and the rest of 45 chicks were healthy, but no feather chimerism was observed. Brain, muscle, liver and gonad tissues were collected from 15 chickens for PCR detection of qiPSC incorporation. Results showed that brain, liver and gonad samples from two individuals were positive for the human POU5F1 reprogramming gene (FIG. 7C). The presence of feather chimerism with early passage cells and incorporation of qiPSCs into tissue with later passages indicate that these cells retain pluripotent characteristics following long term culture and are still capable of contributing to multiple lineages following prolonged culture.

Discussion

Induced pluripotent stem cells have been generated from numerous mammalian species (1, 2, 5-10), but never before in a non-mammalian species. Here we report the first non-mammalian iPSCs and paradoxically these avian iPSC were generated using human reprogramming factors. Also a constitutively expressed GFP marker was introduced into qiPSCs and subclones were selected and expanded based on expression of GFP in a feeder free culture system. Therefore these qiPSC are amenable to future gene targeting, and exhibit a proliferative potential never before reported for any avian pluripotent cell lines (11, 25-27). The qiPSCs show morphology consistent with previously established pluripotent stem cells at the single cell level. The qiPSCs are highly positive for the stem cell markers AP, PAS, POU5F1 and SOX2 that have been previously used to characterize avian ESCs and PGCs (26, 28-31). These iPSCs are highly proliferative with a doubling time of 16.6 hr, similar to iPSCs from mouse (1) and pig (32), and have undergone over 50 passages. qiPSCs generated all three germ layer cells after spontaneous EB differentiation and then using a mammalian neural directed in vitro differentiation process we generated astrocytes, oligodendrocytes and neuronal cells. In the chick/quail chimera model, qiPSC contributed to fetal tissues from all 3 germ layers and extraembryonic tissues and ultimately contributed to tissues in live offspring. Although avian ESC and PGC have generated chimeric offspring (29, 33), the qiPSC differ because for the first time an avian stem cell exhibits the robust in vitro proliferative and clonal attributes needed for future gene targeted birds.

Quail and quail-chick chimeras have long been used in understanding the development of the neural system (34-37). With the benefit of this avian system, numerous facets of neural development in the brain (13, 34) and neural crest (35) have already been deciphered. In the present study, qiPSCs were found to significantly contribute to the brain and eye tissue when injected into stage X chicken embryos in an undifferentiated state. Upon proper signaling in vitro, qiPSCs could differentiate into a neural progenitor (TUJ1+) and all 3 lineages of neural cells: neuronal (Hu C/D+ and MAP2+), astrocyte (GFAP+) and oligodentrocyte (O4+) in vitro. This level of neural competence in vitro and in vivo has not been reported in previous avian pluripotent cell lines (11, 12), indicating their potential use in neural development and disorder research (38-40). Given that we have derived neuronal, astrocyte and oligodendrocytes using processes first developed in human pluripotent cells (41), the repertoire of "tools" and translational potential for embryonic graft studies is greatly enhanced. Temporal and spatial studies investigating the role and interaction among neural cell types during embryo development is now possible. Pluripotent derived neural cells vs tissues isolated from fetal and adult tissues can be compared faster and in a relevant but comparatively simple models in contrast to mammalian systems (20).

The successful use of human reprogramming factors to generate avian iPSC suggests that direct reprogramming mechanisms are widely conserved among species. In the chicken genes cPouV and cNanog were found as key factors in the maintenance of chicken pluripotency (42). However, homology between avian and human is not obvious for the reprogramming genes with homology being relatively low when comparing chicken, the only avian species with sequence data, and humans with homology ranging from approximately 53 to 81% for POU5F1, NANOG, LIN28, C-MYC and KLF4. SOX2 is the lone exception with homology of 94% between chicken and human genes. Based on the diverse number of species (mouse, human, pig) from which cells have been reprogrammed using human factors and now a non-mammalian species, we hypothesize that the reprogramming process is highly conserved. Therefore, direct reprogramming with transcriptional factors could be a universal strategy for generating iPSC lines in distantly related species. This would provide new species iPSCs for divergent species including species where embryonic stem cells are hard to isolate, maintain and expand, which arguably would include all species other than those of primates and some rodents.

The methods used here for qiPSCs overcome impediments inherent to avian ESC and PGC. Previously quail or chicken PGCs (31, 33) and ESCs (29) contributed to chimeras when injected into embryos immediately after collection from the donor embryo or after only a few passages. After serial subculture in this system, qiPSC still efficiently incorporated into tissues from all three germ layer in chimeric embryos at passages 26 and 45. This will further enable complex genetic manipulations like homologous recombination, multiple gene introductions, drug selection and other strategies that may require extended culture. This significantly increases the value of these cells for future developmental studies. In addition, cultures beyond 50 passages that maintain a short doubling times and a pluripotency phenotype have not been previously reported. Beyond long term culture, qiPSCs demonstrated the capability of clonal expansion after isolating individual cells in a 96 well format providing the possibility of targeting genes of interest. Little is known about the maintenance of pluripotency and expansion of avian pluripotent cells therefore we used methods based on the significant body of knowledge for mammalian pluripotent cells (43-47). The feeder free culture system that supported qiPSC cultures for more than 50 passages without loss of the pluripotent phenotype was developed for human pluripotent cells and contains high levels of bFGF (48). In the future this system can be used to investigate individual factors and their role in maintaining pluripotency of avian stem cells. Using qiPSC gene targeted avian models will compliment important rodent models in disease and developmental gene function studies (49).

The present invention is directed to avian iPSCs which will greatly facilitate the insertion of genetic reporters and gene targeting. Future studies generating cells with gene specific and multiple promoters, inducers and conditional expression systems in avian iPSCs is likely feasible; thus enhancing the research communities' capabilities when it comes to investigating cell migration and contribution in developing embryos in ova (50). Since these qiPSC and ciPSC were capable of clonal expansion after genetic modification, targeting genes of interest is potentially possible, which would facilitate research on gene function and signaling pathways underlying the development process in chimeric embryo. Furthermore, avian iPSC derivatives such as neural cells should compliment mammalian cell transplant models for regenerative medicine (51). In total, this unique source of avian iPSC and derivative cells will provide biologist with multiple opportunities to enhance and expedite developmentally related discoveries.

Materials and Methods for Quail Pluripotent Stem Cells

Cell Culture and Transduction

QEFs were isolated from day 11 embryos and cultured in fibroblast medium (DMEM high glucose (Hyclone) with 10% FBS (Hyclone), 4 mM L-Glutamine (Gibco) and 50 U/ml penicillin and 50 μg/ml streptomycin (Gibco)) in 5% $CO_2$ at 37° C. Cells were split using 0.05% trypsin (Gibco) upon confluency. For transduction, a total of 150,000 QEF cells were plated in one well of a 12-well plate. After 24 hrs QEFs underwent lintiviral transduction utilizing the viPS kit (Thermo Scientific) with viruses containing the human stem cell genes POU5F1, NANOG, SOX2, LIN28, KLF4 and C-MYC under the promoter of human elongation factor-1 alpha (EF1α). Transduction was performed in the present of 1× TransDux (System Biosciences). QEFs were trypsinized 24 hrs after transduction and passaged onto inactivated feeder cells in embryonic stem cell expansion medium (Dulbecco's modified Eagle medium (DMEM)/F12 (Gibco), supplemented with 20% knockout serum replacement (KSR; Gibco), 2 mM L-glutamine (Gibco), 0.1 mM non-essential amino acids (Gibco), 50 U/ml penicillin/50 □g/ml streptomycin (Gibco), 0.1 mM β mercaptoethanol (Sigma-Aldrich) and 10 ng/ml bFGF (Sigma-Aldrich and R&D Systems). qiPSC was manually harvested and plated on Matrigel (BD Biosciences; diluted 1:100 in DMEM/F12) coated dishes in mTeSR1 (Stemcell Technologies) medium. qiPSCs were mechanically dissociated using glass Pasteur pipette every 4 to 5 days. For clonal expansion, qiPSCs were transduced with GFP viral vector and single cells were FACS sorted into individual wells of a 96-well plate.

Alkaline Phosphatase and Periodic Shiff's Acid Staining

AP staining was carried out with VECTOR Red Alkaline Phosphatase Substrate Kit (Vector Laboratories) according to the manufacturer's instructions. PAS staining was performed by 4% fixation for 5 min. PAS (Sigma-Aldrich) was added to the plate and incubated at room temperature (RT) for 5 min, followed by PBS washes. Schiff's reagent (Sigma-Aldrich) was added and incubated at RT for 15 min, followed PBS washes and then observation.

Immunocytochemistry

Protocol for immunostaining followed the methods previous reported (6). Primary antibodies used were POU5F, 1 (R&D Systems), SOX-2 (R&D Systems), Tuj1(Neuromics), αSMA (Santa Cruz), Sox17 (Santa Cruz), SSEA4 (Developmental Studies Hybridoma Bank), TRA-1-60 (Chemicon), TRA-1-81 (Chemicon), Hu C/D+ (Invitrogen), MAP2+ (Millipore), GFAP (Chemicon) and 04 (Chemicon).

Proliferation and Telomerase Activity

Proliferation assay was performed by manual counts (n=3) at 12, 24, 36 and 48 hrs after plating. Population doubling time was determined using an exponential regression curve fitting (http://www.doubling-time.com/compute.php). Telomerase activity of QEFs, qiPSCs and HeLa cells (positive control) was determined using TRAPeze XL Telomerase Detection Kit (Millipore) following manufacturer's instructions. Statistics analysis was done utilizing ANOVA and Tukey pair-wise comparisons between each population with p-value <0.05 being considered significant.

Embryoid Body Formation and Differentiation

Embryoid bodies (EBs) were formed by plating $2.0 \times 10^6$ qiPSCs in mTeSR1 medium and 0.1 mM Y-27632 ROCK inhibitor (Calbiochem) in AggreWell plate (Stemcell Technologies). After 24 hrs, aggregates were harvested and maintained in mTeSR1 medium for 7 days. Differentiation was assessed by RT-PCR using the primers in S. Table 2.

Neural Differentiation

To induce neural differentiation qiPSCs were sequentially cultured in neural derivation medium (DMEM/F12 supplemented with 200 mM L-Glut, 4 ng/ml bFGF and 1× N2) for 12 days, proliferation medium (AB Medium supplement with 200 mM L-Glut, 1×ANS and 20 ng/mL bFGF) for 7 days and then in differentiation (AB Medium supplement with 200 mM L-Glut, 1×ANS and 10 ng/mL LIF) mediums continuously.

Production of Chimera

Stage X white leghorn chicken embryos were used to produce chimeras. Egg shells were removed by Dremel rotary tool to make injection window (FIG. 9A). qiPSCs were introduced into the subgerminal cavity using a glass micropipette (FIG. 9B) with pressure controlled microinjector (Parker Automation). The window was sealed by hot glue (FIG. 9C) after injection and eggs were incubated at 37° C.

RNA Isolation, DNA Isolation, PCR and Sequencing

Figure 8:
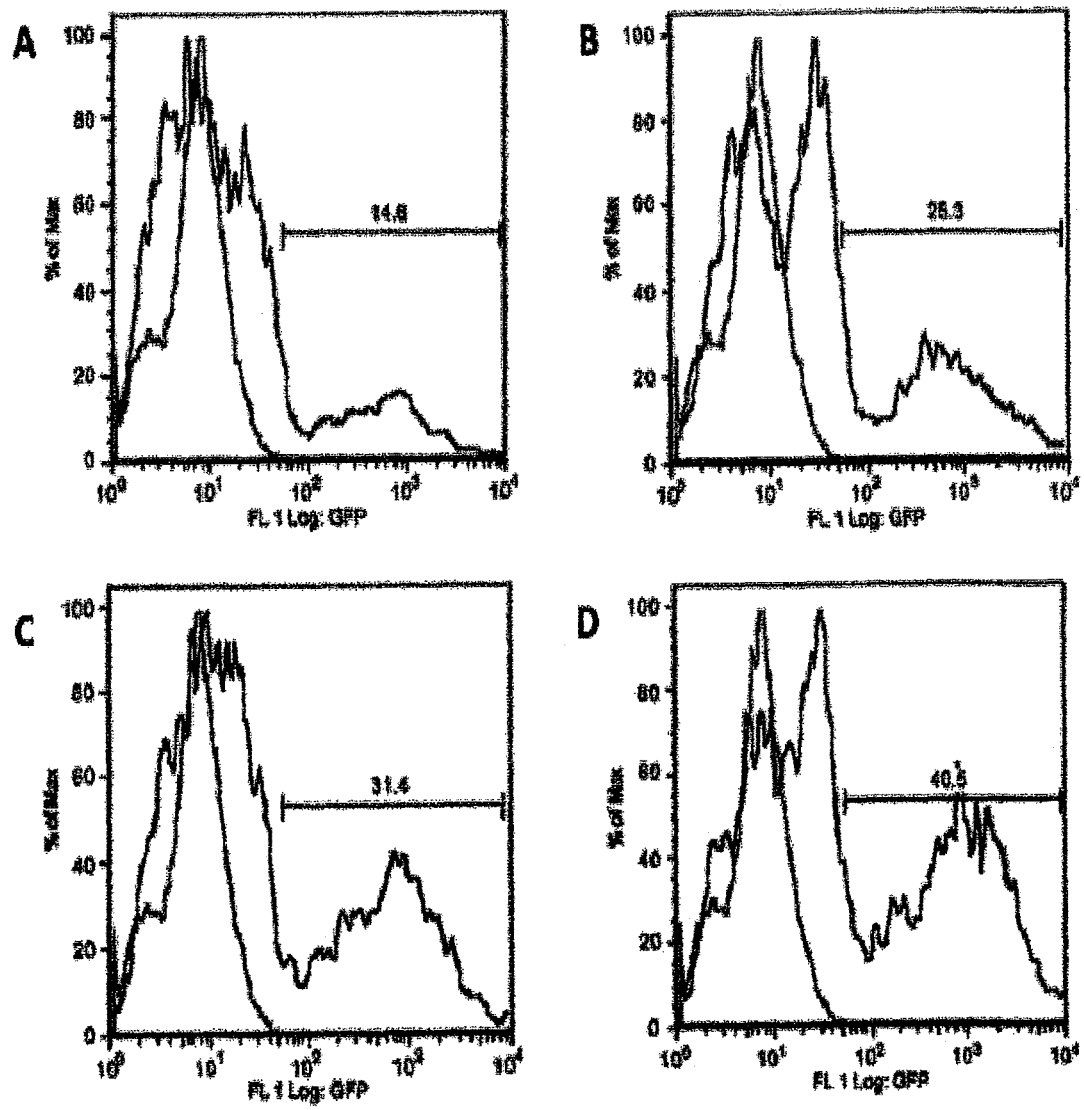
FIG. 8 shows the transduction efficiency in QEF. QEFs were transduced with lentiviral eGFP gene constructs. Flow cytometry was carried out 48 hours after transduction. Utilizing GeneJammer, at 10 MOI 14.6% of QEFs were transduced (A) and at 20 MOI 25.3% of QEFs were transduced and (B) expressed GFP. While using TransDux, at 10 MOI 31.4% of QEFs were transduced (C) and at 20 MOI 40.5% QEFs were transduced and (D) expressed GFP.

RNA was isolated using RNeasy QIAprep Spin miniprep Kit (Qiagen) per manufacture's instructions. mRNA extractions were transcribed into cDNA using iScript cDNA Synthesis kit (Bio-Rad Laboratories). DNA was isolated using DNeasy kit (Qiagen) following the manufacturer's instruction. All DNA samples were subjected to RNase treatment to eliminate the RNA contamination. Primers used in PCR and RT-PCR are listed in attached FIG. 8. Sequencing verification of hPOU5F1 was performed by extracting DNA from agarose gel after electrophoresis and sequenced. The product was compared by Blast in NCBI data base to both human and chicken genomes.

TABLE 1

Incorporation of qiPSCs in chicken chimeric embryonic tissues

|  | Tissue | No. of Samples Subjected to PCR | No. of Samples Positive For hPOU5F1 |
|---|---|---|---|
| Ectoderm | Brain | 18 | 9 |
|  | Eye | 18 | 7 |
|  | Skin | 17 | 5 |
| Endoderm | Intestine | 18 | 4 |
|  | Liver | 16 | 5 |
|  | Lung | 18 | 7 |
|  | Trachea | 6 | 3 |

TABLE 1-continued

Incorporation of qiPSCs in chicken chimeric embryonic tissues

| | Tissue | No. of Samples Subjected to PCR | No. of Samples Positive For hPOU5F1 |
|---|---|---|---|
| Mesoderm | Muscle | 18 | 4 |
| | Heart | 18 | 3 |
| | Gonad | 10 | 5 |
| | Kidney | 7 | 4 |
| | Gizzard | 8 | 1 |
| Extra Embryonic | Yolk sac | 1 | 1 |

TABLE 2

Sequence of primers used in the study

| Primer | SEQID | Sequence | Product (bp) |
|---|---|---|---|
| hPOU5F1 | Forward 01 | GAGAAGGAGAAGCTGGAGCA | 453 |
| | Reverse 02 | TCGGACCACATCCTTCTCG | |
| hSOX2 | Forward 03 | CCCCTGTGGTTACCTCTTCCTCC | 177 |
| | Reverse 04 | TGCCGTTAATGGCCGTGCC | |
| hNANOG | Forward 05 | CTATGCCTGTGATTTGTGGG | 160 |
| | Reverse 06 | GGTTGTTTGCCTTTGGGAC | |
| hLIN28 | Forward 07 | GGCTCCGTGTCCAACCA | 281 |
| | Reverse 08 | AACTCCACTGCCTCACCCT | |
| hC-MYC | Forward 09 | GTTTCATCTGCGACCCG | 480 |
| | Reverse 10 | CAGGAGCCTGCCTCTTTT | |
| hKLF4 | Forward 11 | GGCTGATGGGCAAGTTCG | 395 |
| | Reverse 12 | CTGATCGGGCAGGAAGGAT | |
| qGAPDH | Forward 13 | TGCCCAGAACATCATCCCA | 295 |
| | Reverse 14 | GCCAGCACCCGCATCAAAG | |
| hGAPDH | Forward 15 | GAGTCAACGGATTTGGTCGT | 283 |
| | Reverse 16 | TTGATTITGGAGGGATCTCA | |
| Vimentin | Forward 17 | GTCTGGATACTCGCAGTTAGG | 175 |
| | Reverse 18 | GGTGTAGGGATTGGGGTAG | |
| Brachyury | Forward 19 | TCTGGATACTCGCAGTTAGGT | 365 |
| | Reverse 20 | ATGGTGCTGTTACTCACGGAC | |
| PAX6 | Forward 21 | CAGAAGATCGTGGAACTCGC | 280 |
| | Reverse 22 | CACTGGGTATGITATCGTTGGTA | |
| TUJ1 | Forward 23 | CAGCGATGAGCATGGCATAGAC | 576 |
| | Reverse 24 | CGGAAGCAGATGTCGTACAGG | |

Chicken Pluripotent Stem Cells

The Generation of Integrated Virus Induced Pluripotent Cells Using Chicken Cells was Unique and Unexpected Because Previously Used Key Reprogramming Factors was not Required In previous reports, iPS cell lines were derived by using all 6 factors of OCT4, SOX2, NANOG, LIN28, KLF4 and CMYC. In the present invention, as set forth herein, we find that exogenous expression of NANOG, LIN28 and CMYC were sufficient to reprogram the chicken fibroblast cell into pluripotent status, the first time demonstrating OCT4 is dispensable in iPSC derivation. Moreover, these ciPSC could be cultured on feeder free system, on plates coated with Matrigel or directly on plate without any matrix. This feature would reduce the cost of cell culture and facilitate the cell screening or vaccine production where large amount of culture are required.

Materials and Methods

Chicken Embryonic Fibroblast Culture

Black australorp chickens embryonic fibroblast cells (CEFs) were isolated from a day 11 embryo. CEFs were then cultured in DMEM media (Hyclone) supplemented with 10% FBS (Hyclone), 4 mM L-Glutamine (Gibco) and 50 U/ml penicillin and 50 µg/ml streptomycin (Gibco)) and incubated in 5% $CO_2$ and at 37° C., with media changes every other day. Cells were subcultured using 0.05% trypsin (Gibco) upon confluency.

ciPSC Derivation

A total of 150,000 CEF cells were plated in one well in a 12-well plate. After 24 hrs CEFs underwent lintiviral transduction utilizing the viPS kit (Thermo Scientific) with viruses containing the human stem cell genes POU5F1, NANOG, SOX2, LIN28, KLF4 and C-MYC under the promoter of human elongation factor-1 alpha (EF1α). Transduction was carried out at a multiplicity of infection (MOI) of 10 in the present of 1× TransDux (System Biosciences). The transduced CEFs were replated onto inactivated mouse embryonic fibroblast (MEF), fed with conditioned embryonic stem cell (ESC) expansion media (Dulbecco's modified Eagle medium (DMEM)/F12 (Gibco), supplemented with 20% knockout serum replacement (KSR; Gibco), 2 mM L-glutamine (Gibco), 0.1 mM non-essential amino acids (Gibco), 50 U/ml penicillin/50 µg/ml streptomycin (Gibco), 0.1 mM mercaptoethanol (Sigma-Aldrich) and 10 ng/ml FGF-2 (Sigma-Aldrich and R&D Systems). Conditioning of the medium was done by incubating the medium on MEF for 24 hours. Upon 50% confluent, the transduced CEFs were dissociated using 0.05% tripsin and replated on fresh MEF plates. Attrition of incorrectly reprogrammed cells was performed by serial tripsin passages until the majority of the coloies were iPSC-like cells. At the end of the attrition, the ciPSCs were manually passaged onto tissue culture plate coated with Matrigel in ESC medium. The stable ciPSC cells were culture on plate coated with Matrigel or without any matrix and passaged every 3-4 days using accutase.

Alkaline Phosphatase and Periodic Shiff's Acid Staining

Following the protocol used in derivation of quail iPSC as described for the quail experiments described above.

Immunocytochemistry

Follow the same protocol as in quail iPSC, described above. The primary antibody used in this experiment were SSEA1 (1:20; Developmental Studies Hybridoma Bank), DDX4 (1:500, Abeam). Secondary antibodies were Alexa Fluor (Invitrogen) diluted at 1:1000.

DNA, RNA Isolation and PCR

DNA was isolated from CEFs and ciPSCs using DNeasy kit (Qiagen) following the manufacturer's instruction. Human specific primers were use to analyze the incorporation of transgenes in ciPSCs.

RNA was isolated from CEFs and ciPSC using RNeasy QIAprep Spin miniprep Kit (Qiagen) following manufacturer's instructions and then transcribed into cDNA using iScript cDNA Synthesis kit (Bio-Rad Laboratories). Quantitative PCR was performed to analyze the chicken endogenous pluripotent genes expression using validated primers from Applied Biosystem.

Embryoid Body Formation and Differentiation

Embryoid bodies (EBs) were formed follow the same protocol as in quail iPSC as described in the experiments described above. The EBs were harvested on day 7 and RNA was isolated to for RT-PCR to check the expression of genes from different lineages.

Results

Derivation of ciPSC

CEFs were cultured in modified DMEM (FIG. 10A) were transduced with 6 human stem cell factors (hOCT4, hSOX2, hNANOG; hLIN28, hKLF4 and hCMYC) constructed in lentiviral vectors. The transduced CEFs were replated onto inactivated MEF plate 24 hours after transduction and feed with conditioned ESC medium. Obvious colonies were observed 5 days after transduction (FIG. 10B). The ciPSC-like cells demonstrated typical stem cell characteristics as large nuclear and prominent nucleoli (FIG. 10C). A pure population of ciPSCs were derived by serial passages 50% confluence (FIG. 10D) using 0.05% tripsin and finally repeated on Matrigel coated plate when the majority of the colonies demonstrating typical stem cell characteristics. The stable ciPSC were cultured in on feeder free system, on culture dish coated with Matrigel or without any matrix. The ciPSCs maintained in feeder free system are highly positive in AP (FIG. 10F) and PAS (FIG. 10G) staining. And some of the cells are positive for SSEA1 (FIG. 10H while all are positive for DDX4 (FIG. 10I).

ciPSCs Express Pluripotent Genes

Figure 11:
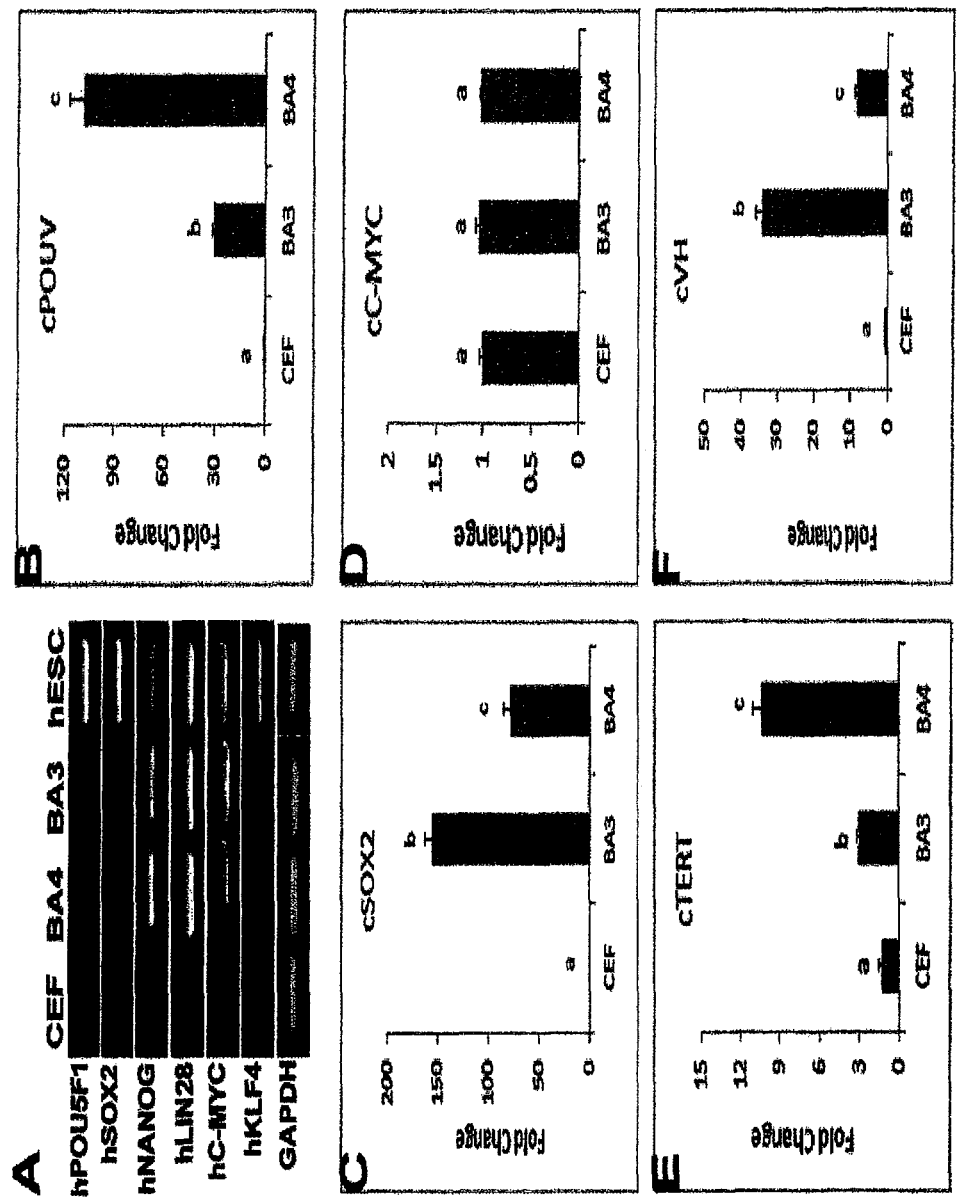
FIG. 11 shows pluripotent genes expression in ciPSCs. PCR showed that human stem cell genes hNANOG, hLIN28 and hC-MYC were incorporated in ciPSCs (A). Quantitative PCR showed that the chicken endogenous gene cPOUV, cSOX2, cC-MYC, Telomerase reverse transcriptase (cTERT) and chicken VASA Homologue (cVH) were significantly upregulated in ciPSC BA3 and BA4 line over the CEF (B, C, D, E, F).

PCR using human specific primers revealed that, of the 6 human transcription factors that we used to derive the ciPSC, only hNANOG, hLIN28 and hC-MYC were incorporated in ciPSC BA3 and BA4 cell lines (FIG. 11A). The quantitative PCR demonstrated that the endogenous OCT4, SOX2 were highly up regulated in ciPSCs comparing to the CEFs (FIG. 11-C), indicating the activation of the endogenous stem cell regulatory network. However, we found that the chicken C-MYC was expressed at a similar level in CEFs and ciPSC. The over expression of the exogenous C-MYC might be responsible for the maintenance of the pluripotent thus endogenous expression is dispensible. The telomerase reverse transcriptase (cTERT) gene was significantly up regulated in ciPSC (FIG. 11E), confirming that these cells regained the immortality after reprogramming. And the chicken vasa homologue (cVH), a germ cell specified gene, was also expressed in high level in ciPSC (FIG. 11E). The expression of cVH was consistent with results of immunostaining, indicating these cells have the germ cell potential.

Differentiation of ciPSCs Through Embryoid Body

Figure 12:
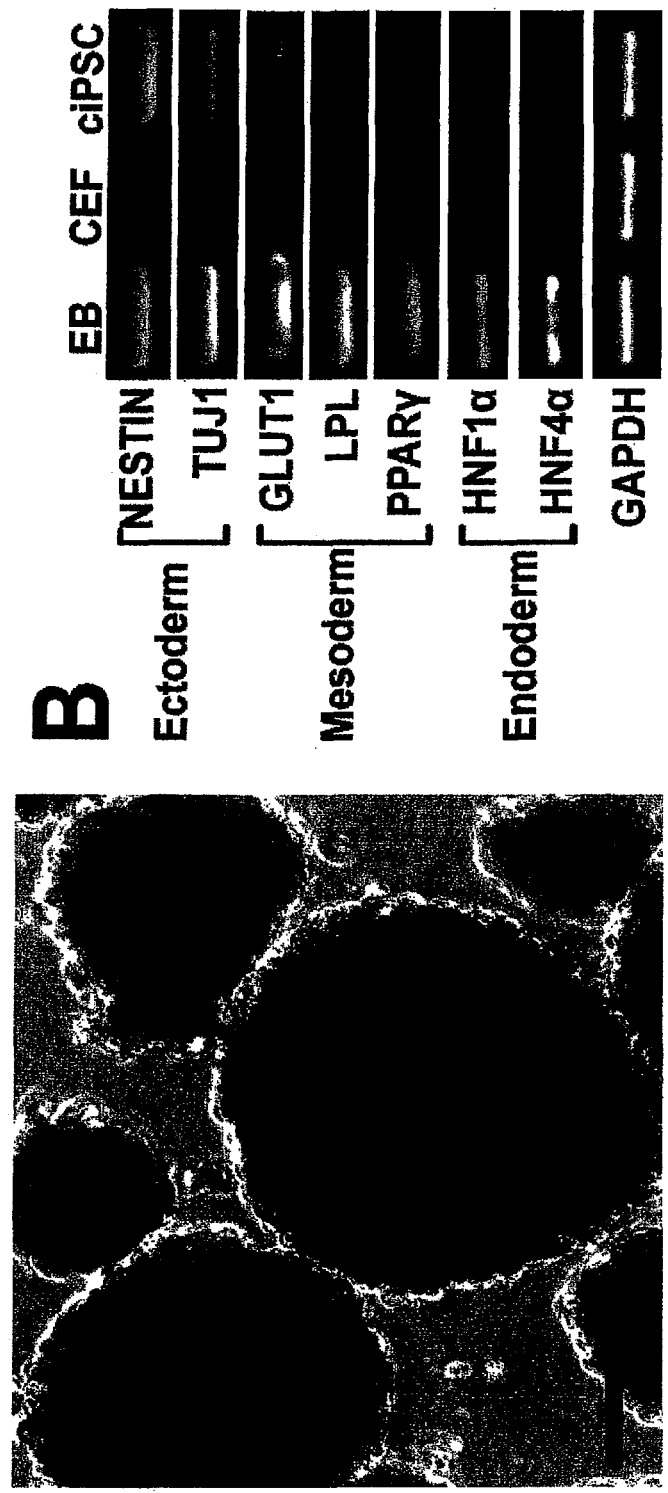
FIG. 12 shows ciPSCs differentiated into cells from all 3 germ layer in vitro. To perform the differentiation through embryoid body formation, ciPSC were plated in Aggrewell plates for 24 hours and the aggregates were then harvested and cultured in suspension for 6. days (A). RT-PCR revealed that the ciPSCs differentiated into all 3 germ layers.

Differentiation of ciPSCs was performed through embryoid body formation using AggreWell system. Around 2.0×10^6 cells were plated in one well in the Aggrewell plate thus yielded 1,000 cells per aggregate. The aggregates were cultured in ESC medium for 24 hours and then transfer to a 100 mm plate for suspension culture in ESC medium without bFGF for 7 days. Compact EBs were formed at the end of the culture (FIG. 12A) and RNA was isolated from the EBs. The results of RT-PCR showed the gene expression of ectoderm (NESTIN, TUJ1), mesoderm (GLUT1, LPL, PPARγ) and endoderm (HNF1α, HNF4α) was found in the EBs derived cells.

ciPSCs Derived in this Study are Unique Because Conducting a $2^{nd}$ Round of Reprogramming can Yield More Pluripotent Cells (SSEA1) after Selection for NDV Resistant Generation of disease resistant animals has been a major goal of the breeding programs using state-of-art biotechnologies and chimeric animal production using disease resistant pluripotent stem cells is a promising strategy for this purpose. However, the serial cell screening or genetic manipulation in vitro usually results in reduction of the pluripotency and thus fails to produce chimeric animals. The ciPSC pursuant to the present invention is easy to maintain in feeder free system and were used in serial screening to establish Newcastle Disease Virus screening (NDV) cell line. Following a $2^{nd}$ round of reprogramming, the resistant ciPSCs demonstrated a more pluripotent state as indicating by higher percentage of cells are positive for SSEA1 and other markers, and these markers were previously reported to be required in pluripotent cells that would produce chimeric chicken.

Materials and Methods

NDV Screening

CEF and ciPSCs were plated in Matrigel coated 6-well plate at a density of 1×10^6 cells per well. NDV infection was performed 24 hours after plating at an MOI of 50. First, the medium from the culture is removed and washed with PBS once before infection. Second, the virus in ESC medium containing 1% KSR for ciPSCs or in DMEM medium containing 1% FBS for CEFs. Add the infection solution to cells and incubate at 39° C. in 5% CO2 for 1 hour. Finally, remove the infection solution at the end of the incubation and add fresh ESC medium and return the cells to incubator. Cell viability was assayed 48 hours after the NDV infection. The survived cells were subjected to serial rounds of virus challenging with or without passaging.

$2^{nd}$ Round Reprogramming

The transduction protocol used in the $2^{nd}$ round reprogramming is similar to the $1^{st}$ round. ciPSCs are plated on Matrigel coated plate in ESC medium. Cells were transduced with 6 human transcription factors (POU5F1, NANOG, SOX2, LIN28, KLF4 and C-MYC) constructed in lentiviral vectors at an MOI of 10 in the present of 1× TransDux (System Biosciences). Transduction medium was removed 24 hours after transduction and fresh ESC medium was added and change every other day. The reprogrammed ciPSCs was maintained and expanded in feeder free system and purification of the more-pluripotent ciPSCs were performed by MACS sorting using magnetic beads conjugated with anti-SSEA1 antibody (Miltenyi Biotech). The purified cells were cultured on MEF feeder for better maintaining of the pluripotency.

Results

Derivation of NDV Resistant ciPSCs

Figure 13:
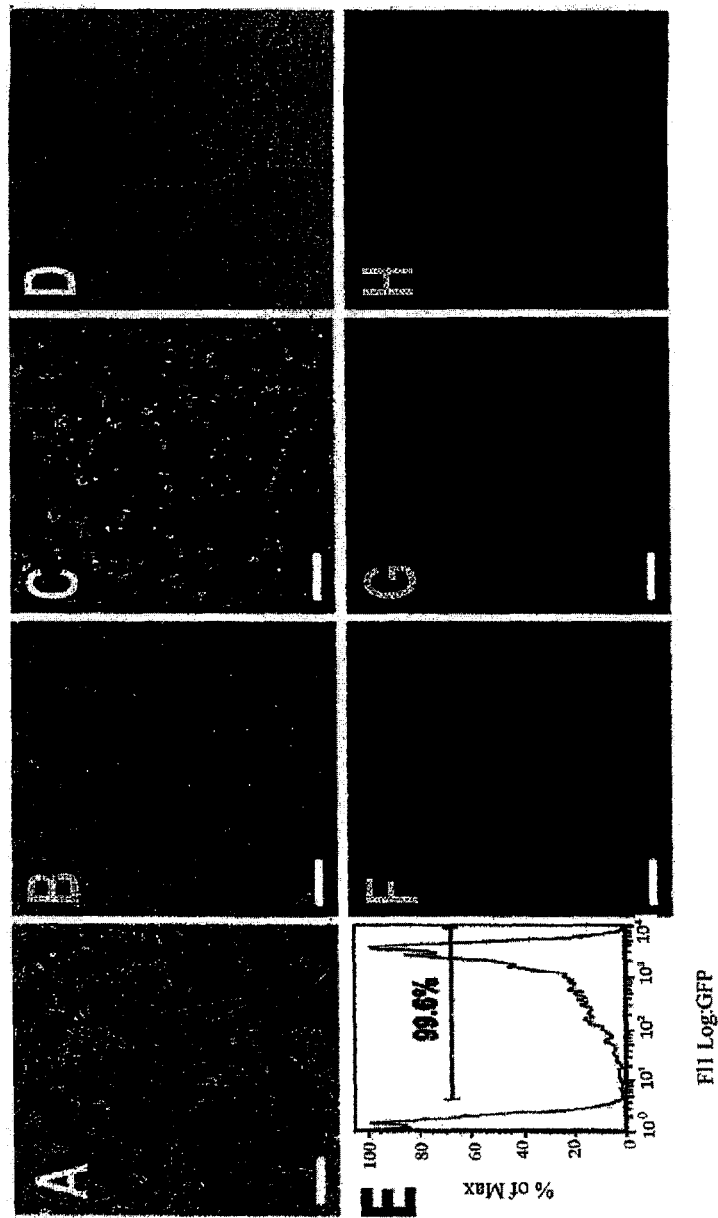
FIG. 13 shows the screening for NDV-resistant ciPSC The NDV virus screening was initiated at 50 MOI using GFP-NDV, with GFP indicating successful infection. An infection efficiency of >99% was seen in either CEFs (E) or ciPSCs (M). CEFs were used as control cell line for virus screening (A) and they grew to confluence in the mock infection dish (B, F) while mostly died in the infected dish 48 hours after infection (C, G). The infected CEFs could not recover from the infection 9 days after infection. ciPSCs plated on Matrigel dish (I) were used for NDV screening and they grew to confluence in the mock infection dish (J, N) while mostly died in the infected dish 48 hours after infection (K, O). 9 days after infection, ciPSC survived the NDV infection formed colonies and some of the cell were clear of the NDV virus.
Figure 13:
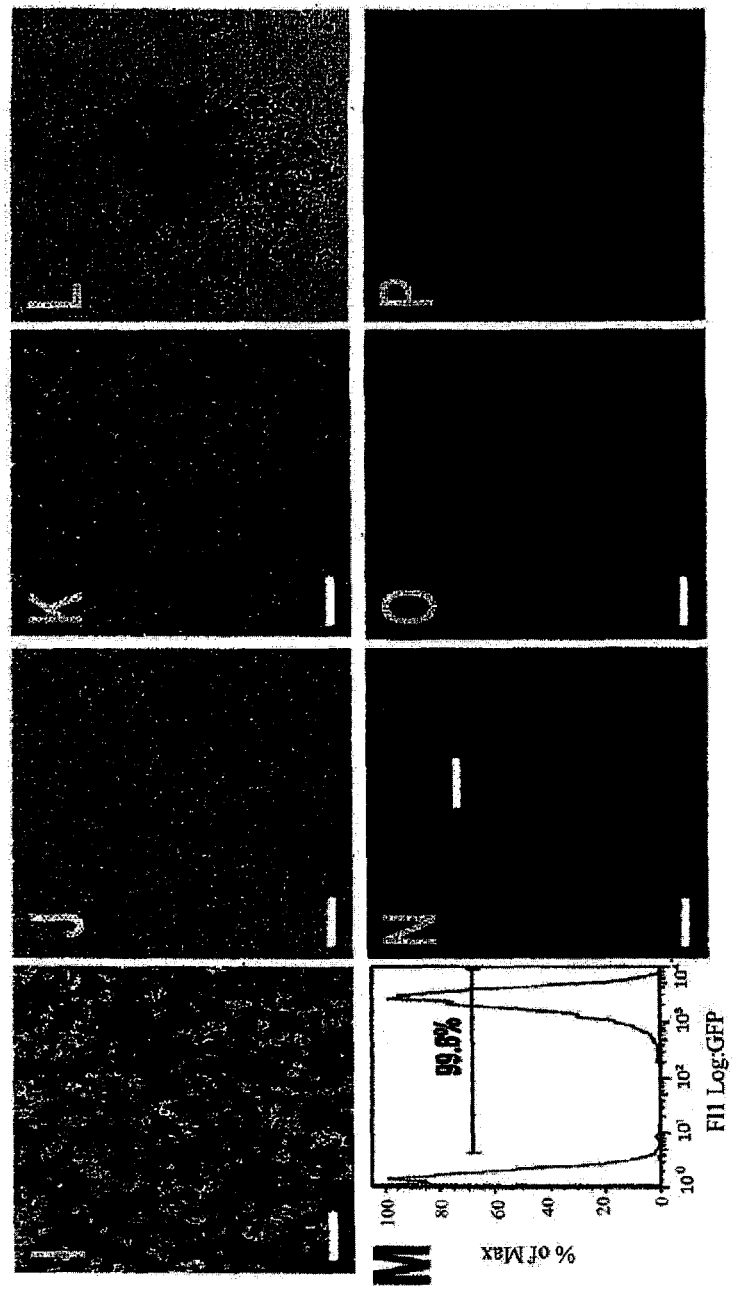

NDV used in this study was genetically modified and labeled with GFP thus the infection could be tracked by fluorescence from the infected cells. Result of flow cytometry showed an infection efficiency of >99% in either CEFs (FIG. 13E) or ciPSCs (M). There was significantly cell death in CEFs and ciPSCs 48 hours after the first round of NDV infection (FIGS. 13C, 13G and 13K, 13O). The survived ciPSCs recovered from the infection and formed obvious colonies around 9 days after the infection, with significant number of cells negative for GFP (FIG. 13L, 13P), while the CEFs remained infected and slowly proliferate or even stopped growing (FIG. 13D, 13H).

Figure 14:
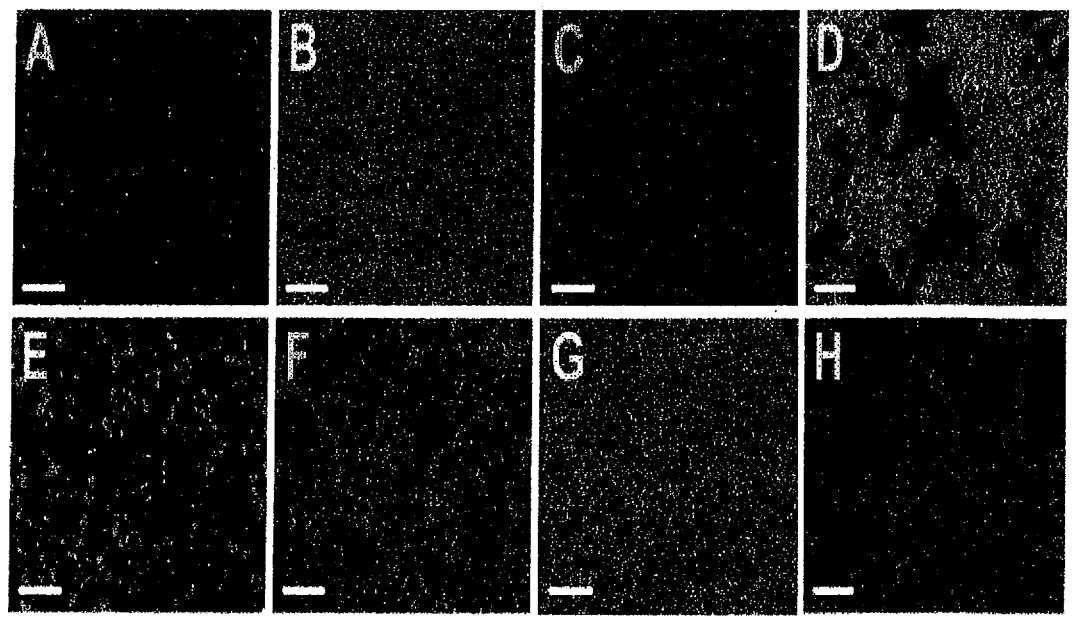
FIG. 14 shows the established ciPSC line demonstrates significant resistance to NDV. 48 after NDV infection, significant cell death was seen in infected CEF (E) and ciPSC I0 (F) dishes but not in ciPSC I12 (G) and ciPSC I14 (H), while in the mock infection control CEF, ciPSC I0, ciPSC I12 and ciPSC I14 showed rapid growth and confluence (A, B, C, D). The results of cell counts (I) 48 hours after NDV infection (normalized to mock control) showed significant resistant to NDV in ciPSC 112 and ciPSC 114 over their parent/original cell line CEF and ciPSC I0. (a,b: P<0.01)
Figure 14:
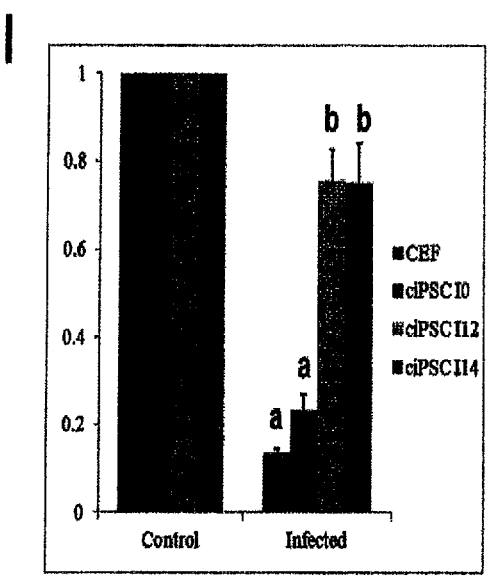
Figure 15:
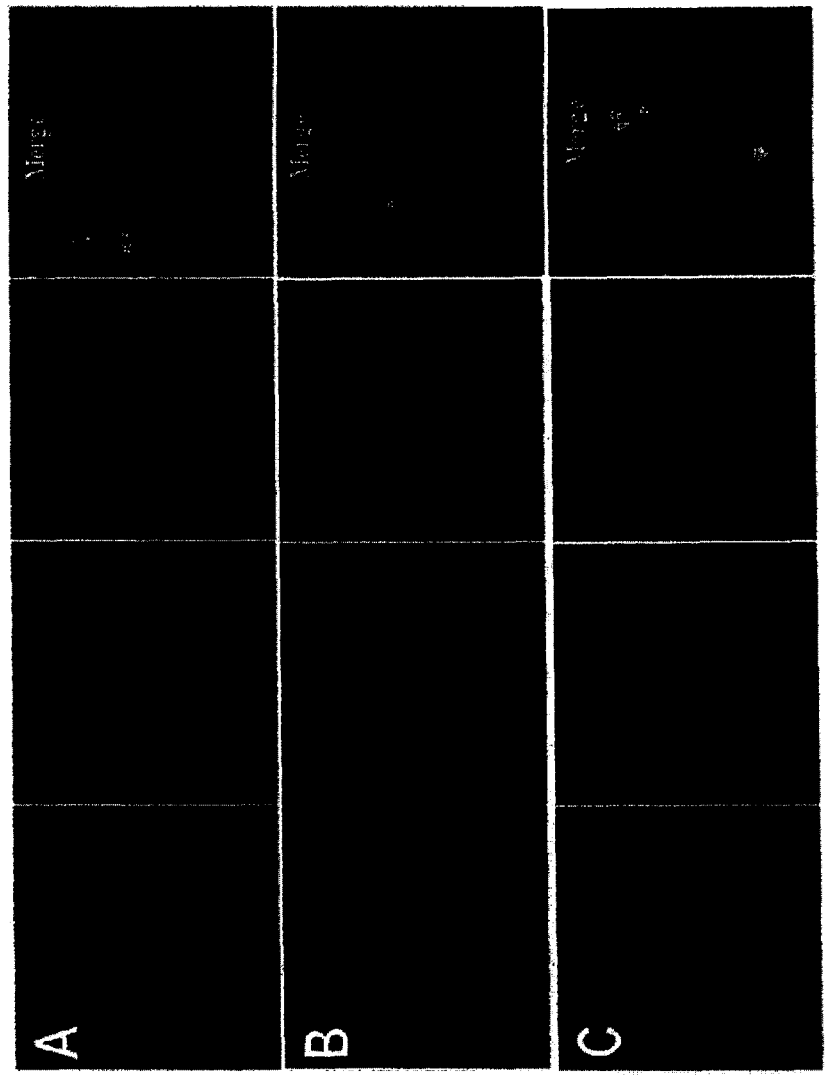
FIG. 15 shows that more pluripotent ciPSCs were derived by a 2nd round of reprogramming. The ciPSCs are positive for OCT4, SOX2, NANOG and SSEA1 after a $2^{nd}$ round of reprogramming (FIG. 6A-D). The SSEA1+ ciPSCs was enriched by MACS sorting and additional selection by manual picking yielded a population of ciPSCs >82% positive for SSEA1 (FIGS. 15E-G).
Figure 15:
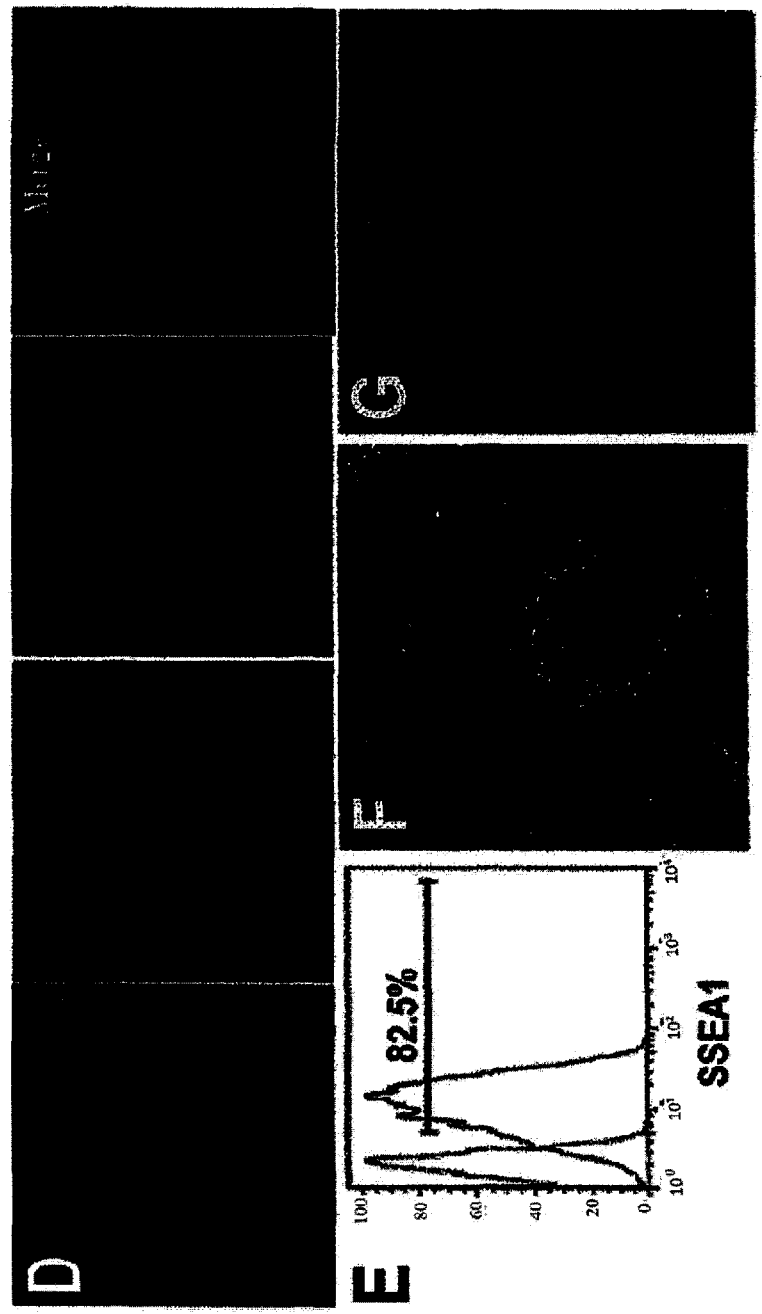

A total of 12 rounds of infection were carried to achieve a stable ciPSC line resistant to NDV. The established ciPSC lines showed significantly higher resistance to NDV upon infection comparing to CEFs or original ciPSCs never subjected to NDV infection (FIG. 14).

More Pluripotent ciPSCs was Derived by a 2nd Round of Reprogramming

The ciPSCs resistant to NDV were subjected to $2^{nd}$ of reprogramming by transduction of human stem cell factors constructed in lentiviral vectors and transduced were expanded on feeder free culture system. Cells positive for OCT4, SOX2, NANOG and SSEA1 were found 7 days after transduction (FIG. 6A), this pluripotent state was not seen in the 1st round of reprogramming. We then enriched the SSEA1+ cells by MACS sorting and yielded a purity >82% SSEA1+ cells. The stable SSEA1+ ciPSCs were finally plated on MEF layer for a better maintaining of the pluripotency.

Example

Chicken Induced Pluripotent Stem Cells Using a Non Integrating System.

The Benefits of Non Integrating Systems are the Following:

The molecular basis of reprogramming has been revealed by exogenous expression of combinations of transcription factors described in prior examples for quail and chicken, described above. Induction of reprogramming was carried by these factors is mostly carried out by co-infection with retroviral or lentiviral vectors. The main problems of the retrovirus-based method are oncogenicity and mutagenesis. Chimeric mice derived from iPSCs as well as their offspring developed tumors, probably because of reactivation of the proviral cMyc oncogene. Even though three-factor (Oct4, Sox2, and Klf4) iPSC-derived animals did not develop tumors, ectopic expression of any one of these genes may have deleterious consequences. For instance, ectopic expression of Oct4 in skin and intestine causes tumor development. Overexpression of Klf4 induces dysplasia in skin.

A non integrating system potentially avoids this pitfall and we have used a commercially available system Minicircle DNA (System Biosciences) to generate these types of cells in chickens.

Materials and Methods
Cell culture and Transfection

Chicken embryonic fibroblast (CEFs) from black australorp chickens were isolated from day-11 embryos and cultured in fibroblast medium [Dulbecco's modified Eagle's medium (DMEM) high glucose (Hyclone) with 10% fetal bovine serum (Hyclone), 4 mM Lglutamine(Gibco), and 50 U/mL penicillin and 50 mg/ml streptomycin (Gibco) in 5% $CO_2$ at 37° C. Cells were trypsinized and passaged using 0.05% trypsin (Gibco) upon reaching confluence. For transfection, a total of 1×106 CEF cells were plated in a 35 dish. After 24 hrs, CEF cells were transfected with Minicircle DNA (System Biosciences) containing the four reprogramming factors POU5F1, SOX2, LIN28, NANOG and the green fluorescent protein (GFP) reporter gene all driven by the cytomegalovirus promoter using four types of transfection reagents including lipofectamine (Invitrogen), (feet (Clontech), purefection (System Biosciences) and genejammer (Agilent Technologies). 5 μg of minicircle DNA was diluted in 250 ul DMEM/F, 12 and mixed with transfection reagent per transfection reagent manufacturer instructions. The mixture was incubated at room temperature for 20 min. The mixture was added to the CEF drop wise. After 24 hrs, the transfection reagent mixture was removed and replaced with fresh medium. The CEF cells were transfected a total of 3 times in this manner every other day over a 5 day period in. At day7, the CEFs were trypsinized and plated onto inactivated mouse embryonic fibroblast feeder cells in 20% KSR stem cell medium [DMEM/F12 (Gibco), supplemented with 20% knockout serum replacement (KSR; Gibco), 2 mM L-glutamine (Gibco), 0.1 mM nonessential amino acids (Gibco), 50 U/mL penicillin/50 mg/mL streptomycin (Gibco), 0.1 mM b mercaptoethanol (Sigma-Aldrich), and 10 ng/mL basic fibroblast growth factor (bFGF; Sigma-Aldrich and R&D Systems)]. To assess transfection efficiency, a subset of cells before plating in stem cell conditions from each transfection reagent treatment at day 6 was analyzed by flow cytometry for GFP expression.

ciPSCs were maintained on feeders and were mechanically dissociated using a glass pasteur pipette or passaged using 0.05% trypsin every 4-5 days. After 10 passages on feeder, the colonies were picked up and dissociated in 0.05% trypsin into single cells, and ciPSCs were directly passaged into feeder free conditions on Matrigel (BD Biosciences; diluted 1:100 in DMEM/F12) coated dishes in 20% KSR plus 10 ng/ml bFGF.

Flow Cytometry

Cells were fixed in 4% paraformaldehyde (PFA) for 15 min at room temperature. Cells were washed 3 times in phosphate-buffered saline (PBS; Hyclone) without calcium and without magnesium (−/−) and were blocked in 6% fetal bovine serum (FBS) 94% PBS blocking solution for 45 min. SSEA-1 (1:200; Developmental Studies Hybridoma Bank) primary antibody was added and cells were incubated for 1 hour. Cells were washed 3 times with blocking solution. Primary antibody was detected using fluorescently conjugated secondary antibody Alexa Flour 488 (1:1000; Invitrogen). Cells were analyzed using a Dakocytomation Cyan (DakoCytomation) and FlowJo Cytometry analysis software (Tree Star).

Alkaline Phosphatase and Periodic Acid Schiff's Staining

Following the protocol used in derivation of quail iPSC as described for the quail experiments described above.

Immunocytochemistry

Cells were passaged onto Matrigel coated slides. Cells were washed with PBS+/+ and fixed with 4% PFA at room temperature for 15 min. Fixed cells were blocked in 6% FBS 94% PBS+/+ blocking solution for 45 min. Cells were incubated with primary antibodies for 1 hour. Primary antibodies used were POU5F1 (1:500; Santa Cruz), SOX2 (1:200; R & D Systems), NANOG (1:200; Millipore), β III-Tubulin (1:200; Neuromics), *Brachyury* (1:200; Santa Cruz), Vimentin (1:100; BD Pharmingen), SSEA-1 (1:200; Developmental Studies Hybridoma Bank), SSEA-4 (1:200; Developmental Studies Hybridoma Bank), TRA-1-60 (1:200; Chemicon), TRA-1-81 (1:200; Chemicon). Primary antibodies were detected using a fluorescently conjugated secondary antibody, Alexa Fluor 488 (Molecular Probes, 1:500) and 594 (Molecular Probes, 1:500). Cells were observed and images were captured on the I×81 microscope with Disc-Spinning Unit (Olympus) using Slide Book Software (Intelligent Imaging Innovations).

Proliferation and Telomerase Activity ciPS cells were plated on 6-well plates at day 1 with $1 \times 10^5$ cells per well. Proliferation assay was performed by manual counts (n=3) at 12, 24, 36 and 48 hours after plating. Population doubling time was determined using an exponential regression curve fitting (website at doubling-time.com/compute.php).

Telomerase activity of CEFs, ciPSCs, WA09 human embryonic stem cells (hESCs) and Hela cells (positive control) were determined using TRAPeze XL Telomerase Detection Kit (Millipore) following the manufacturer's instructions. Statistical analysis was done utilizing ANOVA and Tukey pair-wise comparisons between each population with p-values <0.05 being considered significant.

Embryoid Body Formation and Differentiation

Emryoid bodies (EBs) were formed by plating $3.6 \times 10^6$ ciPSCs in 20% KSR medium and 0.1 mM Y-27623 ROCK inhibitor (Calbiochem) in an AggreWell plate (Stemcell Technologies). After 24 hours, cell aggregates were harvested and cultured in differentiation medium [DMEM/F12 (Gibco), supplemented with 20% fetal bovine serum (FBS;

Hyclone), 2 mM L-glutamine (Gibco), 0.1 mM nonessential amino acids (Gibco), 50 U/mL penicillin/50 mg/mL streptomycin (Gibco), 0.1 mM b mercaptoethanol (Sigma-Aldrich)] for 10 days. Differentiation was assessed by RT-PCR using the primers in Table1 to assess the differentiation by immunostaining, EBs were replated in 4 well chamber slides and differentiate further for 4 additional days in differentiation medium.

Re-Transfection and Medium Comparison

To compare several established stem cell culture system in maintaining ciPSCs pluripotency, $1 \times 10^6$ cells were plated on matrigel coated 35 mm dish and re-transfected with Minicircle DNA as before and were passaged directly into 1 of 5 feeder free culture systems. The medium components of the five culture system were as follows:

Group 1 20% KSR Medium:

DMEM/F12 (Gibco), supplemented with 20% knockout serum replacement (KSR; Gibco), 2 mM L-glutamine (Gibco), 0.1 mM nonessential amino acids (Gibco), 50 U/mL penicillin/50 mg/mL streptomycin (Gibco), 0.1 mM b mercaptoethanol (Sigma-Aldrich), and 10 ng/mL basic fibroblast growth factor (bFGF; Sigma-Aldrich and R&D Systems)];

Group 2 TGFβ1/LIF Medium:

DMEM/F12, supplemented with 20% KSR, 2 mM L-glutamine, 0.1 mM nonessential amino acids, 50 U/mL penicillin/50 mg/mL streptomycin, 0.1 mM b mercaptoethanol, 0.12 ng/ml TGFβ1 (Pepro Tech), 1000 unites/ml LIF(Millipore).

Group 3 LIF/Wnt3a Medium:

DMEM/F12, supplemented with 20% KSR, 2 mM L-glutamine, 0.1 mM nonessential amino acids, 50 U/mL penicillin/50 mg/mL streptomycin, 0.1 mM b mercaptoethanol, 100 ng/ml Wnt3a (R&D Systems), 1000 unites/ml LIE Group 4 2i/LIF Medium:

DMEM/F12 supplemented with N2 (Gibco) and mix 1:1 with Neurobasal medium (Gibco) supplemented with B27 (Gibco), 1 mM L-glutamine, 0.8 µM PD0325901(Sigma), 3 µM CHIR99021 (Selleckchem), 20 ng/ml LIF.

Group 5 TGFβ1/Activin A/Nodal Medium:

DMEM/F12, supplemented with 20% KSR, 2 mM L-glutamine, 0.1 mM nonessential amino acids, 50 U/mL penicillin/50 mg/mL streptomycin, 0.1 mM b mercaptoethanol, 0.12 ng/ml TGFβ1 (Pepro Tech), 10 ng/ml Activin A (R&D Systems), 50 ng/ml mouse recombinant nodal (R & D systems). All systems used Matrigel as the substrate.

RNA Isolation, DNA Isolation, PCR

RNA was isolated using RNeasy QIAprep Spin miniprep Kit (Qiagen) according to manufacturer's instructions. Genomic DNA was removed using gDNA eliminator columns (Qiagen). The RNA quality and quantity was determined using the NanoDrop 8000 (Thermo Scientific). Total mRNA (500 ng) extractions were reverse transcribed into cDNA using iScript cDNA Synthesis Kit (Bio-Rad Laboratories). PCR amplification was performed using GoTaq Green master mix (Promega). Primers used in RT-PCR are listed in Table 2A. PCR reactions were performed by initially denaturing cDNA at 95° C. for 3 min followed by 30 cycles of denaturing at 95° C. for 30 sec, annealing at 60° C. for 30 sec, polymerization at 72° C. for 30 sec and a final 10-min extension at 72° C. PCR products were loaded into 2% agarose gels containing 0.6 µg/mL ethidium bromide and run in Tris-acetate-ethylenediaminetetraacetic acid buffer for 45 min. The Alpha Innotech gel documentation station was used to observe PCR products.

Chimera Production

Stage-X White Leghorn chicken embryos were used to produce chimeras. Small injection windows were drilled into injection egg shells using a Dremel rotary tool. ciPSCs from black australorp chickens were transduced with Turbo-GFP Lentiviral Vector (Thermo Scientific Open Biosystems) before injection according to the manufacturer's instructions. ciPSCs were injected into the subgerminal cavity using a glass micropipette with pressure controlled microinjector (Parker Automation). Each embryo was injected with 10,000 cells. The window was sealed by using a hot glue gun after injection and eggs were incubated at 37.8° C.

Eggs were opened and dissected at day 5 and day 10 to determine if GFP positive ciPSCs successfully incorporated into chick embryos or allowed to hatch day 22. Hatched chicks were checked for feather chimerism (ciPSCs were derived from black australorp chickens, chicks from this breed have black down feathering at hatch enabling tracing of these ciPSC derived from this breed if transplanted into breeds that produce yellow down chicks such as White Leghorn).

DNA Isolation, PCR, and Sequencing

Chicks were sacrificed and brain, liver, muscle, heart and gonad tissues were collected for PCR analysis for the intergrated GFP gene.

DNA was isolated from five different organs using DNeasy kit (Qiagen) following the manufacturer's instructions. PCR reactions were performed by initially denaturing cDNA at 95° C. for 3 min followed by 30 cycles of denaturing at 95° C. for 30 sec, annealing at 58° C. for 30 sec, polymerization at 72° C. for 30 sec and a final 10-min extension at 72° C. GFP primer used in PCR are listed in Table 2, above.

Sequencing verification of GFP gene was performed by extracting DNA from agarose gels after electrophoresis. DNA was extracted from the agarose gels using the QIAquick Gel Extraction Kit (Giagen) per manufacturer's instructions. Purified DNA was sent to the Georgia Genomic Facilities for sequencing. The resulted sequence was compared by Blast in the NCBI database.

Results ciPSCs Generated by Minicircle Transfection Express Pluripotent Markers

Figure 16:
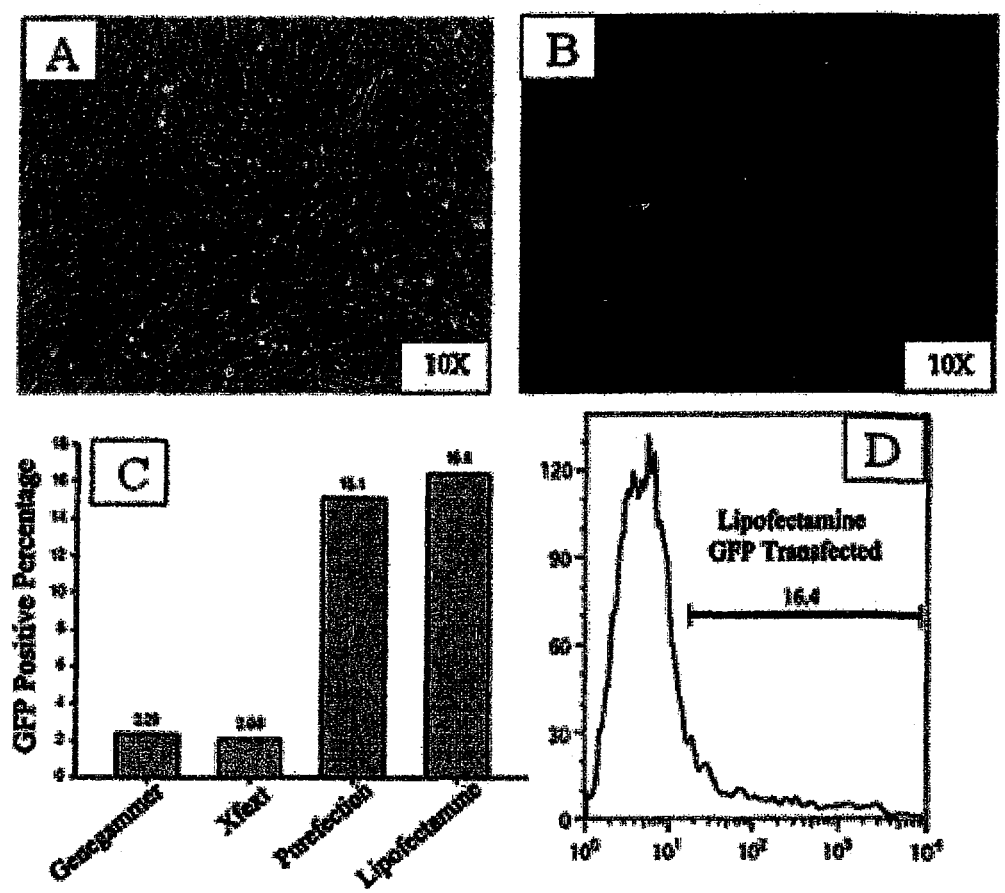
FIG. 16 shows the generation of chicken induced pluripotent stem cells (ciPSCs) from CEFs. (A) CEFs prior to addition of reprogramming factors (B) GFP expressed 72 hours post-transfection (C) Transfection efficiency comparison between different transfection reagents (D) Lipofectamine showed highest transfection efficiency.

Chicken embryonic fibroblasts (CEF; FIG. 16A) isolated from day-11 black australorp chicken embryos were transduced with the minicircle vector containing the POU5F1, SOX2, NANOG and LIN28 reprogramming genes and the GFP reporter using four different transfection reagents: lipofectamine, Xfect, purefection and genejammer. The cells were transfected a total of 3 times every other day over a 5 day period. The GFP expression reached a peak at 72 hours post-transfection (FIG. 16B). The lipofectamine transfected group showed the highest transfection efficiency with 16.4% population being GFP+, while transfection with genejammer, Xfect and purefection resulted in 2.3%, 2.1%, and 15.1% GFP+ cells respectively (FIG. 16. C, D). At day7, the cells were trypsinized and plated onto inactivated feeder cells in 20% KSR stem cell medium.

Figure 17:
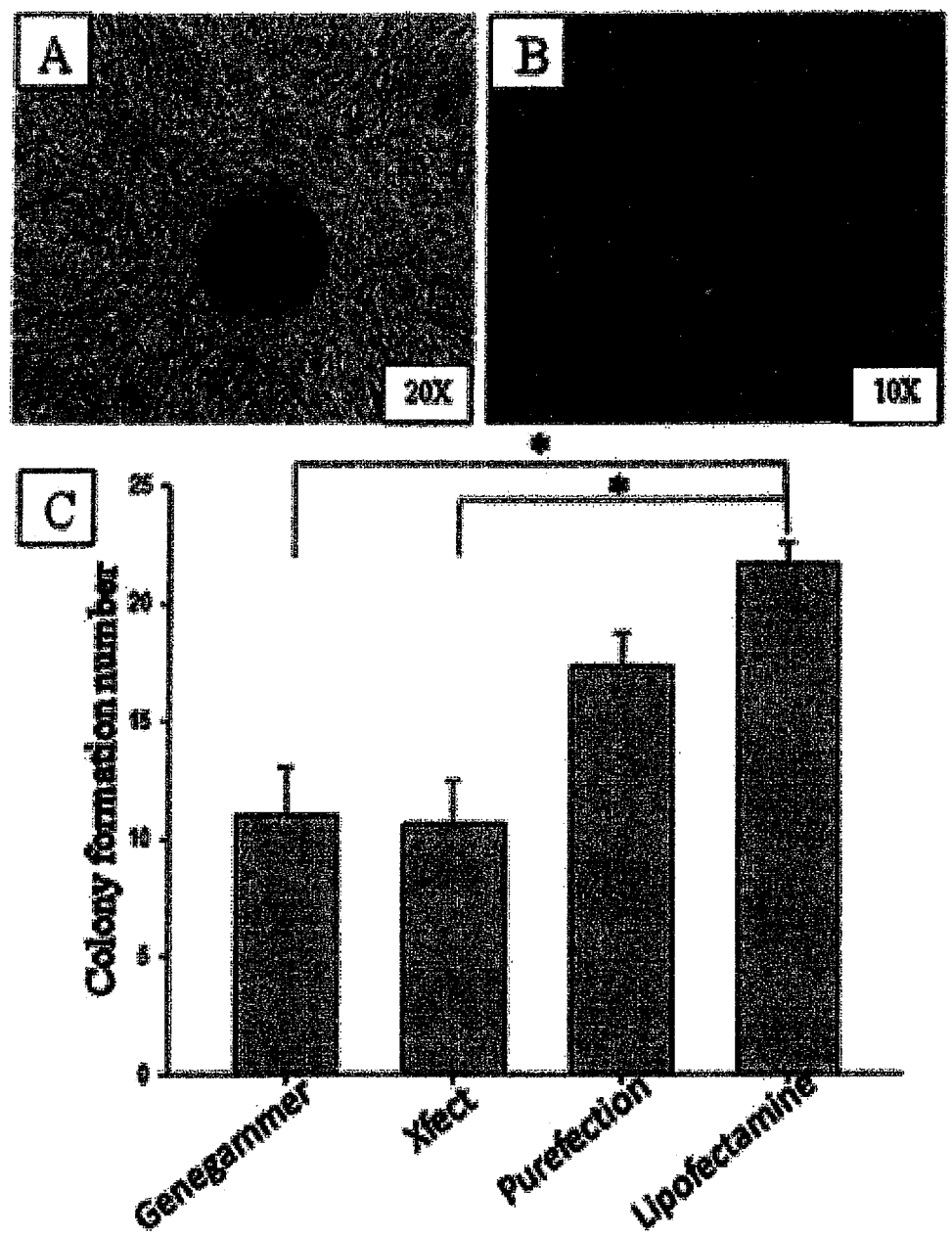
FIG. 17 shows the typical ciPSC colony formed in culture. (A) Reprogrammed CEFs showed defined borders at day 20 post-transfection (B) Typical ciPSC colonies were present in culture. (C) colony formation number counted and comparison between 4 different transfection reagents. *P<0.05 between 4 groups using different transfection reagents.
Figure 18:
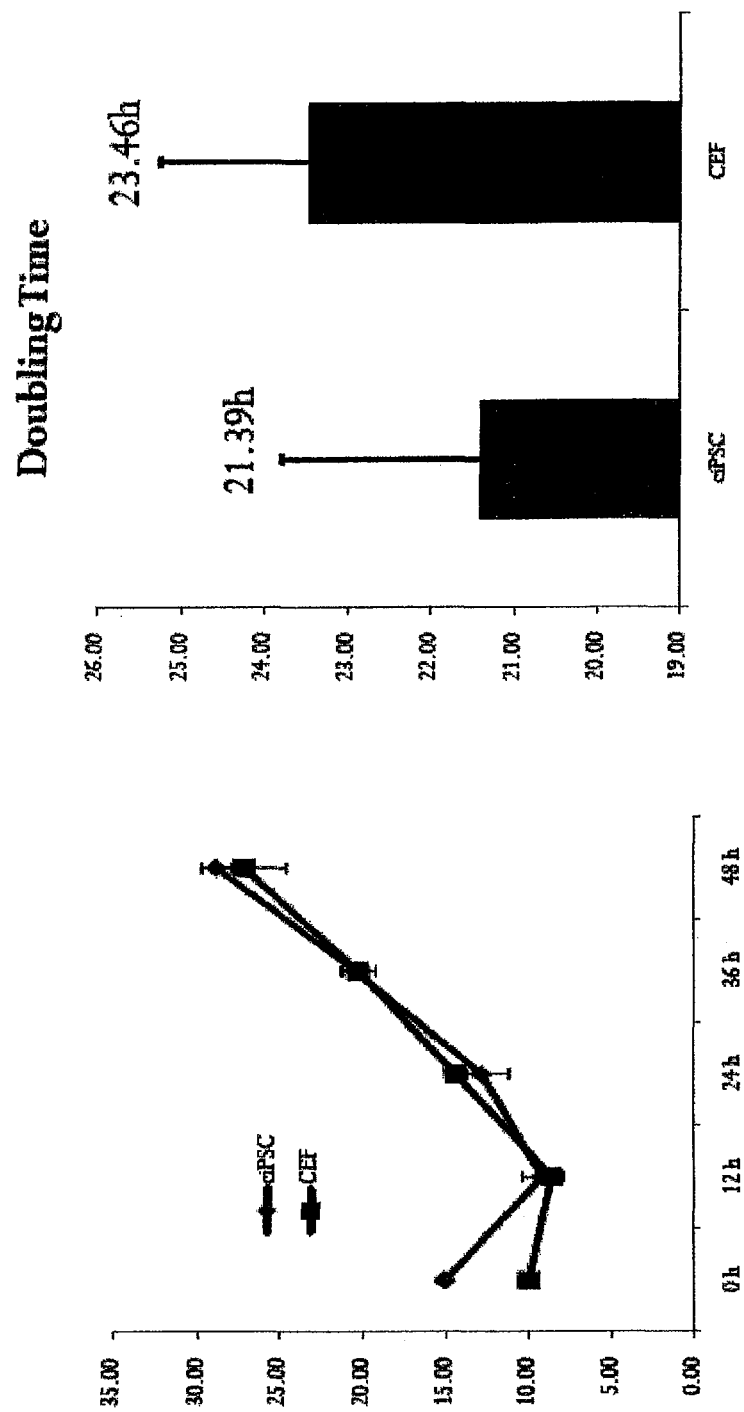
FIG. 18 shows that the rate of doubling the population of ciPSCs was only slightly greater than the doubling time for the somatic cell from the ciPSCs were derived.
Figure 19:
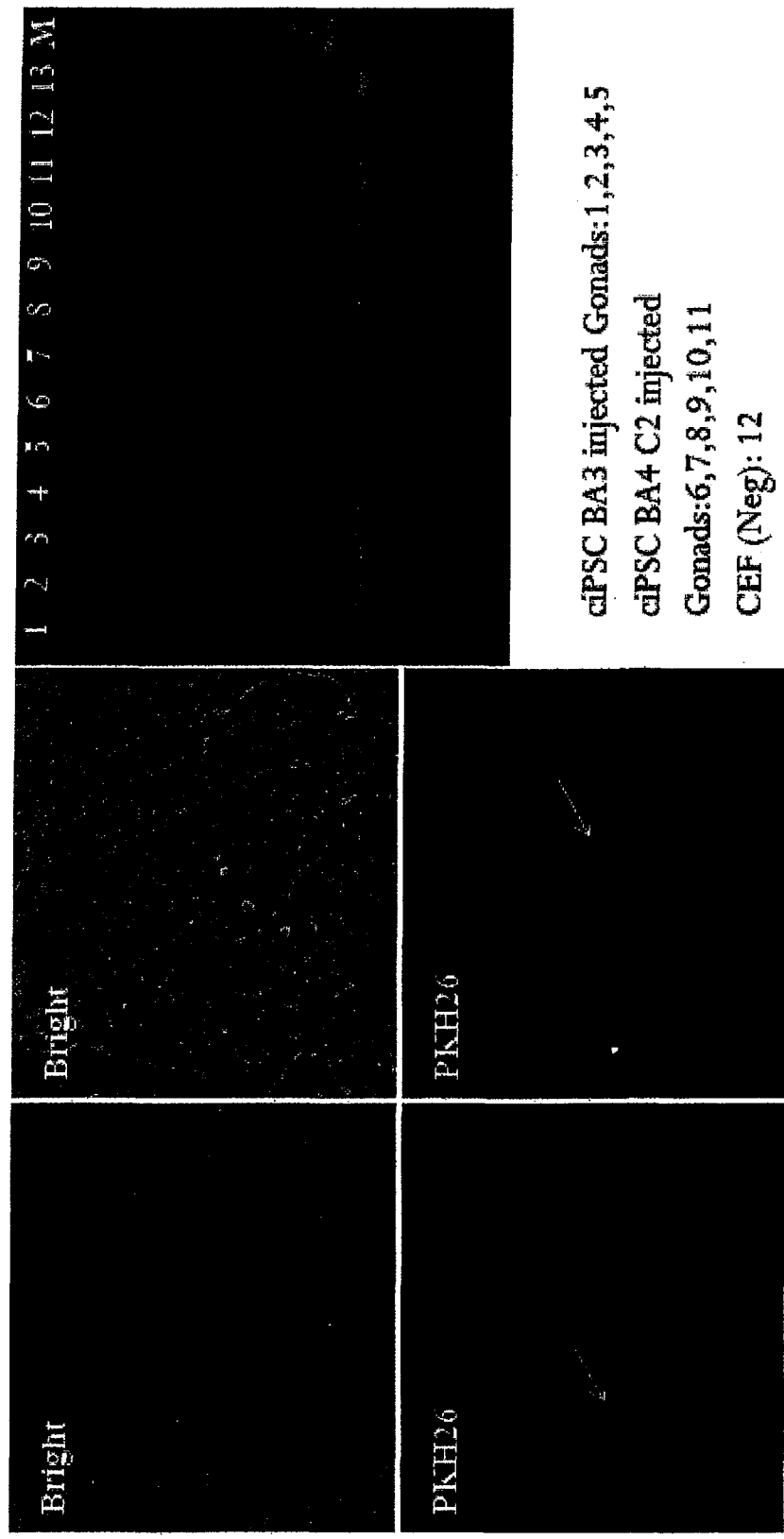
FIG. 19 shows that ciPSCs injected into gonads evidenced migration consistent with formation of gametes.

Compact colonies began to emerge on day 20 after transfection with defined borders (FIG. 17A). To determine the effect of transfection reagents on colony formation, the number of colonies was manually counted. Cells transduced with lipofectemine resulted in significantly (p-value <0.05) higher levels of colony formation (21.7±1.0) relative to cells transduce with genejammer (11±2.1) and Xfect (10.7±1.8). Transfection with purefection resulted in similar levels of colony formation (17.3±1.4) (FIG. 2C). The compact colonies were mechanically isolated and initially replated on feeder plates in 20% KSR medium. After passaging, ciPSC displayed morphological characteristics consistent with iPSCs including a colonial growth pattern with colonies forming highly refractive colonies with well defined boarders (FIG. 17B). At the single cell level, ciPSCs had a high nucleus to cytoplasm ratio and possessed large nucleoli indicative of a stem cell fate.

Further Examples (Third Set of References)

Avian (Chicken) Induced Pluripotent Germ Cells (aiPGCs)

The above examples, demonstrated that quail iPSCs could be generated from somatic cells using human pluripotency transcription factors and revealed that the regulatory mechanisms of pluripotency are conserved across species [22]. Therefore, it may be possible to reprogram chicken somatic cells using similar factors and chicken germ cell culture conditions to derive chicken germ cells [18,23]. Here we successfully generated PSCs by over expression of human transcription factors in chicken somatic cells. The PSCs express typical stem cell markers and were capable differentiating into all 3 germ layers. Moreover, these induced chicken PSCs when propagated in medium used to expand PGCs expressed important germ cell genes such as CVH and DAZL. Functional tests demonstrated that these newly reprogrammed chicken induced primordial germ cells (ciPGCs) were capable of migrating to the embryonic gonad after injection into stage 15 chicken embryos, an indication of germ cell fate. The capability to derive PGCs from somatic cells is the first step towards definitive GC studies in birds and provides a new strategy for conservation of endangered birds as well as a cell source for the study of toxicology in germ cell development.

Methods and Materials
Cell Culture and iPSC Derivation

The chicken embryonic fibroblast (CEF) cells used in the transduction were isolated from day-11 Barred Rock (BR) embryos and cultured in fibroblast medium [Dulbecco's modified Eagle's medium (DMEM) high glucose (Hyclone) with 10% fetal bovine serum (Hyclone), 4 mM L-glutamine (Gibco) and 1× Pen/strep (Gibco)] in 5% $CO_2$ at 37° C. One day before transduction, a total of $1.5 \times 10^5$ CEF cells were plated in one well of a 12-well plate. CEFs were transduced utilizing the viPS kit (Thermo Scientific) with lentiviruses containing the human stem cell genes POU5F1, NANOG, SOX2, LIN28, KLF4, and C-MYC at an multiplicity of infection (MOI) of 10 and in the presence of 1× TransDux (System Biosciences). Twenty four hours after transduction, the transduced cells were replated at a ratio of 1:10 onto 1×100 mm plate pre-seeded with mitomycin inactivated mouse embryonic fibroblast (MEF) in cKSR medium [DMEM/F12 (Gibco), supplemented with 20% knockout serum replacement (KSR; Gibco), 2 mM L-glutamine (Gibco), 0.1 mM nonessential amino acids (Gibco), 1× Pen/strep (Gibco), 0.1 mM β-mercaptoethanol (Sigma-Aldrich), and 10 ng/mL basic fibroblast growth factor (bFGF; R&D Systems). Medium were conditioned in MEF for 1 day before use.] or cKO medium [KO-DMEM (Invitrogen) containing 4 ng/mL bFGF, 7.5% defined FBS (Hyclone), 2.5% chicken serum (Sigma), 1× Pen/strep (Gibco), 1× GlutaMAX (Gibco), 1× GS nucleoside supplement (Millipore) and 0.1 mM β-mercaptoethanol, with 10% of the KO-DMEM preconditioned in BRL cells (ATCC) for 3 days before use]. The presumed chicken iPSCs were manually isolated by using pasteurized glass pipette under stereomicroscope 7 days after transduction and replated onto fresh MEF feeder cells. Cells were passaged every 4 to 5 days by manual isolation or tripsinization.

Alkaline Phosphatase (AP) and Periodic Acid Schiff's (PAS) Staining

AP staining was conducted by using VECTOR Red Alkaline Phosphatase Substrate Kit per manufacturer instructions. Briefly, culture medium was removed and then the cells were gently rinsed once with Tris-HCl buffer (pH8.3) and then incubated with the pre-mixed staining solution at room temperature for 20 min. At the end of incubation, the cells were gently rinsed with Tris-HCl twice. Then cells were overlaid with PBS and cells were imaged on the microscope.

PAS staining was conducted by using Periodic Acid Solution and Schiff's Reagent (Sigma) per manufacturer instructions. Briefly, cells were fixed in a culture dish with 4% paraformaldehyde (PFA) for 5 min and then washed with PBS 3 times. Periodic Acid Solution was then added into the plate and incubated at room temperature for 5 min. Then the cells were rinsed with PBS 3 times and Schiff's Reagent was added to the plate and incubated at room temperature for 15 min. The cells were gently rinsed with PBS 3 times and cells were imaged on the microscope.

Embryoid Body (EB) Formation and Differentiation

EBs were prepared in cKO medium without bFGF by using an AggreWell plate (Stemcell Technologies). A total of $2.4 \times 10^6$ chicken PSCs were plated in each well of the AggreWell plate, which is equivalent to 2,000 cells per microwell. After 24 h, the aggregates were harvested by gentle pippeting and then transferred to a petri-dish and continued to culture for 6 days. EBs were collected for RNA isolation and cDNA synthesis. PCR was performed to detect the differentiation using primers listed in Table 2. For immunocytochemistry assay, EBs were replated in 4-well chamber slide and cultured for 3 days. Then the cells were fixed in 4% PFA for use in immunostaining.

DNA, RNA Isolation and PCR

DNA was isolated using DNeasy Blood & Tissue Kit (Qiagen). RNA isolation was conducted using RNeasy QIAprep Spin miniprep Kit (Qiagen) following manufacturer's instructions. cDNA was synthesized using Super-Script VILO cDNA Synthesis Kit (Invitrogen). PCR and RT-PCR was performed using primers listed in Table 2, above. Quantitative PCR (qPCR) was performed using 7500 Real-Time PCR System and TaqMan certified primers (Life Technologies) and CEF was used as a control cell line and GAPDH as an endogenous control. All the samples were replicated 3 times.

Immunocytochemistry and Flow Cytometry

Cells were fixed in 4% PFA for 15 min and blocked in 4% horse serum for 45 min. Cells were then incubated with primary and then secondary antibodies prepared in blocking solution at room temperature for 60 min, respectively. The primary antibodies used in this study were POU5F1 (R&D Systems), SOX2 (R&D Systems), SSEA1 (Developmental Studies Hybridoma Bank), EMA1 (Developmental Studies Hybridoma Bank), HuC/D+(Invitrogen), SOX17 (Santa Cruz), alpha smooth muscle actin (αSMA) (Santa Cruz), SOX1 (R&D Systems), DAZL (gift from James Petitte, NCSU), VASA (DDX4, Abcam) and CXCR4 (ECM Bioscience). Secondary antibodies were all from Invitrogen. Imaging for immunocytochemistry was done by using an Ix81 with Disc-Spinning Unit (Olympus) and flow cytometry analysis was done using a flow cytometer Cyan (Beckman Coulter).

Cell Injection and Migration

Before injection, cells were labeled with PKH26 (Sigma) according to the manufacturer's instruction. White leghorn chicken embryos at stage 15 were used as a host for the injection. A window 1-cm diameter was made on the blunt end above the air cell to expose the embryos. A total of $1 \times 10^4$ cells were loaded into a micro glass needle and injected into the vasculature system of each embryo. The window was sealed by applying 2 layers of parafilm. The injected embryos were incubated for 6 days and then euthanized to isolate the gonads under a stereomicroscope. Images of gonads were captured under an inverted microscope.

Results

Pluripotent Chicken Stem Cells Derivation from Fibroblasts

Figure 21:
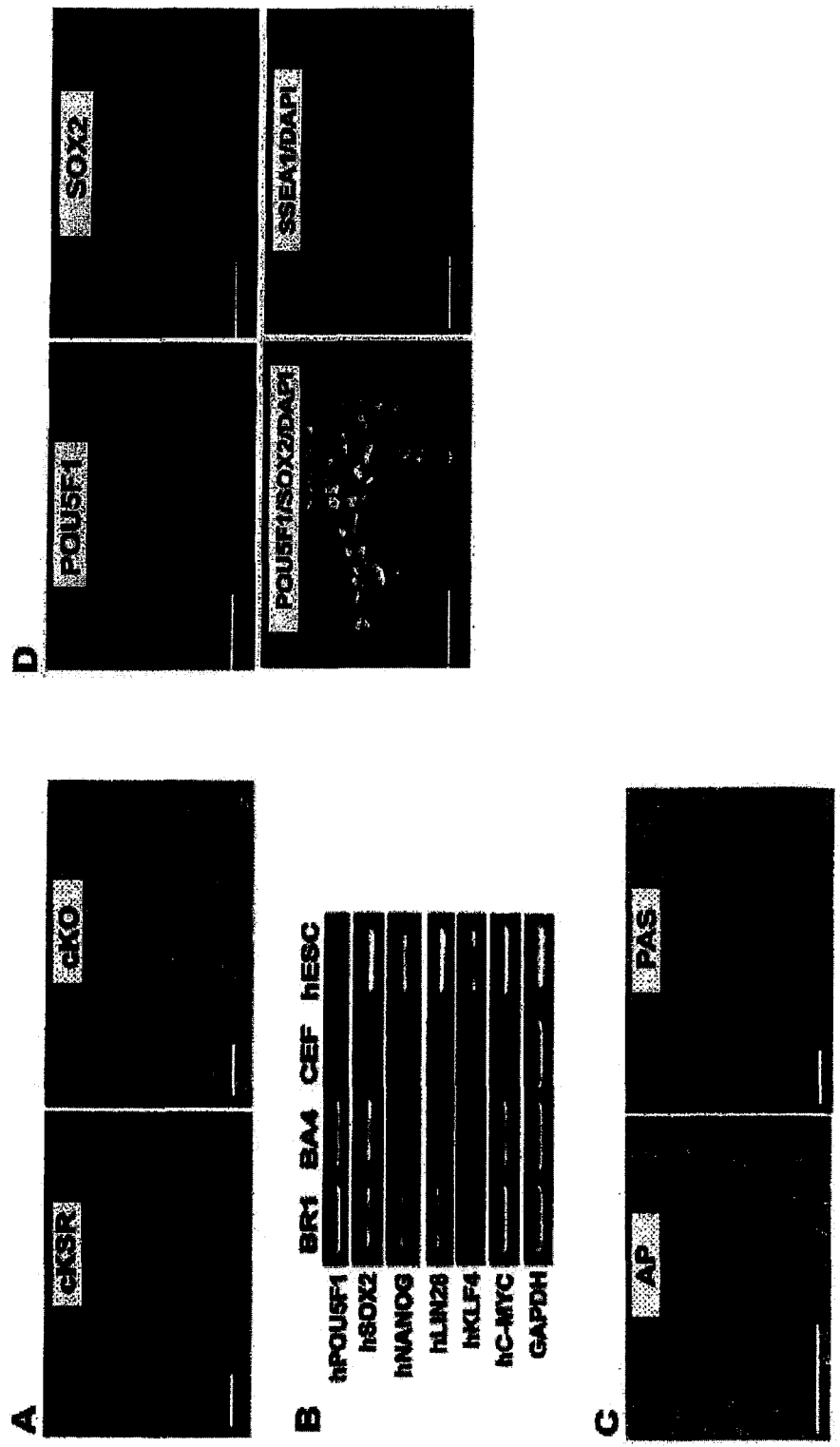
FIG. 21 shows that reprogramming of CEF into cPSC requires 5 factors and cKO medium for stable propagation. Chicken embryonic fibroblasts were transduced with human stem cell factors and replated in cKSR medium and cKO medium formed cPSC colonies in 7 days (A), but cKO medium was required to establish stable cPSC lines. Incorporation of reprogramming factors varied in the different lines (B), but only the 5-factor line was immortal (>40 passages). The established cPSCs were positive for AP and PAS (C). The five factor cells were positive for pluripotent markers POU5F1, SOX2 and SSEA1 (D). Flow cytometry confirmed that 70.8% of cKO-derived cPSCs were POU5F1 positive and 82.5% were SSEA1 positive, while the POU5F1 and SSEA1 positive cells were reduced to 39.0% and 74.9%, respectively, after replating in cKSR medium (E). Scale bar A, C: 200 μm; D: 50 μm.
Figure 21:
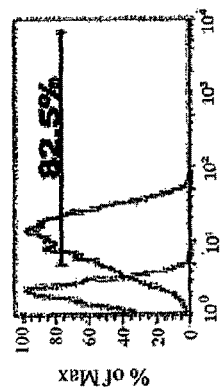
Figure 21:
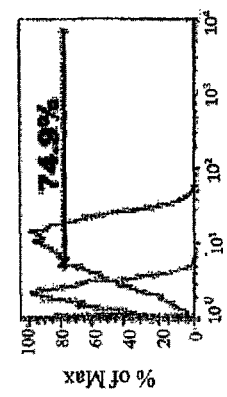
Figure 21:
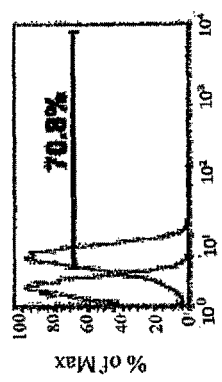
Figure 21:
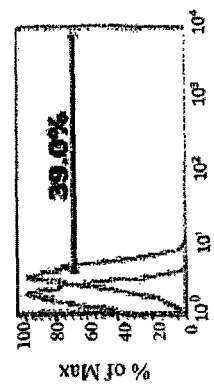

To generate pluripotent stem cells, chicken embryonic fibroblasts isolated from 5 different Barred Rock (BR) or 5 unique Black Australorp (BA) embryos were transduced with 6 human reprogramming factors (hPOU5F1, hSOX2, hNANOG, hLIN28, hKLF4 and hC-MYC). Each factor was individually packaged in a separate lentiviral vector. After 24 hours post-transduction, cells were replated on an inactivated MEF feeder layer. Putative chicken pluripotent stem cells (cPSCs) were cultured in cKSR medium following a previously developed protocol utilized to generate quail iPSC [24]. The cPSC colonies emerged as early as day 5 and were manually selected for propagation on day 7 after transduction (FIG. 21A). However, 8 of the 10 lines generated ceased to proliferate by passage 10. The remaining 2 lines demonstrated high levels of proliferation, but did not express the pluripotent markers POU5F1 or SSEA1 (data not shown) and were not utilized in further studies.

We then attempted the reprogramming process utilizing cKO medium which has previously been optimized to maintain chicken primordial germ cells (PGCs) in extended culture [18]. After reprogramming as before, small colonies containing iPSC-like cells were observed 5 days after replating of the transduced CEFs in cKO medium. Cells were manually isolated from day 7 to 10 (FIG. 21A). Two lines (BA and BR) of CEFs were transduced with human stem cell factors and both successfully produced cPSCs in this culture system. However, the BA line ceased to grow at passage 10 while the BR line has been successfully propagated up to 40 passages. PCR results revealed that the BA line had only 3 human genes incorporated (POU5F1, SOX2 and C-MYC), while the BR line had 5 (hPOU5F1, hSOX2, hNANOG, hLIN28 and hC-MYC) of the 6 human reprogramming genes successfully incorporated (FIG. 21B). This suggested that additional factors may be needed to fully reprogram the chicken somatic cells. An additional round of transduction of the BA line generated a 5-factor cPSC line that had a similar proliferation competence as the BR line. Morphologically, the established cPSC colonies in cKO medium were loosely attached to the feeder layer and cells of these colonies demonstrated 3-D structures (FIG. 21A). cPSC cultured in cKO are highly positive for alkaline phosphatase (AP) and periodic acid Shift's staining (PAS, FIG. 21C). Immunocytochemistry revealed that these cells are positive for POU5F1, SOX2 and SSEA1 (FIG. 21D) indicating pluripotency. Flow cytometry results showed that SSEA1 and POU5F1 positive cells represent 82.5% and 70.8%, respectively, of the whole population (FIG. 21E). To determine if cells cultured in cKO medium were less prone to spontaneous differentiation than cells in cKSR medium, we cultured the cKO medium-derived ciPSCs in cKSR medium. This resulted in a reduction of SSEA1 and POU5F1 positive cell down to 74.9% and 39.0%, respectively (FIG. 21E). Thus in the following experiments we used cKO as the preferred culture medium.

cPSCs Express Endogenous Pluripotent Genes

Figure 22:
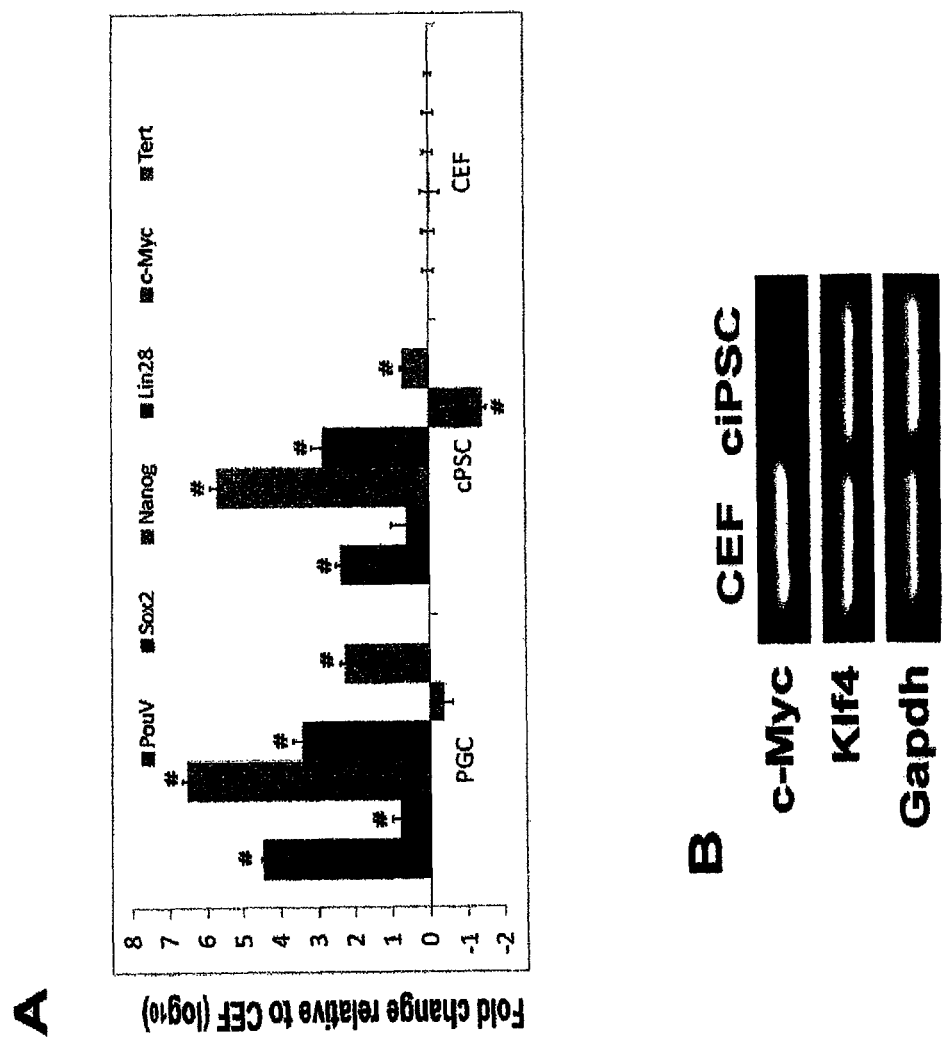
FIG. 22 shows the reactivation of endogenous pluripotent genes in cPSCs. Quantitative PCR showed that the endogenous pluripotent genes PouV, Sox2, Nanog, Lin28 and Tert were highly up-regulated, while c-Myc was down regulated in cPSCs. This indicates a significant difference relative to CEFs: # P<0.01. (A). RT-PCR revealed that endogenous c-Myc and Klf4 were expressed in the parent CEF cells (B).
Figure 23:
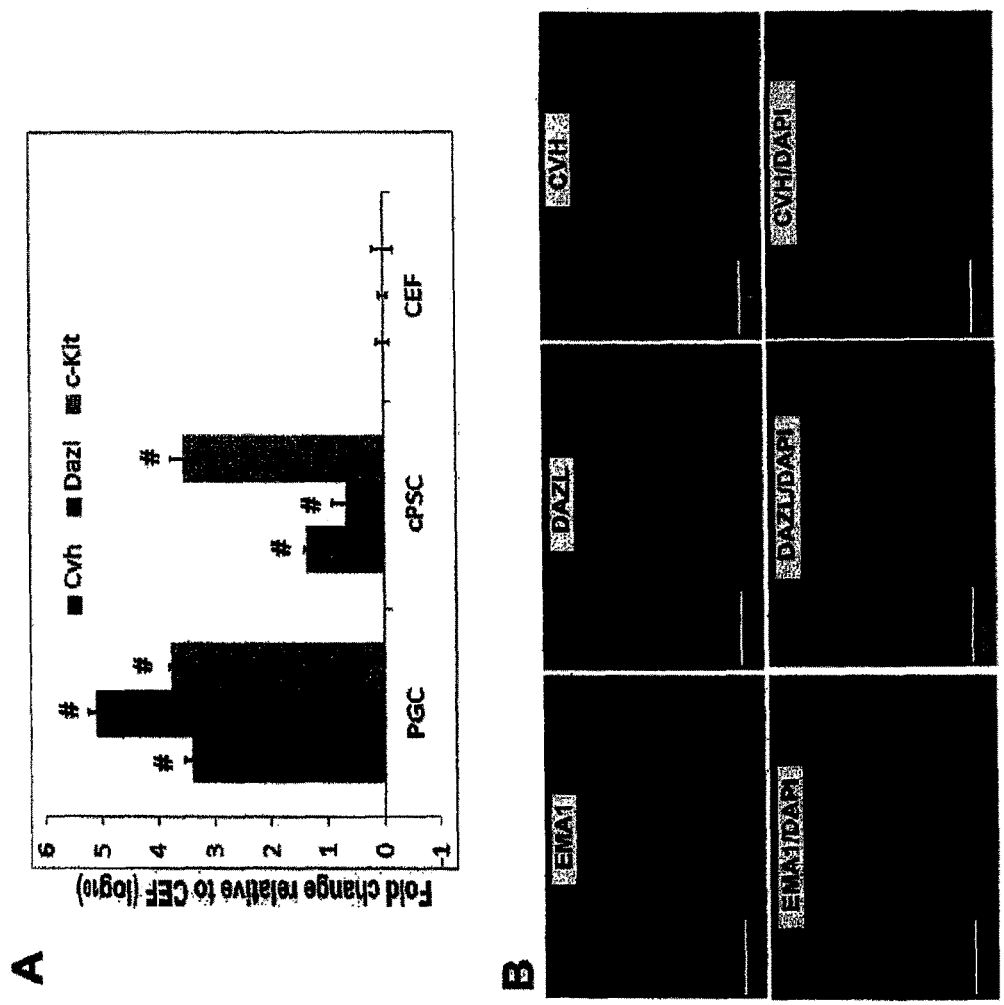
FIG. 23 shows that the cPSCs express germ cell markers. Quantitative PCR by using PGCs as positive control and CEF as negative control revealed that the germ cell related genes Cvh, Dazl and c-Kit were up regulated in cPSCs compared to CEFs. This indicates a significant difference relative to CEFs: #P<0.01. (A). Immunocytochemistry demonstrated that germ cell related markers EMA1, DAZL and CVH were highly positive at the protein level (B). Flow cytometry confirmed that 65.0% of the ciPSCs are positive for EMA1, 92.0% for DAZL and 93.4% for CVH (C). Scale bar B: 50 μm.
Figure 23:
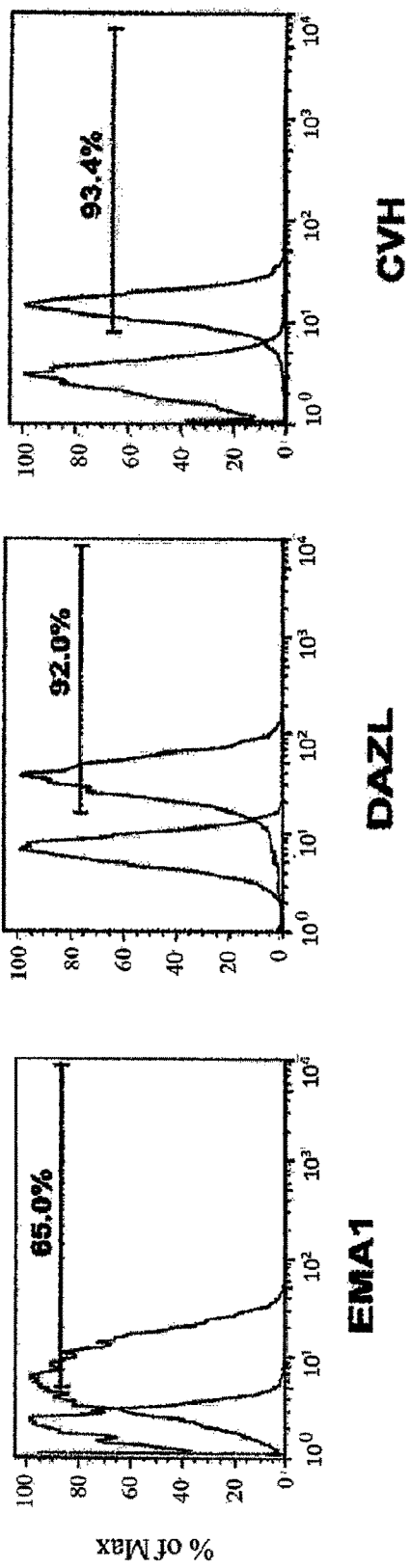

Previous reports indicated that ectopic expression of transcription factors resulted in the reactivation of the endogenous pluripotent genes, which was critical for a complete induced pluripotency during cellular reprogramming [25]. Using quantitative PCR for chicken specific TaqMan primers, chicken PouV, Sox2, Nanog and Lin28 were highly up-regulated in cPSCs, which indicated that endogenous pluripotent machinery was triggered by the over expression of the exogenous genes (FIG. 22A). The telomerase reverse transcriptase (Tert) was also up-regulated in ciPSCs, indicating the acquisition of the immortality in these cells (FIG. 22A). Unexpectedly, the chicken c-Myc was found to be down regulated in ciPSCs relative to CEF cells (FIG. 22A) and this finding was confirmed by RT-PCR. This c-Myc result may be due to the fact that this was highly expressed in the parent cell line CEFs and not further increased when the exogenous gene was added (FIG. 22B). The results of RT-PCR also revealed that Klf4 was highly expressed in CEF, comparable to that observed in cPSCs (FIG. 22B). These results indicated that ectopic c-Myc and Klf4 expression might be dispensable in derivation of cPSCs.

cPSCs Express Germ Cell Specific Markers cPSCs were derived in a cKO medium that was optimized for germ cell maintenance and we, therefore, examined cPSCs for shared morphology and gene expression with cultured PGC. Quantitative RT-PCR expression of chicken VASA homologue (Cvh) and deleted in azoospermia (DAZL), although lower than in PGCs, were both highly up-regulated in cPSCs (FIG. 23A) and c-Kit expression in cPSCs was comparable to PGCs. We then further characterized the expression of germ cell related proteins by immunocytochemistry and flow cytometry. cPSCs were positive for EMA1, DAZL and CVH at the protein level (FIG. 23B). Flow cytometry confirmed that 65% of the cPSC were positive for EMA1, 92.0% and 93.4% for DAZL and CVH, respectively (FIG. 23C). Moreover, pluripotency in cPSCs was better maintained in the PGC medium cKO instead of cKSR medium (FIG. 21E). These results indicated that cPSCs derived in this study acquired a germ cell fate and are hence forth called chicken iPGCs.

iPGCs are Capable of Differentiation into all 3 Germ Layers In Vitro

Figure 24:
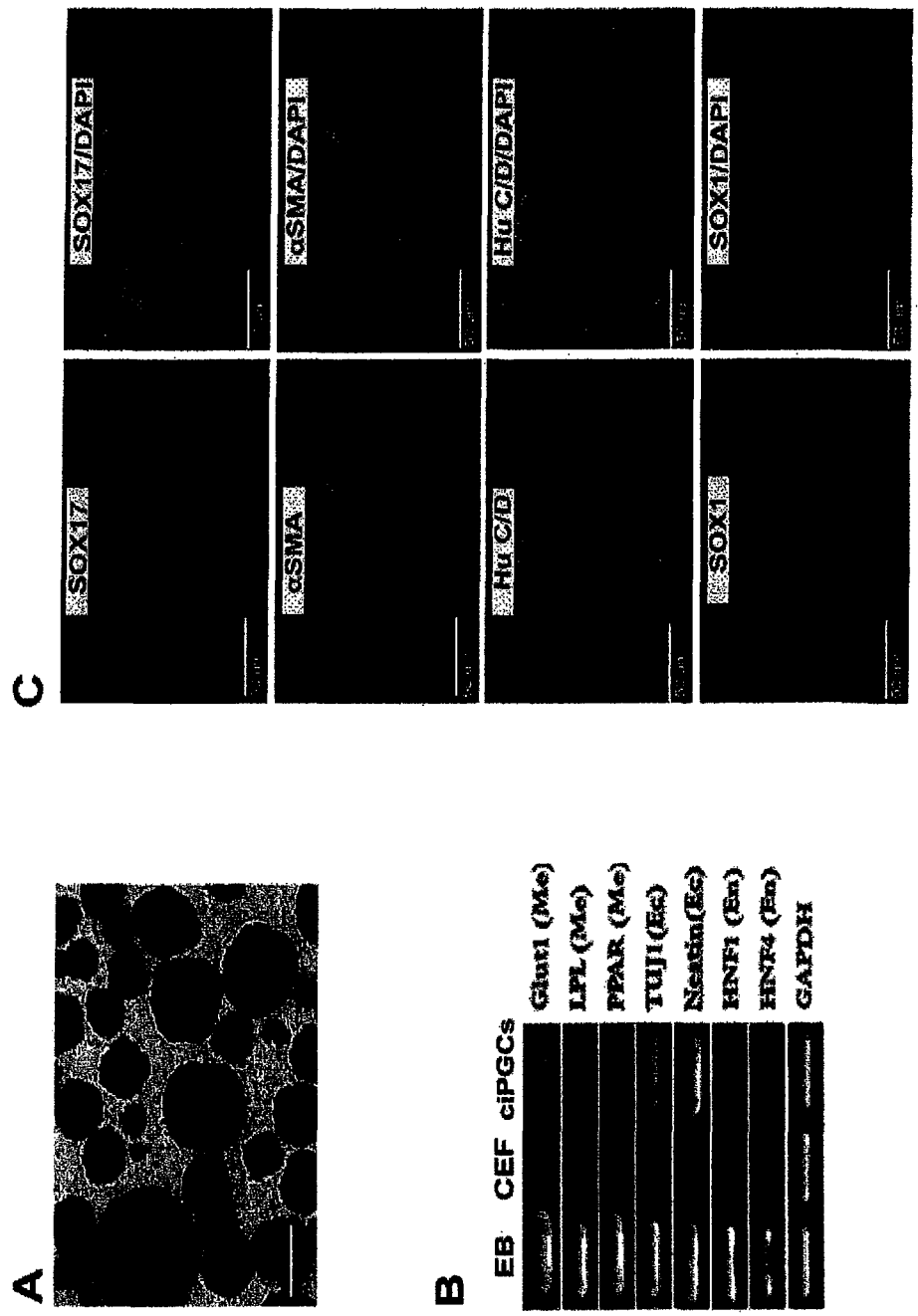
FIG. 24 shows that iPGCs are capable of differentiation into all 3 germ layers. iPGCs formed compact EBs after suspension culture for 6 days in differentiation medium (A). Expression of mesoderm (Me), ectoderm (Ec) and endoderm (En) genes were detected in the EBs using RT-PCR (B). After replating of EBs and differentiation for an additional 3 days, cells positive for endoderm (SOX17), mesoderm (αSMA) and ectoderm (Hu C/D and SOX1) were detected by immunocytochemistry (C). Scale bar A: 200 μm, C: 50 μm.

Chicken PGCs have previously demonstrated a high level of plasticity in vitro and are capable of generating cells from all 3 germ layers [26,27] in vitro. To determine if iPGCs demonstrate the similar potential, these cells were subjected to in vitro embryoid body (EB) differentiation. The recovered aggregates formed compact EBs after suspension culture for 6 days in differentiation medium (FIG. 24A). RT-PCR analysis showed mesoderm (Glut, LPL and PPAR), ectoderm (TUJ1 and NESTIN) and endoderm (HNF1 and HNF4) genes were highly expressed in iPGC-derived EBs, but were negative in CEFs (FIG. 24B). Low levels of differentiation lineage marker gene expression was also detected in undifferentiated iPGCs, which indicated some cells were undergoing spontaneous differentiation (FIG. 24B). To induce further differentiation, the recovered EBs were replated in Matrigel coated 4-well chamber slides and cultured for an additional 3 days. Results of the immunocytochemistry showed that plated EBs were capable of differentiating into endoderm (SOX17), mesoderm (αSMA) and ectoderm (Hu C/D and SOX1) cell types (FIG. 24C), demonstrating that in vitro iPGCs possessed developmental plasticity. It is noted that when iPGCs are injected in vivo, they migrate to gonads in the injected animal where they can form gametes (ova and sperm cells).

iPGCs Migrate to the Embryonic Gonad In Vivo

Figure 25:
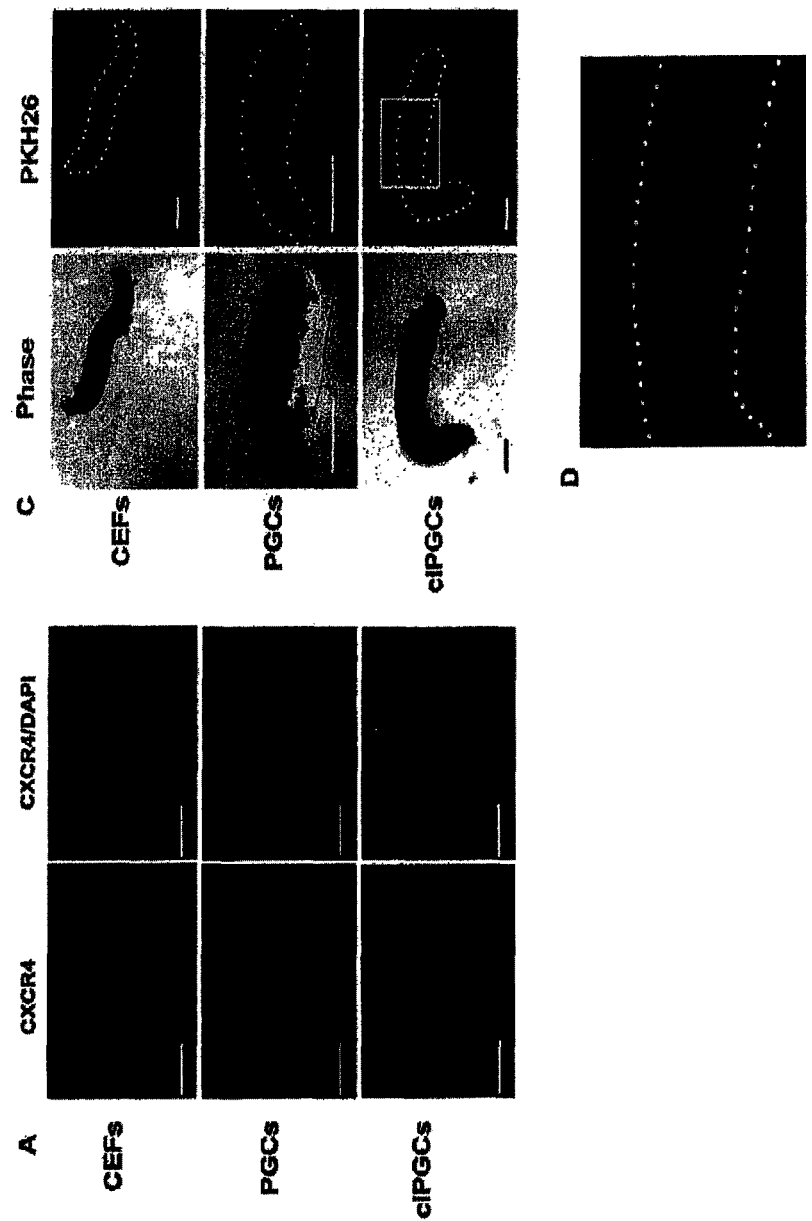
FIG. 25 shows that iPGCs are capable of migrating to the embryonic gonad. Immunocytochemistry showed that CEFs were CXCR4 negative while both PGCs and iPGCs were positive (A). Flow cytometry confirmed that 51% of the ciPSCs were CXCR4 positive. (B). Cells labeled with PKH26 (red) were injected into vasculature system of stage 15 chicken embryos and the embryonic gonads were isolated 6 days after injection. No PKH26 positive CEFs were found in the embryonic gonad, while significant migration was found in embryos injected with PGCs and iPGCs (C). A high-magnification view of the boxed area in FIG. 5C showed significant cells present in the embryonic gonad injected with iPGCs (FIG. 5D). Scale bar A: 50 μm; C: 400 μm.
Figure 25:
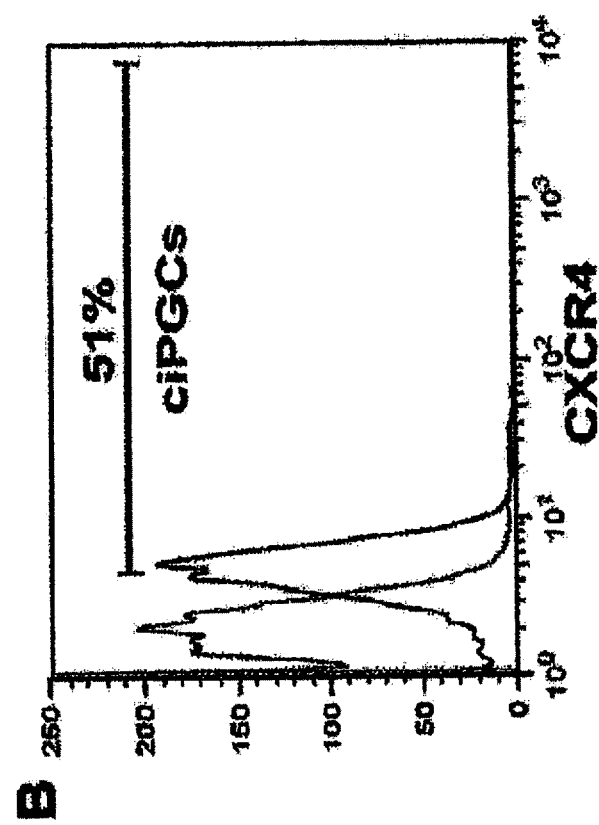

During embryonic development, chicken PGCs migrate through the vasculature system to the gonads at developmental stages 15 to 17 [28]. Germ cell migration has previously been demonstrated to be orchestrated by the SDF-1/CXCR4 chemokine signaling pathway making it important to determine if iPGCs express CXCR4 [29-32]. Results of immunocytochemistry showed that CEFs were negative for CXCR4 while both in vivo derived PGC positive control cells and iPGCs were positive (FIG. 25A). Flow cytometry confirmed that 51% of ciPSCs were positive for CXCR4 (FIG. 25B). To determine the migratory potential of these cells, we labeled the iPGCs, PGCs and CEFs with PKH26 and injected them into the vasculature system of stage 15 chicken embryos. All 10 embryos injected with PGCs and 13 out of 18 embryos injected with iPGCs exhibited migration of exogenous cells to the embryonic gonads. No CEFs were found in the gonads of the injected embryos (9 embryos) (FIG. 25C). Although we also found sporadic PKH26 cells in tissues other than gonads in iPGCs and PGCs injected embryos, most of them were located in the gonad or the mesentery tissues adjacent to the gonads, which has been documented as the migration route of PGCs before entering the developing gonad [28]. These data demonstrate that the iPGCs derived in this study acquired a germ cell-like fate in vitro and are capable of migration to the embryonic gonads.

Discussion

In the present application, the inventors have demonstrated for the first time in the avian species the successful derivation of iPGCs from a somatic cell line by cellular reprogramming. These cells resemble PGCs in gene expression and protein profiles and are capable of migration to embryonic gonads after injection into stage 15 chicken embryos. This advance represents the first step towards generating germ line chimeric individuals derived from somatic cells. As germ cells are responsible for passing genetics from one generation to the next, the capability to generate PGCs from somatic cells offers a potentially new strategy for the conservation of endangered birds. This approach also provides scientists a new cell tool to gain insight into the biology of the germ cell development or for PGC studies such a developmental reproductive toxicology using the avian model.

iPGCs expressed a number of the key germ cell markers including CVH, DAZL and C-KIT, which are germ cell specific or highly enriched markers. VASA (or DDX4) is the CVH homologue and is widely conserved and has been demonstrated to be a definitive germ cell marker in drosophila, xenopus, mice and human [33-36]. Similarly, the chicken homologue Cvh has also been found to be specifically expressed in PGCs [37]. In fact, overexpression of Cvh has been demonstrated to drive chicken ESCs to a germ cell fate [38]. Dazl, a member of the Daz gene family which encodes RNA-binding proteins, is also specifically expressed in germ cells and required for germ cell development in diverse organisms [39]. Loss of DAZL expression has been closely associated with aberrant gametogenesis and infertility and again the overexpression of this gene in ESCs has lead to the direct reprogramming of ESCs into PGCs, indicating its prominent role in germ cell development [40-42]. c-Kit is a key regulator of PGC development and binding of c-Kit to its ligand activates multiple downstream signaling events (such as MEK/MAPK) and promotes growth and survival of PGCs [43]. Here high expression of Cvh, Dazl and c-Kit in the iPGCs indicates that the ectopic expression of the transcription reprogramming factors not only induced the pluripotent network in CEFs, as indicated by the up-regulation of the endogenous genes. Reprogramming also triggered the germ cell related signaling pathway and resulted in a germ cell fate in these somatic cells when placed in PGC culture conditions. PGCs possess unique migratory properties in early embryonic development, and the signaling by chemokine receptor CXCR4 and its ligand SDF-1 was reported to be responsible for this migration in mammals as well as in avians [32]. We found that CXCR4 was expressed in PGCs and iPGCs, but absent in CEFs. PGCs and iPGCs injected into stage 15 chicken embryos resulted in significant migration to the embryonic gonads. Chicken ESCs are negative for the germ cell associated CXCR4 and are unable to migrate to the putative gonad in a similar manner to PGCs [44]. In total, the cells derived in this study resemble PGCs in gene transcription, protein cell morphology and in vivo characteristics (Table 1), and thus should be considered iPGCs.

Maintenance of the pluripotency of PGCs in vitro has been challenging and little is known about its underlying mechanism. bFGF has been demonstrated to play a key role in this process by activating the MEK/ERK cell signaling pathway and stimulates the proliferation of PGCs [45]. iPGCs in the present study were derived and maintained in cKO that contains bFGF. If bFGF is removed from cKO media iPGCs lose their 3-D colony morphology and are loosely attached to the feeder layer, but then become more adherent with some invading the feeder layer, a phenomena similar in the culture of chicken ES cells [46] and the conversion of PGCs into EGCs in the mouse [18]. However, cKSR medium used for human or chicken ESC [47] culture also contains bFGF, but failed to maintain the pluripotency in iPGCs as evidenced by a significant decrease of POU5F1 positive cells after culture in this medium (FIG. 21E). Additional factors in the cKO medium such as the those secreted by the BRL cells in the conditioned medium (cKO medium) are believed to be critical for the maintenance of avian pluripotent cells [46].

TABLE 3

Pluripotent markers expressed in chicken ESCs, PGCs and iPGCs

| ESC or PGC common and specific marker | Chicken ESC | Chicken PGC | ciPGC |
|---|---|---|---|
| AP | Positive[23, 44] | Positive[26] | Positive |
| PAS | Positive[47] | Positive[48] | Positive |
| SSEA1 | Positive[23, 44] | Positive[48] | Positive |
| EMA1 | Positive[23, 44] | Positive[48] | Positive |
| POUV | Positive[22] | Positive[37] | Positive |
| NANOG | Positive[22] | Positive[37] | Positive |
| DAZL | Negative[38] | Positive[49] | Positive |
| CVH | Negative[37, 38] | Positive[37] | Positive |
| CXCR4 | Negative/Low[38] | Positive[32] | Positive |
| C-KIT | N/A | Positive[50] | Positive |

As previously observed in mammals, ectopic expression of the master reprogramming transcription regulators could trigger the endogenous pluripotent network [51]. Successful induced pluripotent chicken cells in the current study confirmed that this process is widely conserved across vertebrates. The tumor associated gene c-Myc was reported to be essential in regulation of the pluripotency and cell cycle in pluripotent stem cell lines [51,52]. However, our findings showed that, although the endogenous genes (e.g. PouV) were highly up-regulated by the ectopic transcriptional factors, the c-Myc was significantly down regulated in chicken iPGCs compared to its parent somatic cells. We also found that expression of c-Myc in PGCs was lower than that observed in CEF cells (FIG. 22A). This suggests that the exogenous c-Myc gene may not be required to induce and maintain pluripotency in CEF-generated chicken iPGC, and donor CEF c-Myc levels may be sufficient. However, exogenous c-Myc may be required in other cell types that are reprogrammed, perhaps in adult tissue that would have lower endogenous c-Myc expression. Therefore, results may vary depending on the original cell type that is reprogrammed. Another tumor related gene Klf4 is a widely used reprogramming factor and when overexpressed can change prime state EpiESCs to the naïve state [53]. Interestingly, the human KLF4 failed to be incorporated in any of the chicken iPGC lines in the present study and is similar to the quail iPSCs we isolated previously [24]. A recent report also revealed that although the exogenous Klf4 constructed in a polycistronic vector was incorporated into the chicken cell genome and expression was detected in the second passage after transduction, it was completely shutdown in the fifth passage and endogenous Klf4 was not up-regulated to CEF cell levels [54]. We observed that endogenous chicken Klf4 was highly expressed in chicken iPGCs as well as in the parent cell line CEFs. These observations indicate that ectopic Klf4 expression might be dispensable during later stages of the cellular reprogramming and induced pluripotency in avian cells, since Klf4 was not incorporated into the iPGCs. Taken together, a combination of exogenous POU5F1, SOX2, NANOG, LIN28 and possibly additional C-MYC, seems to be sufficient for iPGC induction from somatic cells in avian species.

For decades, significant effort has been spent seeking and developing practical means for endangered bird conservation with little avail, since the total number of species is still declining [19]. A recent report revealed that functional gametes could be produced from interspecies transplantation of PGCs, suggesting a new strategy for conservation of endangered birds by using a domestic host [55]. However, this process still requires the sacrifice of endangered embryos for the collection of PGCs. Direct derivation of iPGCs from somatic cells would circumvent the sacrifice of embryos for PGCs isolation and facilitate the implementation of this strategy. Given that iPGCs can be cryopreserved; and therefore, stored and shipped around the world, captive animal breeding programs might use this technology to introduce genetic diversity into isolated populations or preserve valuable genetics from animals that die.

Avian developmental models are used extensively in research. New insight into neural development [56], ovarian cancer [57] and eye defects [58] have occurred because of the ease of manipulating and observing altered phenotypes in developing avian embryos. However, the lack of a gene editing platform in this species has been a hurdle for researchers. Availability of iPGCs would allow complex genetic modification at the cellular level and thus would significantly advance the use of this model in research. Genetic engineering in chickens would also be of significant interest in the production of transgenic birds that carry specific traits with agricultural or pharmaceutical importance.

In the present application, the inventors have demonstrated for the first time the generation of chicken iPGC from somatic cells utilizing cellular reprogramming by ectopic expression of transcription factors, thereby laying the foundation for future demonstration of germ line transmission in chickens. Availability of competent iPGC offers new strategies for endangered bird conservation and a new cell source for developmental biology and transgenic animal research.

REFERENCES (FIRST SET)

1. Takahashi K & Yamanaka S (2006) Induction of pluripotent stem cells from mouse embryonic and adult fibroblast cultures by defined factors. *Cell* 126(4):663-676.
2. Yu J, et al. (2007) Induced pluripotent stem cell lines derived from human somatic cells. *Science* 318(5858): 1917-1920.
3. Zhao X Y, et al. (2009) iPS cells produce viable mice through tetraploid complementation. *Nature* 461(7260): 86-90.
4. Thomson J A, et al. (1998) Embryonic stem cell lines derived from human blastocysts. *Science* 282 (5391): 1145-1147.
5. Takahashi K, et al. (2007) Induction of pluripotent stem cells from adult human fibroblasts by defined factors. *Cell* 131 (5): 861-872.
6. West F D, et al. (2010) Porcine induced pluripotent stem cells produce chimeric offspring. *Stem Cells Dev* 19(8): 1211-1220.
7. Wu Y, Zhang Y, Mishra A, Tardif S D, & Hornsby P5 (2010) Generation of induced pluripotent stem cells from newborn marmoset skin fibroblasts. *Stem Cell Res* 4(3): 180-188.
8. Hanna J, et al. (2008) Direct reprogramming of terminally differentiated mature B lymphocytes to pluripotency. *Cell* 133(2):250-264.
9. Haase A, et al. (2009) Generation of induced pluripotent stem cells from human cord blood. *Cell Stem Cell* 5(4): 434-441.
10. Aasen T, et al. (2008) Efficient and rapid generation of induced pluripotent stem cells from human keratinocytes. *Nat Biotechnol* 26(11):1276-1284.
11. Pain B, et al. (1996) Long-term in vitro culture and characterisation of avian embryonic stem cells with multiple morphogenetic potentialities. *Development* 122(8): 2339-2348.
12. Wu Y, Ge C, Zeng W, & Zhang C (2010) Induced multilineage differentiation of chicken embryonic germ cells via embryoid body formation. *Stem Cells Dev* 19(2): 195-202.
13. Le Douarin N M (1993) Embryonic neural chimaeras in the study of brain development. *Trends Neurosci* 16(2): 64-72.
14. Alvarado-Mallart R M (2000) The chick/quail transplantation model to study central nervous system development. *Prog Brain Res* 127:67-98.
15. Kikuchi T, et al. (1998) Clinical and metabolic correction of pompe disease by enzyme therapy in acid maltase-deficient quail. *J Clin Invest* 101(4):827-833.
16. Chen L, Yang P, & Kijlstra A (2002) Distribution, markers, and functions of retinal microglia. *Ocul Immunol Inflamm* 10(1):27-39.
17. Zak P P, et al. (2010) The experimental model for studying of human age retinal degeneration (Japanese quail C. Japonica). *Dokl Biol Sci* 434:297-299.
18. Sheykholeslami K, Kaga K, & Mizutani M (2001) Auditory nerve fiber differences in the normal and neurofilament deficient Japanese quail. *Hear Res* 159(1-2): 117-124.

19. Kinutani M, Coltey M, & Le Douarin N M (1986) Postnatal development of a demyelinating disease in avian spinal cord chimeras. *Cell* 45(2):307-314.
20. Kulesa P M, Bailey C M, Cooper C, & Fraser S E (2010) In ovo live imaging of avian embryos. *Cold Spring Harb Protoc* 2010(6):pdb prot5446.
21. Le Douarin N M (1984) Ontogeny of the peripheral nervous system from the neural crest and the placodes. A developmental model studied on the basis of the quail-chick chimaera system. *Harvey Lect* 80:137-186.
22. Le Douarin N M (2008) Developmental patterning deciphered in avian chimeras. *Dev Growth Differ* 50 Suppl 1:S11-28.
23. Vali N (2008) The Japanese Quail: A Review. *International Journal of Poultry Science* 7(9):925.
24. Huss D, Poynter G, & Lansford R (2008) Japanese quail (Coturnix japonica) as a laboratory animal model. *Lab Anim* (N19 37(11):513-519.
25. Petitte J N, Liu & Yang Z (2004) Avian pluripotent stem cells. *Mech Dev* 121(9):1159-1168.
26. Macdonald J, Glover J D, Taylor L, Sang H M, & McGrew M J (2010) Characterisation and germline transmission of cultured avian primordial germ cells. *PLoS One* 5(11):e15518.
27. Lavial F & Pain B (2010) Chicken embryonic stem cells as a non-mammalian embryonic stem cell model. *Dev Growth Differ* 52(1):101-114.
28. Jung J G, et al. (2005) Development of novel markers for the characterization of chicken primordial germ cells. *Stem Cells* 23(5):689-698.
29. van de Lavoir M C, et al. (2006) Germline transmission of genetically modified primordial germ cells. *Nature* 441(7094):766-769.
30. Park T S & Han J Y (2000) Derivation and characterization of pluripotent embryonic germ cells in chicken. *Mol Reprod Dev* 56(4):475-482.
31. van de Lavoir M C, et al. (2006) High-grade transgenic somatic chimeras from chicken embryonic stem cells. *Mech Dev* 123(1):31-41.
32. Ezashi T, et al. (2009) Derivation of induced pluripotent stem cells from pig somatic cells. *Proc Natl Acad Sci USA* 106(27):10993-10998.
33. Park T S, Kim M A, Lim J M, & Han J Y (2008) Production of quail (Cotumix japonica) germline chimeras derived from in vitro-cultured gonadal primordial germ cells. *Mol Reprod Dev* 75(2):274-281.
34. Vates G E, Hashimoto T, Young W L, & Lawton M T (2005) Angiogenesis in the brain during development: the effects of vascular endothelial growth factor and angiopoietin-2 in an animal model. *J Neurosurg* 103(1):136-145.
35. Dupin E, Calloni Real C, Goncalves-Trentin A, & Le Douarin N M (2007) Neural crest progenitors and stem cells. *CR Biol* 330(6-7):521-529.
36. Le Douarin N M, Tan K, Hallonet M, & Kinutani M (1993) Studying brain development with quail-chick neural chimeras. *Kaibogaku Zasshi* 68(2):152-161.
37. Teillet M A, Ziller C, & Le Douarin N M (2008) Quail-chick chimeras. *Methods Mol Biol* 461:337-350.
38. Zhang J, et al. (1996) Neural tube, skeletal and body wall defects in mice lacking transcription factor AP-2. *Nature* 381(6579):238-241.
39. Lewis J L, et al. (2004) Reiterated Wnt signaling during zebrafish neural crest development. *Development* 131(6):1299-1308.
40. Meulemans D & Bronner-Fraser M (2004) Gene-regulatory interactions in neural crest evolution and development. *Dev Cell* 7(3):291-299.
41. Shin S, et al. (2006) Long-term proliferation of human embryonic stem cell-derived neuroepithelial cells using defined adherent culture conditions. *Stem Cells* 24(1):125-138.
42. Lavial F, et al. (2007) The Oct4 homologue PouV and Nanog regulate pluripotency in chicken embryonic stem cells. *Development* 134(19):3549-3563.
43. Avilion A A, et al. (2003) Multipotent cell lineages in early mouse development depend on SOX2 function. *Genes Dev* 17(1):126-140.
44. Ying Q L, Nichols J, Chambers I, & Smith A (2003) BMP induction of Id proteins suppresses differentiation and sustains embryonic stem cell self-renewal in collaboration with STAT3. *Cell* 115(3):281-292.
45. Xu R H, et al. (2002) BMP4 initiates human embryonic stem cell differentiation to trophoblast. *Nat Biotechnol* 20(12):1261-1264.
46. Nichols J, et al. (1998) Formation of pluripotent stem cells in the mammalian embryo depends on the POU transcription factor Oct4. *Cell* 95(3):379-391.
47. Sato N, Meijer L, Skaltsounis L, Greengard P, & Brivanlou A H (2004) Maintenance of pluripotency in human and mouse embryonic stem cells through activation of Wnt signaling by a pharmacological GSK-3-specific inhibitor. *Nat Med* 10(1):55-63.
48. Ludwig T E, et al. (2006) Derivation of human embryonic stem cells in defined conditions. *Nat Biotechnol* 24(2):185-187.
49. Capecchi M R (1989) Altering the genome by homologous recombination. *Science* 244(4910):1288-1292.
50. Bronner-Fraser M (1994) Neural crest cell formation and migration in the developing embryo. *FASEB J* 8(10):699-706.
51. Wernig M, et al. (2008) Neurons derived from reprogrammed fibroblasts functionally integrate into the fetal brain and improve symptoms of rats with Parkinson's disease. *Proc Natl Acad Sci USA* 105(15):5856-5861.

REFERENCES (SECOND SET)

1. Msoffe P L, et al. (2010) Implementing poultry vaccination and biosecurity at the village level in Tanzania: a social strategy to promote health in free-range poultry populations. (Translated from eng) *Trop Anim Health Prod* 42(2):253-263 (in eng).
2. Snoeck C J, et al. (2009) Newcastle disease virus in West Africa: new virulent strains identified in non-commercial farms. (Translated from eng) *Arch Virol* 154(1):47-54 (in eng).
3. Fasina F O, et al. (2007) Control versus no control: options for avian influenza H5N1 in Nigeria. (Translated from eng) *Zoonoses Public Health* 54(5):173-176 (in eng).
4. Lyall J, et al. (2011) Suppression of avian influenza transmission in genetically modified chickens. (Translated from eng) *Science* 331(6014):223-226 (in eng).
5. Comelissen L A, et al. (2010) A single immunization with soluble recombinant trimeric hemagglutinin protects chickens against highly pathogenic avian influenza virus H5N1. (Translated from eng) *PLoS One* 5(5):e10645 (in eng).
6. Rao S, et al. (2008) Multivalent HA DNA vaccination protects against highly pathogenic H5N1 avian influenza infection in chickens and mice. (Translated from eng) *PLoS One* 3(6):e2432 (in eng).
13. Le Douarin N M (1993) Embryonic neural chimaeras in the study of brain development. *Trends Neurosci* 16(2):64-72.
14. Alvarado-Mallart R M (2000) The chick/quail transplantation model to study central nervous system development. *Prog Brain Res* 127:67-98.
15. Kikuchi T, et al. (1998) Clinical and metabolic correction of pompe disease by enzyme therapy in acid maltase-deficient quail. *J Clin Invest* 101(4):827-833.
16. Chen L, Yang P, & Kijlstra A (2002) Distribution, markers, and functions of retinal microglia. *Ocul Immunol Inflamm* 10(1):27-39.
17. Zak P P, et al. (2010) The experimental model for studying of human age retinal degeneration (Japanese quail C. Japonica). *Dokl Biol Sci* 434:297-299.
18. Sheykholeslami K, Kaga K, & Mizutani M (2001) Auditory nerve fiber differences in the normal and neurofilament deficient Japanese quail. *Hear Res* 159(1-2):117-124.
19. Kinutani M, Coltey M, & Le Douarin N M (1986) Postnatal development of a demyelinating disease in avian spinal cord chimeras. *Cell* 45(2):307-314.
20. Kulesa P M, Bailey C M, Cooper C, & Fraser S E (2010) In ovo live imaging of avian embryos. *Cold Spring Harb Protoc* 2010(6):pdb prot5446.
21. Le Douarin N M (1984) Ontogeny of the peripheral nervous system from the neural crest and the placodes. A developmental model studied on the basis of the quail-chick chimaera system. *Harvey Lect* 80:137-186.
22. Le Douarin N M (2008) Developmental patterning deciphered in avian chimeras. *Dev Growth Differ* 50 Suppl 1:S11-28.
23. Vali N (2008) The Japanese Quail: A Review. *International Journal of Poultry Science* 7(9):925.
24. Huss D, Poynter G, & Lansford R (2008) Japanese quail (Coturnix japonica) as a laboratory animal model. *Lab Anim* (NY) 37(11):513-519.

REFERENCES (THIRD SET)

1. West F D, J L Mumaw, A Gallegos-Cardenas, A Young and S L Stice. (2011). Human haploid cells differentiated from meiotic competent clonal germ cell lines that originated from embryonic stem cells. Stem Cells Dev 20:1079-88.
2. Kee K, V T Angeles, M Flores, H N Nguyen and R A Reijo Pera. (2009). Human DAZL, DAZ and BOULE genes modulate primordial germ-cell and haploid gamete formation. Nature.
3. Wang Q, X Liu, N Tang, D R Archambeault, J Li, H Song, C Tang, B He, M M Matzuk and Y Wang. (2013). GASZ promotes germ cell derivation from embryonic stem cells. Stem Cell Res 11:845-860.
4. Nayernia K, J Nolte, H W Michelmann, J H Lee, K Rathsack, N Drusenheimer, A Dev, G Wulf, I E Ehrmann, D J Elliott, V Okpanyi, U Zechner, T Haaf, A Meinhardt and W Engel. (2006). In vitro-differentiated embryonic stem cells give rise to male gametes that can generate offspring mice. Dev Cell 11:125-32.
5. Antonarakis S E, R Lyle, E T Dermitzakis, A Reymond and S Deutsch. (2004). Chromosome 21 and down syndrome: from genomics to pathophysiology. Nat Rev Genet 5:725-38.
6. Hockner M, G M Pinggera, B Gunther, C Sergi, C Fauth, M Erdel and D Kotzot. (2008). Unravelling the parental origin and mechanism of formation of the 47,XY,i(X)(q10) Klinefelter karyotype variant. Fertil Steril 90:2009 e13-7.
7. Mshelia G D, J D Amin, Z Woldehiwet, R D Murray and G O Egwu. (2009). Epidemiology of Bovine Venereal Campylobacteriosis: Geographic Distribution and Recent Advances in Molecular Diagnostic Techniques. Reprod Domest Anim.
8. Neal M S, E R Reyes, K S Fisher, W A King and P K Basrur. (1998). Reproductive consequences of an X-autosome translocation in a swine herd. Can Vet J 39:232-7.
9. Giesecke K, H Sieme and O Distl. (2010). Infertility and candidate gene markers for fertility in stallions: a review. Vet J 185:265-71.
10. Brown K H, I R Schultz, J G Cloud and J J Nagler. (2008). Aneuploid sperm formation in rainbow trout exposed to the environmental estrogen 17 {alpha}-ethynylestradiol.
11. Hauser R and R Sokol. (2008). Science linking environmental contaminant exposures with fertility and reproductive health impacts in the adult male. Fertil Steril 89:e59-65.
12. Hauser R, Z Chen, L Pothier, L Ryan and L Altshul. (2003). The relationship between human semen parameters and environmental exposure to polychlorinated biphenyls and p,p'-DDE. Environ Health Perspect 111:1505-11.
13. Shamblott M J, J Axelman, S Wang, E M Bugg, J W Littlefield, P J Donovan, P D Blumenthal, G R Huggins and J D Gearhart. (1998). Derivation of pluripotent stem cells from cultured human primordial germ cells. Proc Natl Acad Sci USA 95:13726-31.
14. Matsui Y, D Toksoz, S Nishikawa, S Nishikawa, D Williams, K Zsebo and B L Hogan. (1991). Effect of Steel factor and leukaemia inhibitory factor on murine primordial germ cells in culture. Nature 353:750-2.
15. Resnick J L, L S Bixler, L Cheng and P J Donovan. (1992). Long-term proliferation of mouse primordial germ cells in culture. Nature 359:550-1.
16. Mozdziak P E, J Angerman-Stewart, B Rushton, S L Pardue and J N Petitte. (2005). Isolation of chicken primordial germ cells using fluorescence-activated cell sorting. Poult Sci 84:594-600.
17. Mozdziak P E, R Wysocki, J Angerman-Stewart, S L Pardue and J N Petitte. (2006). Production of chick germline chimeras from fluorescence-activated cell-sorted gonocytes. Poult Sci 85:1764-8.
18. van de Lavoir M C, J H Diamond, P A Leighton, C Mather-Love, B S Heyer, R Bradshaw, A Kerchner, L T Hooi, T M Gessaro, S E Swanberg, M E Delany and R J Etches. (2006). Germline transmission of genetically modified primordial germ cells. Nature 441:766-9.
19. IUCN2012. (Version 2012.2). The IUCN Red List of Threatened Species . . . <http://www.iucnredlist.org> Downloaded on 17 Oct. 2012.
20. Brooke Mde L, S H Butchart, S T Garnett, G M Crowley, N B Mantilla-Beniers and A J Stattersfield. (2008). Rates of movement of threatened bird species between IUCN red list categories and toward extinction. Conserv Biol 22:417-27.
21. Ben-Nun I F, S C Montague, M L Houck, H T Tran, I Garitaonandia, T R Leonardo, Y C Wang, S J Charter, L C Laurent, O A Ryder and J F Loring. (2011). Induced pluripotent stem cells from highly endangered species. Nat Methods 8:829-31.
22. Lavial F, H Acloque, F Bertocchini, D J Macleod, S Boast, E Bachelard, G Montillet, S Thenot, H M Sang, C D Stern, J Samarut and B Pain. (2007). The Oct4 homologue PouV and Nanog regulate pluripotency in chicken embryonic stem cells. Development 134:3549-63.
23. Pain B, M E Clark, M Shen, H Nakazawa, M Sakurai, J Samarut and R J Etches. (1996). Long-term in vitro culture and characterisation of avian embryonic stem cells with multiple morphogenetic potentialities. Development 122:2339-48.
24. Lu Y, F D West, B J Jordan, J L Mumaw, E T Jordan, A Gallegos-Cardenas, R B Beckstead and S L Stice. (2012). Avian-induced pluripotent stem cells derived using human reprogramming factors. Stem Cells Dev 21:394-403.
25. Wernig M, A Meissner, R Foreman, T Brambrink, M Ku, K Hochedlinger, B E Bernstein and R Jaenisch. (2007). In vitro reprogramming of fibroblasts into a pluripotent ES-cell-like state. Nature 448:318-24.
26. Li B C, Z Q Tian, M Sun, Q Xu, X Y Wang, Y R Qin, F Xu, B Gao, K H Wang, H C Sun and G H Chen. (2010). Directional differentiation of chicken primordial germ cells into adipocytes, neuron-like cells, and osteoblasts. Mol Reprod Dev 77:795-801.
27. Wu Y, C Ge, W Zeng and C Zhang. (2010). Induced multilineage differentiation of chicken embryonic germ cells via embryoid body formation. Stem Cells Dev 19:195-202.
28. Nakamura Y, Y Yamamoto, F Usui, T Mushika, T Ono, A R Setioko, K Takeda, K Nirasawa, H Kagami and T Tagami. (2007). Migration and proliferation of primordial germ cells in the early chicken embryo. Poult Sci 86:2182-93.
29. Dumstrei K, R Mennecke and E Raz. (2004). Signaling pathways controlling primordial germ cell migration in zebrafish. J Cell Sci 117:4787-95.
30. Molyneaux K A, H Zinszner, P S Kunwar, K Schaible, J Stebler, M J Sunshine, W O'Brien, E Raz, D Littman, C Wylie and R Lehmann. (2003). The chemokine SDF1/CXCL12 and its receptor CXCR4 regulate mouse germ cell migration and survival. Development 130:4279-86.
31. Doitsidou M, M Reichman-Fried, J Stebler, M Koprunner, J Dorries, D Meyer, C V Esguerra, T Leung and E Raz. (2002). Guidance of primordial germ cell migration by the chemokine SDF-1. Cell 111:647-59.
32. Motono M, T Ohashi, K Nishijima and S Iijima. (2008). Analysis of chicken primordial germ cells. Cytotechnology 57:199-205.
33. Castrillon D H, B J Quade, T Y Wang, C Quigley and C P Crum. (2000). The human VASA gene is specifically expressed in the germ cell lineage. Proc Natl Acad Sci USA 97:9585-90.
34. Hay B, L Y Jan and Y N Jan. (1988). A protein component of Drosophila polar granules is encoded by vasa and has extensive sequence similarity to ATP-dependent helicases. Cell 55:577-87.
35. Tanaka S S, Y Toyooka, R Akasu, Y Katoh-Fukui, Y Nakahara, R Suzuki, M Yokoyama and T Noce. (2000). The mouse homolog of Drosophila Vasa is required for the development of male germ cells. Genes Dev 14:841-53.
36. Ikenishi K and T S Tanaka. (1997). Involvement of the protein of Xenopus vasa homolog (Xenopus vasa-like gene 1, XVLG1) in the differentiation of primordial germ cells. Dev Growth Differ 39:625-33.
37. Macdonald J, J D Glover, L Taylor, H M Sang and M J McGrew. (2010). Characterisation and germline transmission of cultured avian primordial germ cells. PLoS One 5:e15518.
38. Lavial F, H Acloque, E Bachelard, M A Nieto, J Samarut and B Pain. (2009). Ectopic expression of Cvh (Chicken Vasa homologue) mediates the reprogramming of chicken embryonic stem cells to a germ cell fate. Dev Biol 330:73-82.
39. Xu E Y, F L Moore and R A Pera. (2001). A gene family required for human germ cell development evolved from an ancient meiotic gene conserved in metazoans. Proc Natl Acad Sci USA 98:7414-9.
40. Navarro-Costa P, P Nogueira, M Carvalho, F Leal, I Cordeiro, C Calhaz-Jorge, J Goncalves and C E Plancha. (2010). Incorrect DNA methylation of the DAZL promoter CpG island associates with defective human sperm. Hum Reprod 25:2647-54.
41. Richardson T E, K M Chapman, C Tenenhaus Dann, R E Hammer and F K Hamra. (2009). Sterile testis complementation with spermatogonial lines restores fertility to DAZL-deficient rats and maximizes donor germline transmission. PLoS One 4:e6308.
42. Kee K, V T Angeles, M Flores, F I N Nguyen and R A Reijo Pera. (2009). Human DAZL, DAZ and BOULE genes modulate primordial germ-cell and haploid gamete formation. Nature 462:222-5.
43. De Miguel M P, L Cheng, E C Holland, M J Federspiel and P J Donovan. (2002). Dissection of the c-Kit signaling pathway in mouse primordial germ cells by retroviral-mediated gene transfer. Proc Natl Acad Sci USA 99:10458-63.
44. van de Lavoir M C, C Mather-Love, P Leighton, J H Diamond, B S Heyer, R Roberts, L Zhu, P Winters-Digiacinto, A Kerchner, T Gessaro, S Swanberg, M E Delany and R J Etches. (2006). High-grade transgenic somatic chimeras from chicken embryonic stem cells. Mech Dev 123:31-41.
45. Choi J W, S Kim, T M Kim, Y M Kim, H W Seo, T S Park, J W Jeong, G Song and J Y Han. (2010). Basic fibroblast growth factor activates MEK/ERK cell signaling pathway and stimulates the proliferation of chicken primordial germ cells. PLoS One 5:e12968.
46. Petitte J N, G Liu and Z Yang. (2004). Avian pluripotent stem cells. Mech Dev 121:1159-68.
47. Park H J, T S Park, T M Kim, J N Kim, S S Shin, J M Lim and J Y Han. (2006). Establishment of an in vitro culture system for chicken preblastodermal cells. Mol Reprod Dev 73:452-61.
48. Jung J G; D K Kim, T S Park, S D Lee, J M Lim and J Y Han. (2005). Development of novel markers for the characterization of chicken primordial germ cells. Stem Cells 23:689-98.
49. Rengaraj D, Y H Zheng, K S Kang, K J Park, B R Lee, S I Lee, J W Choi and J Y Han. (2010). Conserved expression pattern of chicken DAZL in primordial germ cells and germ-line cells. Theriogenology 74:765-76.
50. Ge C, C Zhang, J Ye, X Tang and Y Wu. (2007). Ginsenosides promote proliferation of chicken primordial germ cells via PKC-involved activation of NF-kappaB. Cell Biol Int 31:1251-6.
51. Takahashi K and S Yamanaka. (2006). Induction of pluripotent stem cells from mouse embryonic and adult fibroblast cultures by defined factors. Cell 126:663-76.
52. Singh A M and S Dalton. (2009). The cell cycle and Myc intersect with mechanisms that regulate pluripotency and reprogramming. Cell Stem Cell 5:141-9.
53. Guo G, J Yang, J Nichols, J S Hall, I Eyres, W Mansfield and A Smith. (2009). Klf4 reverts developmentally programmed restriction of ground state pluripotency. Development 136:1063-9.

54. Rossello R A, C C Chen, R Dai, J T Howard, U Hochgeschwender and E D Jarvis. (2013). Mammalian genes induce partially reprogrammed pluripotent stem cells in non-mammalian vertebrate and invertebrate species. Elife 2:e00036.
55. van de Lavoir M C, E J Collarini, P A Leighton, J Fesler, D R Lu, W D Harriman, T S Thiyagasundaram and R J Etches. (2012). Interspecific germline transmission of cultured primordial germ cells. PLoS One 7:e35664.
56. Burt D W. (2007). Emergence of the chicken as a model organism: implications for agriculture and biology. Poult Sci 86:1460-71.
57. Johnson P A and J R Giles. (2013). The hen as a model of ovarian cancer. Nat Rev Cancer 13:432-6.
58. Semple-Rowland S L, N R Lee, J P Van Hooser, K Palczewski and W Baehr. (1998). A null mutation in the photoreceptor guanylate cyclase gene causes the retinal degeneration chicken phenotype. Proc Natl Acad Sci USA 95:1271-6.

The invention claimed is:

1. A population of isolated chicken cells which have been reprogrammed from chicken somatic cells, wherein said isolated chicken cells comprise exogenous nucleic acid sequences encoding OCT4, SOX2, LIN28 and NANOG genes, and wherein said isolated cells exhibit the following characteristics:
the cells express Alkaline Phosphotase, SSEA1, EMA1, Chicken Vasa Homolog (CVH), DAZL, CXCR4, C-KIT and telomerase; and
the cells are capable of differentiating into all 3 germ layers in vitro.

2. The population of isolated cells according to claim 1 wherein said chicken somatic cells are embryonic chicken somatic cells.

3. The population of isolated cells according to claim 1 wherein said chicken somatic cells are embryonic chicken fibroblast cells.

4. The population of isolated cells according to claim 1 wherein said chicken somatic cells are adult chicken somatic cells.

5. The population of isolated cells according to claim 1 wherein said chicken somatic cells are adult chicken fibroblast cells.

6. The population of isolated cells according to claim 1 wherein said chicken somatic cells are reprogrammed by transfecting or transducing said somatic cells with at least one vector comprising said exogenous genes.

7. The population of isolated cells according to claim 1 wherein said exogenous genes are avian or mammalian genes each of which has a sequence homology of at least about 50% of the identical gene of a chicken.

8. The population according to claim 1 wherein said exogenous genes are chicken, mouse, human, pig or cow genes.

9. The population according to claim 1 wherein said chicken somatic cells are transfected or transduced with vectors wherein each of said vectors comprises a single exogenous gene.

10. The population of cells according to claim 1 wherein said exogenous genes include C-MYC.

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
gagaaggaga agctggagca                                                     20

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2
tcggaccaca tccttctcg                                                      19

<210> SEQ ID NO 3
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 3
cccctgtggt tacctcttcc tcc                                                 23

<210> SEQ ID NO 4
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 4
tgccgttaat ggccgtgcc                                                      19

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
ctatgcctgt gatttgtggg                                                     20

<210> SEQ ID NO 6
<211> LENGTH: 19
<212> TYPE: DNA
<213> ORGANISM: Artificial Sequence
```

-continued

```
<220> FEATURE:
<223> OTHER INFORMATION: synthetic oligonucleotide

<400> SEQUENCE: 6
ggttgtttgc ctttgggac                                                19

<210> SEQ ID NO 7
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 7
ggctccgtgt ccaacca                                                  17

<210> SEQ ID NO 8
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 8
aactccactg cctcaccct                                                19

<210> SEQ ID NO 9
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 9
gtttcatctg cgacccg                                                  17

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 10
caggagcctg cctctttt                                                 18

<210> SEQ ID NO 11
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 11
ggctgatggg caagttcg                                                 18

<210> SEQ ID NO 12
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 12
ctgatcgggc aggaaggat                                                19
```

```
<210> SEQ ID NO 13
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 13
tgcccagaac atcatccca                                                    19

<210> SEQ ID NO 14
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 14
gccagcaccc gcatcaaag                                                    19

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
gagtcaacgg atttggtcgt                                                   20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
ttgattttgg agggatctca                                                   20

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
gtctggatac tcgcagttag g                                                 21

<210> SEQ ID NO 18
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 18
ggtgtaggga ttggggtag                                                    19

<210> SEQ ID NO 19
<211> LENGTH: 21
<212> TYPE: DNA
<213> ORGANISM: Artificial Sequence
<220> FEATURE:
<223> OTHER INFORMATION: synthetic oligonucleotide
```

```
<400> SEQUENCE: 19
tctggatact cgcagttagg t                                                  21

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 20
atggtgctgt tactcacgga c                                                  21

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
cagaagatcg tggaactcgc                                                    20

<210> SEQ ID NO 22
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 22
cactgggtat gttatcgttg gta                                                23

<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 23
cagcgatgag catggcatag ac                                                 22

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 24
cggaagcaga tgtcgtacag g                                                  21
```